United States Patent
Thakur et al.

(10) Patent No.: US 9,926,275 B2
(45) Date of Patent: Mar. 27, 2018

(54) ALLOSTERIC MODULATORS OF THE CANNABINOID 1 RECEPTOR

(71) Applicant: Northeastern University, Boston, MA (US)

(72) Inventors: Ganeshsingh Arjunsingh Thakur, Watertown, MA (US); Ritesh B. Tichkule, Somerville, MA (US); Pushkar Mukund Kulkarni, Boston, MA (US); Abhijit Raghunath Kulkarni, Boston, MA (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 14/911,959

(22) PCT Filed: Aug. 22, 2014

(86) PCT No.: PCT/US2014/052304
§ 371 (c)(1),
(2) Date: Feb. 12, 2016

(87) PCT Pub. No.: WO2015/027160
PCT Pub. Date: Feb. 26, 2015

(65) Prior Publication Data
US 2016/0194284 A1 Jul. 7, 2016

Related U.S. Application Data

(60) Provisional application No. 61/868,794, filed on Aug. 22, 2013, provisional application No. 61/868,807, filed on Aug. 22, 2013.

(51) Int. Cl.
| | | |
|---|---|---|
| *A61K 31/44* | (2006.01) |
| *C07D 213/74* | (2006.01) |
| *C07D 401/12* | (2006.01) |
| *C07D 405/12* | (2006.01) |
| *C07D 413/12* | (2006.01) |
| *C07D 213/40* | (2006.01) |
| *C07D 295/135* | (2006.01) |
| *C07D 413/10* | (2006.01) |

(52) U.S. Cl.
CPC ......... *C07D 213/74* (2013.01); *C07D 213/40* (2013.01); *C07D 295/135* (2013.01); *C07D 401/12* (2013.01); *C07D 405/12* (2013.01); *C07D 413/10* (2013.01); *C07D 413/12* (2013.01)

(58) Field of Classification Search
USPC ..................................... 514/336; 546/268.1
See application file for complete search history.

(56) References Cited

U.S. PATENT DOCUMENTS

| | | | |
|---|---|---|---|
| 5,672,662 A | 9/1997 | Harris et al. | |
| 6,413,996 B2* | 7/2002 | Dahl | C07C 225/22 514/364 |
| 7,008,962 B2* | 3/2006 | Palovich | C07C 225/20 514/345 |
| 7,799,782 B2* | 9/2010 | Munson | C07D 231/56 514/234.5 |
| 2008/0234266 A1 | 9/2008 | Mederski et al. | |
| 2008/0261952 A1* | 10/2008 | Bloxham | A61K 31/341 514/212.01 |
| 2010/0041642 A1* | 2/2010 | Nguyen | C07D 401/12 514/218 |
| 2012/0214808 A1 | 8/2012 | Bloxham et al. | |
| 2014/0296203 A1* | 10/2014 | Lim | C07D 471/04 514/210.18 |

FOREIGN PATENT DOCUMENTS

WO 2012/117216 A1 9/2012

OTHER PUBLICATIONS

Verheijen et al. CAS: 154: 10927, 2010.*
Bloxham et al. CAS: 144: 253908, 2006.*
Lim et al. CAS: 158: 636355, 2013.*
B. De Lange, et al., "Aromatic Amination of Aryl Bromides Catalysed by Copper/β-Diketone Catalysts: The Effect of Concentration", Synlett, (2006), No. 18, pp. 3105-3109.

* cited by examiner

Primary Examiner — Rei Tsang Shiao
(74) Attorney, Agent, or Firm — Posternak Blankstein & Lund LLP

(57) ABSTRACT

The present technology relates to compounds and compositions of Formulas I, II, VII, and VIII, and methods using such compounds. The compounds and compositions described herein may be used in the treatment or prophylaxis of addiction, metabolic syndrome, obesity, and/or a CB1 receptor-mediated disorder.

12 Claims, 7 Drawing Sheets

ALLOSTERIC MODULATORS OF THE CANNABINOID 1 RECEPTOR

CROSS-REFERENCE TO RELATED PATENT APPLICATIONS

This application claims priority to U.S. Provisional Patent Application No. 61/868,794, filed Aug. 22, 2013, and U.S. Provisional Patent Application No. 61/868,807, filed on Aug. 22, 2013, the entire disclosures of which are hereby incorporated by reference in their entireties for any and all purposes.

STATEMENT REGARDING FEDERALLY SPONSORED RESEARCH OR DEVELOPMENT

This invention was made with government support under DA027113 awarded by the National Institutes of Health. The government has certain rights in the invention.

FIELD

The present technology is directed to compounds, compositions, and methods to selectively modulate the cannabinoid 1 (CB1) receptor. The technology is suited to treat addiction, metabolic syndrome, obesity, or other CB1 receptor-mediated disorders.

SUMMARY

The present technology is directed to compounds, compositions, and methods to selectively modulate the cannabinoid 1 (CB1) receptor. The technology is suited to treat addiction, metabolic syndrome, obesity, or other CB1 receptor-mediated disorders. In particular, the technology is especially suited to treat addiction in a subject.

In one aspect of the present technology, a compound of formula I is provided

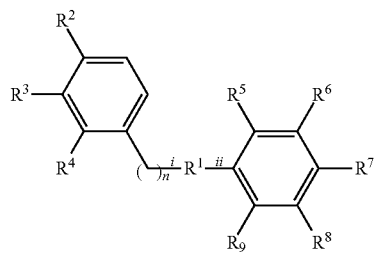

I as well as stereoisomers thereof, tautomers thereof, solvates thereof, or pharmaceutically acceptable salts thereof; wherein i and ii designate the particular bonds indicated in formula I; $R^1$ is selected from formulas A, B, C, or D

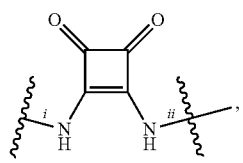

A

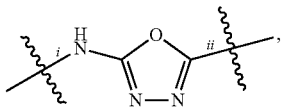

B

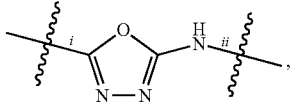

C

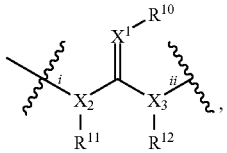

D where $X^1$, $X^2$, and $X^3$ are each independently O, N, or S; and $R^{10}$, $R^{11}$, and $R^{12}$ are each independently H, cyano, amino, or a substituted or unsubstituted alkyl, alkanoyl, alkanoyloxy, or aryl group when $X^1$, $X^2$, or $X^3$ are respectively N and are absent when $X^1$, $X^2$, and $X^3$ are respectively O or S; or $R^{11}$ and $R^4$ together form a substituted or unsubstituted 5- or 6-membered heterocylyl ring; $R^2$, $R^3$, and $R^4$ are each independently H, halo, cyano, trifluoromethyl, nitro, trialkyl ammonium, azido, trifluoromethyldiazirido, isocyano, isothiocyano, pentafluorosulfanyl, or a substituted or unsubstituted alkyl, alkoxy, aryl, aryloxy, alkynyl, heterocyclylalkyl, alkanoyl, alkanoyloxy, aryloyl, aryloyloxy, carboxylate, or ester group, or where $R^2$ and $R^3$ or $R^3$ and $R^4$ form a substituted or unsubstituted 5- or 6-membered cycloalkyl, aryl, or heteroaryl ring, or $R^3$ and $R^4$ together form a substituted or unsubstituted 5- or 6-membered cycloalkyl, aryl, or heteroaryl ring; one of $R^5$, $R^6$, or $R^7$ is

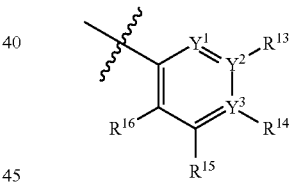

and the remaining $R^5$, $R^6$, or $R^7$ are each independently H, halo, azido, trifluoromethyldiazirido, isocyano, isothiocyano, or a substituted or unsubstituted alkyl, alkanoyl, alkanoyloxy, aryloyl, or aryloyloxy group; where one of $R^{13}$ or $R^{14}$ is

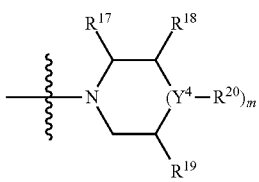

and the other is H, azido, trifluoromethyldiazirido, isocyano, isothiocyano, or a substituted or unsubstituted alkyl, alkanoyl, alkanoyloxy, aryloyl, or aryloyloxy group; $R^{15}$ and $R^{16}$ are each independently H, halo, azido, trifluoromethyldiazirido, isocyano, isothiocyano, or a substituted or unsubstituted alkyl, alkanoyl, alkanoyloxy, aryloyl, or aryloyloxy group; $Y^1$ is CH or N; $Y^2$ and $Y^3$ are each independently C or N, provided that when $Y^2$ or $Y^3$ is N then $R^{13}$ or $R^{14}$ respectively is absent; $Y^4$ is CH, N, O, S, S(O), or S(O)$_2$; $R^{17}$, $R^{18}$, and $R^{19}$ are each independently H, azido, trifluoromethyldiazirido, isocyano, isothiocyano, or a substituted or unsubstituted alkyl group; $R^{20}$ is H or a substituted or unsubstituted alkyl group when $Y^4$ is CH or N and is absent when $Y^4$ is O, S, S(O), or S(O)$_2$; m is 0 or 1; $R^8$ and $R^9$ are each independently H or a substituted or unsubstituted alkyl group; and n is 0 or 1;

with the proviso that $R^2$ is not Cl when $R^1$ is formula D, $X^1$ is O, $X^2$ and $X^3$ are each N, $R^3$ and $R^4$ are each H, $R^5$, $R^7$, $R^8$, and $R^9$ are each H, $R^6$ is

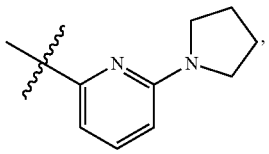 [SMILES: *c1cccc(N2CCCC2)n1]

$R^{11}$ and $R^{12}$ are each H, and n is 0. In some embodiments of a compound of formula I, at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group. In some embodiments of a compound of formula I, one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group, and the remaining $R^2$, $R^3$, and $R^4$ are not.

In some embodiments of a compound of formula I, $R^1$ is formula A, as represented by formula III

III

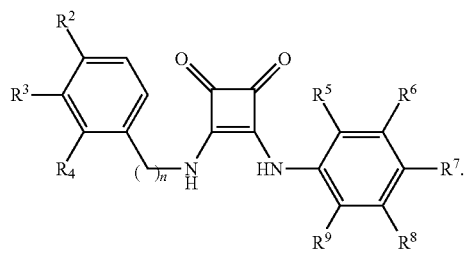

In some embodiments of a compound of formula III, one of $Y^1$, $Y^2$, and $Y^3$ is N while the remaining $Y^1$, $Y^2$, and $Y^3$ are not N. In some embodiments of formula I, at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group. In some embodiments of a compound of formula III, one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group, and the remaining $R^2$, $R^3$, and $R^4$ are not.

In some embodiments of a compound of formula III, $R^2$, $R^3$, and $R^4$ are each independently H, halo, cyano, trifluoromethyl, nitro, trialkyl ammonium, or a substituted or unsubstituted alkyl, alkoxy, aryl, aryloxy, alkynyl, heterocyclylalkyl, alkanoyl, alkanoyloxy, aryloyl, aryloyloxy, carboxylate, or ester group;

one of $R^5$, $R^6$, or $R^7$ is

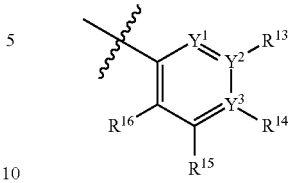

and the remaining $R^5$, $R^6$, or $R^7$ are each independently H, halo, or a substituted or unsubstituted alkyl, alkanoyl, alkanoyloxy, aryloyl, or aryloyloxy group; where one of $R^{13}$ or $R^{14}$ is

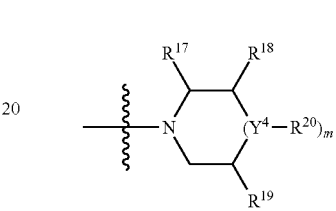

and the other is H, or a substituted or unsubstituted alkyl, alkanoyl, alkanoyloxy, aryloyl, or aryloyloxy group; $R^{15}$ and $R^{16}$ are each independently H, halo, or a substituted or unsubstituted alkyl, alkanoyl, alkanoyloxy, aryloyl, or aryloyloxy group; and $R^{17}$, $R^{18}$, and $R^{19}$ are each independently H, or a substituted or unsubstituted alkyl group. In some embodiments of a compound of formula III, at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group.

In some embodiments of a compound of formula III, $R^2$, $R^3$, and $R^4$ are each independently H, halo, cyano, trifluoromethyl, nitro, or a substituted or unsubstituted alkyl, alkoxy, aryl, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;

one of $R^5$, $R^6$, or $R^7$ is

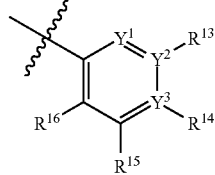

and the remaining $R^5$, $R^6$, or $R^7$ are each independently H or a substituted or unsubstituted alkyl, alkanoyl, alkanoyloxy, aryloyl, or aryloyloxy group; where one of $R^{13}$ or $R^{14}$ is

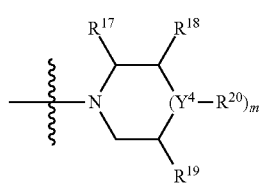

and the other is H or absent; $R^{15}$ and $R^{16}$ are each independently H or a substituted or unsubstituted alkyl, alkanoyl, alkanoyloxy, aryloyl, or aryloyloxy group; and $R^{17}$, $R^{18}$, and $R^{19}$ are each independently H, or a substituted or unsubstituted alkyl group.

In some embodiments of a compound of formula III, $R^2$, $R^3$, and $R^4$ are each independently H, halo, cyano, trifluoromethyl, nitro, or a substituted or unsubstituted alkyl, alkoxy, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;

one of $R^5$, $R^6$, or $R^7$ is

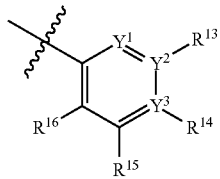

and the remaining $R^5$, $R^6$, or $R^7$ are each independently H or a substituted or unsubstituted alkyl group; where one of $R^{13}$ or $R^{14}$ is

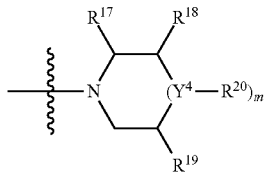

and the other is H or absent; $R^{15}$ and $R^{16}$ are each independently H or a substituted or unsubstituted alkyl group; and $R^{17}$, $R^{18}$, and $R^{19}$ are each independently H, or a substituted or unsubstituted alkyl group. In some embodiments of formula III, $R^2$, $R^3$, and $R^4$ are each independently H, halo, cyano, trifluoromethyl, nitro, or a substituted or unsubstituted alkyl, alkoxy, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;

one of $R^5$, $R^6$, or $R^7$ is

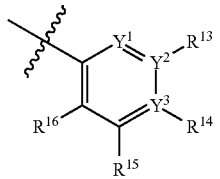

and the remaining $R^5$, $R^6$, or $R^7$ are each independently H or an unsubstituted alkyl group; where one of $R^{13}$ or $R^{14}$ is

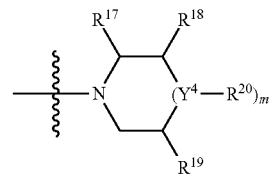

and the other is H or absent; $R^{15}$ and $R^{16}$ are each independently H or a substituted or unsubstituted alkyl group; $R^{17}$, $R^{18}$, and $R^{19}$ are each independently H or a substituted or unsubstituted alkyl group; $Y^4$ is CH, N, or O; $R^{20}$ is H or an unsubstituted alkyl group when $Y^4$ is CH or N and is absent when $Y^4$ is O; and $R^8$ and $R^9$ are each independently H.

In some embodiments of a compound of formula III, $R^2$, $R^3$, and $R^4$ are each independently H, halo, cyano, trifluoromethyl, nitro, or a substituted or unsubstituted alkyl, alkoxy, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;

one of $R^5$, $R^6$, or $R^7$ is

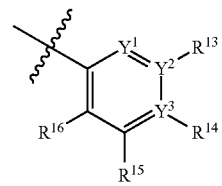

and the remaining $R^5$, $R^6$, or $R^7$ are each independently H or an unsubstituted alkyl group; where one of $R^{13}$ or $R^{14}$ is

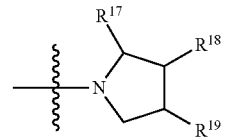

and the other is H or absent; $R^{15}$ and $R^{16}$ are each independently H or a substituted or unsubstituted alkyl group; $R^{17}$, $R^{18}$, and $R^{19}$ are each independently H or a substituted or unsubstituted alkyl group; and $R^8$ and $R^9$ are each independently H.

In some embodiments of a compound of formula III, $R^2$, $R^3$, and $R^4$ are each independently H, halo, cyano, trifluoromethyl, nitro, or a substituted or unsubstituted alkyl, alkoxy, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;

one of $R^5$, $R^6$, or $R^7$ is

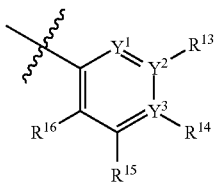

and the remaining $R^5$, $R^6$, or $R^7$ are each independently H or an unsubstituted alkyl group; where one of $R^{13}$ or $R^{14}$ is

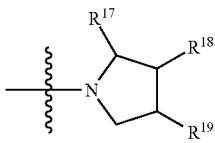

and the other is H or absent; $R^{15}$ and $R^{16}$ are each independently H or an unsubstituted alkyl group; one of $Y^1$, $Y^2$, and $Y^3$ is N while the remaining $Y^1$, $Y^2$, and $Y^3$ are not N; $R^{17}$, $R^{18}$, and $R^{19}$ are each independently H or an unsubstituted alkyl group; and $R^8$ and $R^9$ are each independently H.

In some embodiments of a compound of formula III, $R^2$, $R^3$, and $R^4$ are each independently H, halo, cyano, trifluoromethyl, nitro, or a substituted or unsubstituted alkyl, alkoxy, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;

one of $R^5$, $R^6$, or $R^7$ is

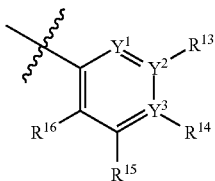

and the remaining $R^5$, $R^6$, or $R^7$ are each independently H; where one of $R^{13}$ or $R^{14}$ is

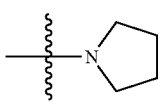

and the other is H or absent; $R^{15}$ and $R^{16}$ are each independently H or an unsubstituted alkyl group; one of $Y^1$, $Y^2$, and $Y^3$ is N while the remaining $Y^1$, $Y^2$, and $Y^3$ are not N; and $R^8$ and $R^9$ are each independently H.

In some embodiments of a compound of formula III, one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group, and the remaining $R^2$, $R^3$, and $R^4$ are each independently H;

one of $R^5$, $R^6$, or $R^7$ is

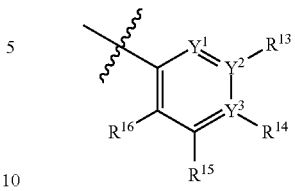

and the remaining $R^5$, $R^6$, or $R^7$ are each independently H; where one of $R^{13}$ or $R^{14}$ is

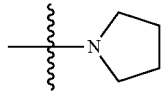

and the other is H or absent; $R^{15}$ and $R^{16}$ are each independently H or an unsubstituted alkyl group; one of $Y^1$, $Y^2$, and $Y^3$ is N while the remaining $Y^1$, $Y^2$, and $Y^3$ are not N; and $R^8$ and $R^9$ are each independently H.

In some embodiments of a compound of formula I, wherein $R^1$ is formula B as represented by formula IV, or $R^1$ is formula C as represented by formula V

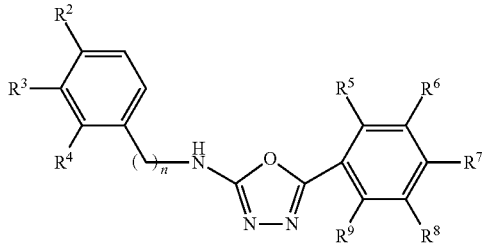

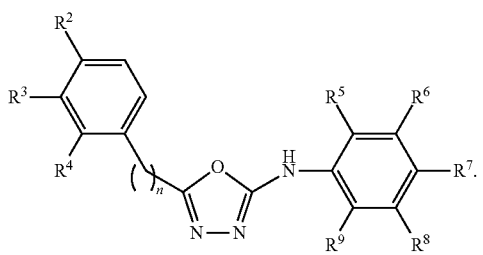

In some embodiments of a compound of formulas IV or V, one of $Y^1$, $Y^2$, and $Y^3$ is N while the remaining $Y^1$, $Y^2$, and $Y^3$ are not N. In some embodiments of formulas IV or V, at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group. In some embodiments of a compound of formulas IV or V, one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group, and the remaining $R^2$, $R^3$, and $R^4$ are not.

In some embodiments of a compound of formulas IV or V, $R^2$, $R^3$, and $R^4$ are each independently H, halo, cyano, trifluoromethyl, nitro, trialkyl ammonium, or a substituted or unsubstituted alkyl, alkoxy, aryl, aryloxy, alkynyl, heterocyclylalkyl, alkanoyl, alkanoyloxy, aryloyl, aryloyloxy, carboxylate, or ester group;

one of $R^5$, $R^6$, or $R^7$ is

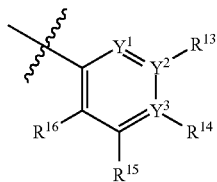

and the remaining $R^5$, $R^6$, or $R^7$ are each independently H, halo, or a substituted or unsubstituted alkyl, alkanoyl, alkanoyloxy, aryloyl, or aryloyloxy group; where one of $R^{13}$ or $R^{14}$ is

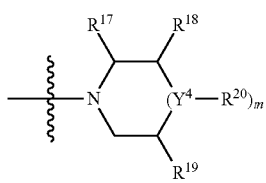

and the other is H, or a substituted or unsubstituted alkyl, alkanoyl, alkanoyloxy, aryloyl, or aryloyloxy group; $R^{15}$ and $R^{16}$ are each independently H, halo, or a substituted or unsubstituted alkyl, alkanoyl, alkanoyloxy, aryloyl, or aryloyloxy group; and $R^{17}$, $R^{18}$, and $R^{19}$ are each independently H or a substituted or unsubstituted alkyl group.

In some embodiments of a compound of formulas IV or V, $R^2$, $R^3$, and $R^4$ are each independently H, halo, cyano, trifluoromethyl, nitro, or a substituted or unsubstituted alkyl, alkoxy, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;
one of $R^5$, $R^6$, or $R^7$ is

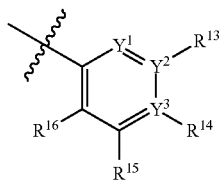

and the remaining $R^5$, $R^6$, or $R^7$ are each independently H or an unsubstituted alkyl group; where one of $R^{13}$ or $R^{14}$ is

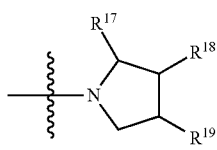

and the other is H or absent; $R^{15}$ and $R^{16}$ are each independently H or an unsubstituted alkyl group; one of $Y^1$, $Y^2$, and $Y^3$ is N while the remaining $Y^1$, $Y^2$, and $Y^3$ are not N; $R^{17}$, $R^{18}$, and $R^{19}$ are each independently H or an unsubstituted alkyl group; and $R^8$ and $R^9$ are each independently H.

In some embodiments of a compound of formulas IV or V, $R^2$, $R^3$, and $R^4$ are each independently H, halo, cyano, trifluoromethyl, nitro, or a substituted or unsubstituted alkyl, alkoxy, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;
one of $R^5$, $R^6$, or $R^7$ is

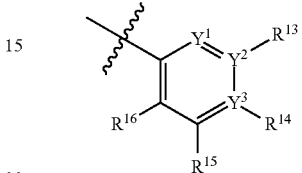

and the remaining $R^5$, $R^6$, or $R^7$ are each independently H; where one of $R^{13}$ or $R^{14}$ is

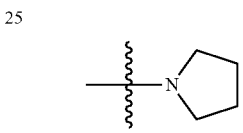

and the other is H or absent; $R^{15}$ and $R^{16}$ are each independently H or an unsubstituted alkyl group; one of $Y^1$, $Y^2$, and $Y^3$ is N while the remaining $Y^1$, $Y^2$, and $Y^3$ are not N; and $R^8$ and $R^9$ are each independently H.

In some embodiments of a compound of formulas IV or V, one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group, and the remaining $R^2$, $R^3$, and $R^4$ are each independently H:
one of $R^5$, $R^6$, or $R^7$ is

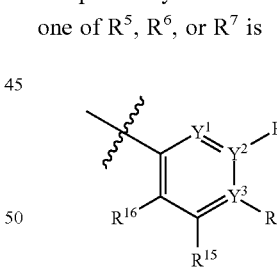

and the remaining $R^5$, $R^6$, or $R^7$ are each independently H; where one of $R^{13}$ or $R^{14}$ is

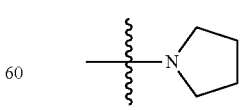

and the other is H or absent; $R^{15}$ and $R^{16}$ are each independently H or an unsubstituted alkyl group; one of $Y^1$, $Y^2$, and $Y^3$ is N while the remaining $Y^1$, $Y^2$, and $Y^3$ are not N; and $R^8$ and $R^9$ are each independently H.

In some embodiments of a compound of formula I, $R^1$ is formula D, as represented by formula VI

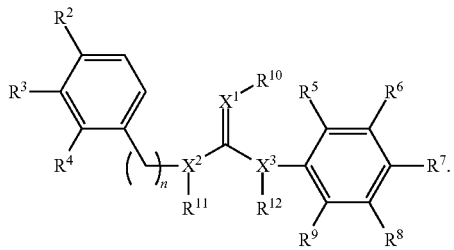

VI

In some embodiments of a compound of formula VI, at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group. In some embodiments of a compound of formula VI, one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group, and the remaining $R^2$, $R^3$, and $R^4$ are not. In some embodiments of a compound of formula VI, $R^2$, $R^3$, and $R^4$ are each independently H, halo, cyano, trifluoromethyl, nitro, trialkyl ammonium, or a substituted or unsubstituted alkyl, alkoxy, aryl, aryloxy, alkynyl, heterocyclylalkyl, alkanoyl, alkanoyloxy, aryloyl, aryloyloxy, carboxylate, or ester group;
one of $R^5$, $R^6$, or $R^7$ is

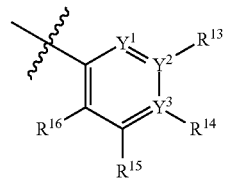

and the remaining $R^5$, $R^6$, or $R^7$ are each independently H, halo, or a substituted or unsubstituted alkyl, alkanoyl, alkanoyloxy, aryloyl, or aryloyloxy group; where one of $R^{13}$ or $R^{14}$ is

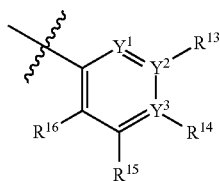

and the other is H, or a substituted or unsubstituted alkyl, alkanoyl, alkanoyloxy, aryloyl, or aryloyloxy group; and $R^{15}$ and $R^{16}$ are each independently H, halo, or a substituted or unsubstituted alkyl, alkanoyl, alkanoyloxy, aryloyl, or aryloyloxy group.

In some embodiments of a compound of formula VI, $R^2$, $R^3$, and $R^4$ are each independently H, halo, cyano, trifluoromethyl, nitro, or a substituted or unsubstituted alkyl, alkoxy, aryl, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;
one of $R^5$, $R^6$, or $R^7$ is

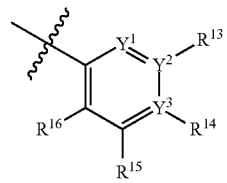

and the remaining $R^5$, $R^6$, or $R^7$ are each independently H or a substituted or unsubstituted alkyl, alkanoyl, alkanoyloxy, aryloyl, or aryloyloxy group; where one of $R^{13}$ or $R^{14}$ is

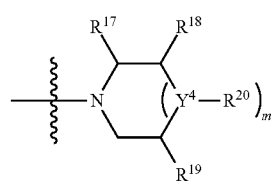

and the other is H or absent; $R^{15}$ and $R^{16}$ are each independently H or a substituted or unsubstituted alkyl, alkanoyl, alkanoyloxy, aryloyl, or aryloyloxy group; and $R^{17}$, $R^{18}$, and $R^{19}$ are each independently H or a substituted or unsubstituted alkyl group.

In some embodiments of a compound of formula VI, $R^2$, $R^3$, and $R^4$ are each independently H, halo, cyano, trifluoromethyl, nitro, or a substituted or unsubstituted alkyl, alkoxy, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;
one of $R^5$, $R^6$, or $R^7$ is

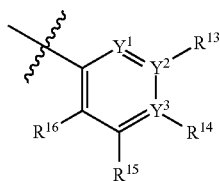

and the remaining $R^5$, $R^6$, or $R^7$ are each independently H or a substituted or unsubstituted alkyl group; where one of $R^{13}$ or $R^{14}$ is

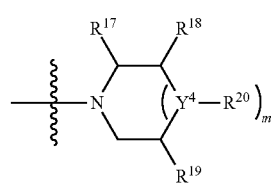

and the other is H or absent; $R^{15}$ and $R^{16}$ are each independently H or a substituted or unsubstituted alkyl group; and $R^{17}$, $R^{18}$, and $R^{19}$ are each independently H or a substituted or unsubstituted alkyl group.

In some embodiments of a compound of formula VI, $R^2$, $R^3$, and $R^4$ are each independently H, halo, cyano, trifluoromethyl, nitro, or a substituted or unsubstituted alkyl, alkoxy, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;

one of $R^5$, $R^6$, or $R^7$ is

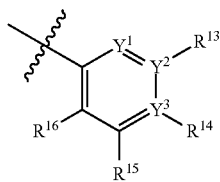

and the remaining $R^5$, $R^6$, or $R^7$ are each independently H or an unsubstituted alkyl group; where one of $R^{13}$ or $R^{14}$ is

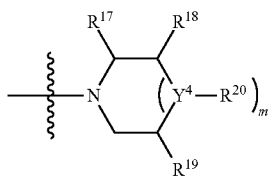

and the other is H or absent; $R^{15}$ and $R^{16}$ are each independently H or a substituted or unsubstituted alkyl group; $R^{17}$, $R^{18}$, and $R^{19}$ are each independently H or a substituted or unsubstituted alkyl group; $Y^4$ is CH, N, or O; $R^{20}$ is H or an unsubstituted alkyl group when $Y^4$ is CH or N and is absent when $Y^4$ is O; and $R^8$ and $R^9$ are each independently H.

In some embodiments of a compound of formula VI, $R^2$, $R^3$, and $R^4$ are each independently H, halo, cyano, trifluoromethyl, nitro, or a substituted or unsubstituted alkyl, alkoxy, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;

one of $R^5$, $R^6$, or $R^7$ is

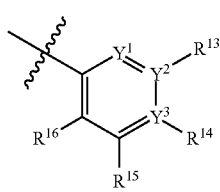

and the remaining $R^5$, $R^6$, or $R^7$ are each independently H or an unsubstituted alkyl group; where one of $R^{13}$ or $R^{14}$ is

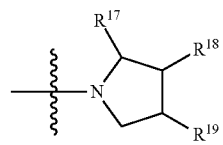

and the other is H or absent; $R^{15}$ and $R^{16}$ are each independently H or a substituted or unsubstituted alkyl group; $R^{17}$, $R^{18}$, and $R^{19}$ are each independently H, or a substituted or unsubstituted alkyl group; and $R^8$ and $R^9$ are each independently H.

In some embodiments of a compound of formula VI, $R^2$, $R^3$, and $R^4$ are each independently H, halo, cyano, trifluoromethyl, nitro, or a substituted or unsubstituted alkyl, alkoxy, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;

one of $R^5$, $R^6$, or $R^7$ is

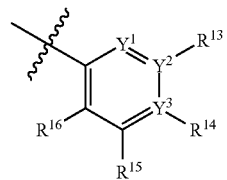

and the remaining $R^5$, $R^6$, or $R^7$ are each independently H or an unsubstituted alkyl group; where one of $R^{13}$ or $R^{14}$ is

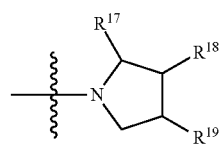

and the other is H or absent; $R^{15}$ and $R^{16}$ are each independently H or an unsubstituted alkyl group; one of $Y^1$, $Y^2$, and $Y^3$ is N while the remaining $Y^1$, $Y^2$, and $Y^3$ are not N; $R^{17}$, $R^{18}$, and $R^{19}$ are each independently H or an unsubstituted alkyl group; and $R^8$ and $R^9$ are each independently H.

In some embodiments of a compound of formula VI, $R^2$, $R^3$, and $R^4$ are each independently H, halo, cyano, trifluoromethyl, nitro, or a substituted or unsubstituted alkyl, alkoxy, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;

one of $R^5$, $R^6$, or $R^7$ is

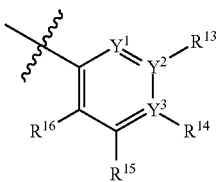

and the remaining $R^5$, $R^6$, or $R^7$ are each independently H; where one of $R^{13}$ or $R^{14}$ is

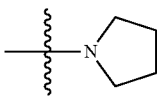

and the other is H or absent; $R^{15}$ and $R^{16}$ are each independently H or an unsubstituted alkyl group; one of $Y^1$, $Y^2$, and $Y^3$ is N while the remaining $Y^1$, $Y^2$, and $Y^3$ are not N; and $R^8$ and $R^9$ are each independently H.

In some embodiments of a compound of formula VI, one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group, and the remaining $R^2$, $R^3$, and $R^4$ are each independently H;

one of $R^5$, $R^6$, or $R^7$ is

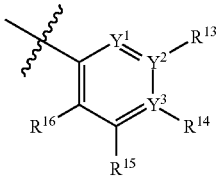

and the remaining $R^5$, $R^6$, or $R^7$ are each independently H; where one of $R^{13}$ or $R^{14}$ is

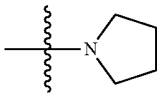 [SMILES: *N1CCCC1]

and the other is H or absent; $R^{15}$ and $R^{16}$ are each independently H or an unsubstituted alkyl group; one of $Y^1$, $Y^2$, and $Y^3$ is N while the remaining $Y^1$, $Y^2$, and $Y^3$ are not N; and $R^8$ and $R^9$ are each independently H.

In any of the above embodiments of a compound of formula VI, it may be that at least one of $R^2$, $R^3$, $R^4$, $R^5$, $R^6$, $R^7$, $R^{13}$, $R^{14}$, $R^{15}$, $R^{16}$, $R^{17}$, $R^{18}$, or $R^{19}$ is azido, trifluoromethyldiazirido, isocyano, or thioisocyano.

In any of the above aspects and embodiments of compounds of formulas I, III, IV, V, or VI, it may be that $R^2$ is not halo when $R^1$ is formula D, $X^1$ is O, $X^2$ and $X^3$ are N, $R^3$ and $R^4$ are H, $R^5$, $R^7$, $R^8$, and $R^9$ are H, $R^6$ is

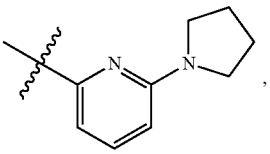 [SMILES: *c1cccc(N2CCCC2)n1]

$R^{11}$ and $R^{12}$ are H, and n is 0.

In an aspect, a compound of formula II is provided

II

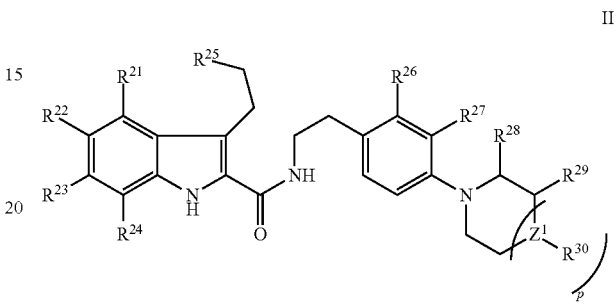

as well as stereoisomers thereof, tautomers thereof, solvates thereof, or pharmaceutically acceptable salts thereof; where $R^{21}$, $R^{22}$, $R^{23}$, $R^{24}$, $R^{25}$, $R^{26}$, $R^{27}$, $R^{28}$, and $R^{29}$ are each independently H, halo, cyano, trifluoromethyl, nitro, trialkyl ammonium, azido, trifluoromethyldiazirido, isocyano, isothiocyano, pentafluorosulfanyl, or a substituted or unsubstituted alkyl, alkoxy, aryl, aryloxy, alkynyl, heterocyclylalkyl, alkanoyl, alkanoyloxy, aryloyl, aryloyloxy, carboxylate, or ester group, provided that at least one of $R^{21}$, $R^{22}$, $R^{23}$, or $R^{24}$ is halo, cyano, trifluoromethyl, nitro, trialkyl ammonium, azido, trifluoromethyldiazirido, isocyano, isothiocyano, or a substituted or unsubstituted alkoxy, aryloxy, alkanoyl, alkanoyloxy, aryloyl, aryloyloxy, carboxylate, or ester group; $Z^1$ is CH, N, O, S, S(O), or S(O)$_2$; $R^{30}$ is H, halo, cyano, trifluoromethyl, nitro, trialkyl ammonium, azido, trifluoromethyldiazirido, isocyano, isothiocyano, or a substituted or unsubstituted alkyl, alkoxy, aryl, aryloxy, alkynyl, heterocyclylalkyl, alkanoyl, alkanoyloxy, aryloyl, aryloyloxy, carboxylate, or ester group, provided that $R^{30}$ is absent when $Z^1$ is O, S, S(O), or S(O)$_2$; p is 0 or 1;

with the proviso that $R^{22}$ is not Cl when p is 1, $R^{21}$, $R^{23}$, $R^{24}$, $R^{26}$, $R^{27}$, $R^{28}$, $R^{29}$ and $R^{30}$ are each H, $R^{25}$ is H or unsubstituted alkyl, and $Z^1$ is CH. In some embodiments of a compound of formula II, $R^{21}$, $R^{22}$, $R^{23}$, $R^{24}$, $R^{25}$, $R^{26}$, $R^{27}$, $R^{28}$, and $R^{29}$ are each independently H, halo, cyano, trifluoromethyl, nitro, azido, trifluoromethyldiazirido, isocyano, isothiocyano, or a substituted or unsubstituted alkyl, alkoxy, aryl, aryloxy, alkynyl, heterocyclylalkyl, alkanoyl, alkanoyloxy, aryloyl, aryloyloxy, carboxylate, or ester group, provided that at least one of $R^{21}$, $R^{22}$, $R^{23}$, or $R^{24}$ is halo, cyano, trifluoromethyl, nitro, azido, trifluoromethyldiazirido, isocyano, isothiocyano, or a substituted or unsubstituted alkoxy, aryloxy, alkanoyl, alkanoyloxy, aryloyl, aryloyloxy, carboxylate, or ester group; and $R^{30}$ is H, cyano, trifluoromethyl, nitro, azido, trifluoromethyldiazirido, isocyano, isothiocyano, or a substituted or unsubstituted alkyl, alkoxy, aryl, aryloxy, alkynyl, heterocyclylalkyl, alkanoyl, alkanoyloxy, aryloyl, aryloyloxy, carboxylate, or ester group, provided that $R^{30}$ is absent when $Z^1$ is O, S, S(O), or S(O)$_2$.

In some embodiments of a compound of formula II, at least one of $R^{21}$, $R^{22}$, $R^{23}$, $R^{24}$, $R^{25}$, $R^{26}$, $R^{27}$, $R^{28}$, $R^{29}$ or $R^{30}$ is azido, trifluoromethyldiazirido, isocyano, or isothiocyano.

In any of the embodiments of a compound of formula II, it may be that $R^{20}$ is not halo when p is 1, $R^{21}$, $R^{23}$, $R^{24}$, $R^{25}$, $R^{26}$, $R^{27}$, $R^{28}$, $R^{29}$, and $R^{30}$ are each H, and $Z^1$ is CH. In any of the embodiments of a compound of formula II, it may be that $R^{20}$ is not halo when p is 1, $R^{21}$, $R^{23}$, $R^{24}$, $R^{26}$, $R^{27}$, $R^{28}$, $R^{29}$, and $R^{30}$ are each H, $R^{25}$ is H or unsubstituted alkyl, and $Z^1$ is CH.

In an aspect, a compound according to formula VII is provided

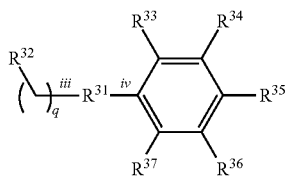

VII as well as stereoisomers thereof, tautomers thereof, solvates thereof, or pharmaceutically acceptable salts thereof; where iii and iv designate the particular bonds indicated in formula VII; $R^{31}$ is selected from formulas E, F, G, or H

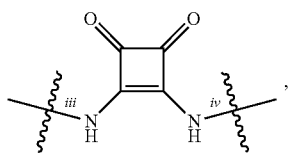

E

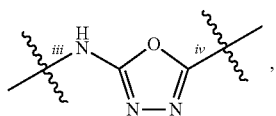

F

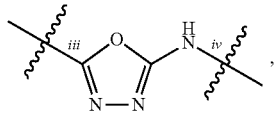

G

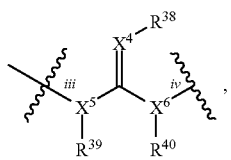

H where $X^4$, $X^5$, and $X^6$ are each independently O, N, or S; $R^{38}$, $R^{39}$, and $R^{40}$ are each independently H, cyano, amino, or a substituted or unsubstituted alkyl, alkanoyl, alkanoyloxy, or aryl group when $X^4$, $X^5$, or $X^6$ are respectively N and are absent when $X^4$, $X^5$, and $X^6$ are respectively O or S; $R^{32}$ is H or unsubstituted alkyl, cycloalkyl, or heterocylyl group;

one of $R^{33}$, $R^{34}$, or $R^{35}$ is

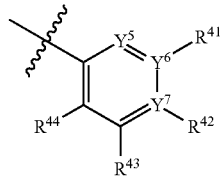

and the remaining $R^{33}$, $R^{34}$, or $R^{35}$ are each independently H, halo, azido, trifluoromethyldiazirido, isocyano, isothiocyano, or a substituted or unsubstituted alkyl, alkanoyl, alkanoyloxy, aryloyl, or aryloyloxy group; where one of $R^{41}$ or $R^{42}$ is

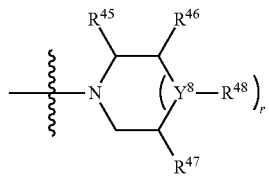

and the other is H, azido, trifluoromethyldiazirido, isocyano, isothiocyano, or a substituted or unsubstituted alkyl, alkanoyl, alkanoyloxy, aryloyl, or aryloyloxy group; $R^{43}$ and $R^{44}$ are each independently H, halo, azido, trifluoromethyldiazirido, isocyano, isothiocyano, or a substituted or unsubstituted alkyl, alkanoyl, alkanoyloxy, aryloyl, or aryloyloxy group; $Y^5$ is CH or N; $Y^6$ and $Y^7$ are each independently C or N, provided that when $Y^6$ or $Y^7$ is N then $R^{41}$ or $R^{42}$ respectively is absent; $Y^8$ is CH, N, O, S, S(O), or S(O)$_2$; $R^{45}$, $R^{46}$, and $R^{47}$ are each independently H, azido, trifluoromethyldiazirido, isocyano, isothiocyano, or a substituted or unsubstituted alkyl group; $R^{48}$ is H or a substituted or unsubstituted alkyl group when $Y^8$ is CH or N and is absent when $Y^8$ is O, S, S(O), or S(O)$_2$; r is 0 or 1; $R^{36}$ and $R^{37}$ are each independently H or a substituted or unsubstituted alkyl group; and q is 0 or 1.

In some embodiments of a compound of formula VII, one of $R^{33}$, $R^{34}$, or $R^{35}$ is

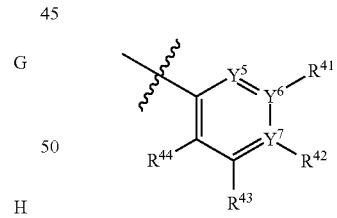

and the remaining $R^{33}$, $R^{34}$, or $R^{35}$ are each independently H or an unsubstituted alkyl group; where one of $R^{41}$ or $R^{42}$ is

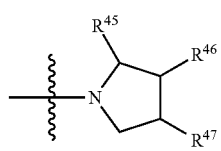

and the other is H or absent; $R^{43}$ and $R^{44}$ are each independently H or an unsubstituted alkyl group; one of $Y^5$, $Y^6$, and $Y^7$ is N while the remaining $Y^5$, $Y^6$, and $Y^7$ are not N; $R^{45}$, $R^{46}$, and $R^{47}$ are each independently H or an unsubstituted alkyl group; and $R^{36}$ and $R^{37}$ are each independently H. In some embodiments of a compound of formula VII, $R^{31}$ is formula H; one of $R^{33}$, $R^{34}$, or $R^{35}$ is

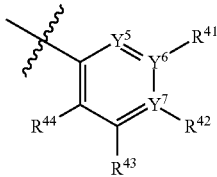

and the remaining $R^{33}$, $R^{34}$, or $R^{35}$ are each independently H or an unsubstituted alkyl group; where one of $R^{41}$ or $R^{42}$ is

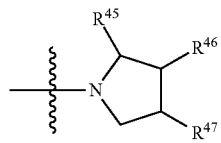

and the other is H or absent; $R^{43}$ and $R^{44}$ are each independently H or an unsubstituted alkyl group; one of $Y^5$, $Y^6$, and $Y^7$ is N while the remaining $Y^5$, $Y^6$, and $Y^7$ are not N; $R^{45}$, $R^{46}$, and $R^{47}$ are each independently H or an unsubstituted alkyl group; and $R^{36}$ and $R^{37}$ are each independently H.

In some embodiments of a compound of formula VII, $R^{31}$ is

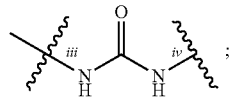

$R^{32}$ is an unsubstituted alkyl or cycloalkyl group; one of $R^{33}$, $R^{34}$, or $R^{35}$ is

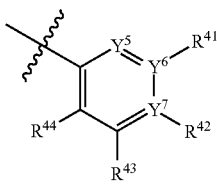

and the remaining $R^{33}$, $R^{34}$, or $R^{35}$ are each independently H or an unsubstituted alkyl group; where one of $R^{41}$ or $R^{42}$ is

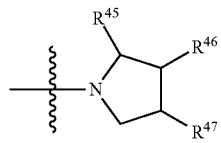

and the other is H or absent; $R^{43}$ and $R^{44}$ are each independently H or an unsubstituted alkyl group; one of $Y^5$, $Y^6$, and $Y^7$ is N while the remaining $Y^5$, $Y^6$, and $Y^7$ are not N; $R^{45}$, $R^{46}$, and $R^{47}$ are each independently H or an unsubstituted alkyl group; and $R^{36}$ and $R^{37}$ are each independently H.

In an aspect, a compound according to formula VIII is provided

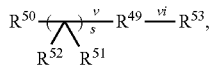

as well as stereoisomers thereof, tautomers thereof, solvates thereof, or pharmaceutically acceptable salts thereof; wherein v and vi designate the particular bonds indicated in formula VIII; $R^{49}$ is selected from formulas J, K, L, or M:

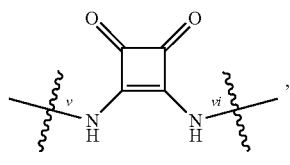

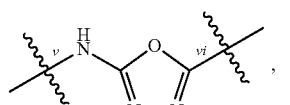

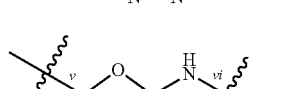

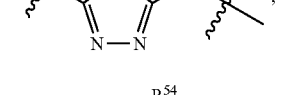

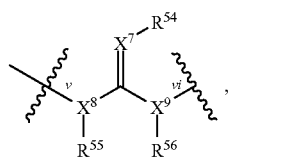

where $X^7$, $X^8$, and $X^9$ are each independently O, N, or S; $R^{54}$, $R^{55}$, and $R^{56}$ are each independently H, cyano, amino, or a substituted or unsubstituted alkyl, alkanoyl, alkanoyloxy, or aryl group when $X^7$, $X^8$, or $X^9$ are respectively N and are absent when $X^7$, $X^8$, or $X^9$ are respectively O or S; $R^{50}$ is a substituted or unsubstituted aryl or heteroaryl group; $R^{51}$ and $R^{52}$ are each independently H or a substituted or unsubstituted alkyl group, or $R^{51}$ and $R^{52}$ together form a 3- or 4-membered cycloalkyl ring; $R^{53}$ is a substituted aryl or heteroaryl group where at least one of the substituents is

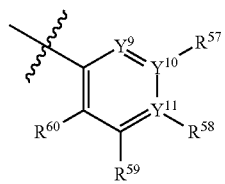

and the other substitutents, if present, are not; where one of $R^{57}$ or $R^{58}$ is

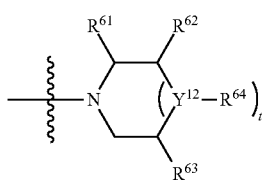

and the other is H, azido, trifluoromethyldiazirido, isocyano, isothiocyano, pentafluorosulfanyl, or a substituted or unsubstituted alkyl, alkanoyl, alkanoyloxy, aryloyl, or aryloyloxy group; $R^{59}$ and $R^{60}$ are each independently H, halo, azido, trifluoromethyldiazirido, isocyano, isothiocyano, pentafluorosulfuryl, or a substituted or unsubstituted alkyl, alkanoyl, alkanoyloxy, aryloyl, or aryloyloxy group; $Y^9$ is CH or N; $Y^{10}$ and $Y^{11}$ are each independently C or N, provided that when $Y^{10}$ or $Y^{11}$ is N then $R^{41}$ or $R^{42}$ respectively is absent; $Y^{12}$ is CH, N, O, S, S(O), or $S(O)_2$; $R^{61}$, $R^{62}$, and $R^{63}$ are each independently H, azido, trifluoromethyldiazirido, isocyano, isothiocyano, or a substituted or unsubstituted alkyl group; $R^{64}$ is H or a substituted or unsubstituted alkyl group when $Y^{12}$ is CH or N and is absent when $Y^{12}$ is O, S, S(O), or $S(O)_2$; t is 0 or 1; and s is 0 or 1.

In an aspect of the present technology, a composition is provided that includes any one of the aspects and embodiments of compounds of formulas I-VIIII and a pharmaceutically acceptable carrier.

In an aspect, a pharmaceutical composition for treating a condition is provided, the pharmaceutical composition including a therapeutically effective amount of the compound of any one of the aspects and embodiments of compounds of formulas I-VIIII; and where the condition is addiction, metabolic syndrome, obesity, or other CB1 receptor-mediated disorders.

In an aspect, a method is provided that includes administering a therapeutically effective amount of a compound of any one of the aspects and embodiments of compounds of formulas I-VIIII or administering a pharmaceutical composition comprising a therapeutically effective amount of a compound of any one of the aspects and embodiments of compounds of formulas I-VIIII to a subject suffering from addiction, metabolic syndrome, obesity, or other CB1 receptor-mediated disorders.

In an aspect, a method is provided where the method includes inhibiting β-arrestin in a subject by administering a therapeutically effective amount of a compound of any one of the aspects and embodiments of compounds of formulas I-VIIII. In some embodiments, the method includes inhibiting β-arrestin recruitment at least 10 times more than inhibiting cyclic AMP formation by administering the therapeutically effective amount of the compound. In any of these embodiments, the subject may be suffering from addiction, a metabolic disorder, obesity, or cancer. In any of these embodiments, the addiction is to at least one of nicotine, ethanol, cocaine, opiods, amphetamines, marijuana, or synthetic cannabinoid agonists.

In an aspect, a method for treating an addiction in a subject is provided that includes administering a therapeutically effective amount of a compound of any one of the aspects and embodiments of compounds of formulas I-VIII. In some embodiments, the addiction is to at least one of nicotine, ethanol, cocaine, opiods, amphetamines, marijuana, or synthetic cannabinoid agonists.

In an aspect, a method of inhibiting β-arrestin is provided that includes contacting a CB1 receptor with a compound of any one of the aspects and embodiments of compounds of formulas I-VIII. In such embodiments, it may be that β-arrestin recruitment is inhibited at least 10 times more than cyclic AMP formation in the contacting step.

DETAILED DESCRIPTION

Figure 1:
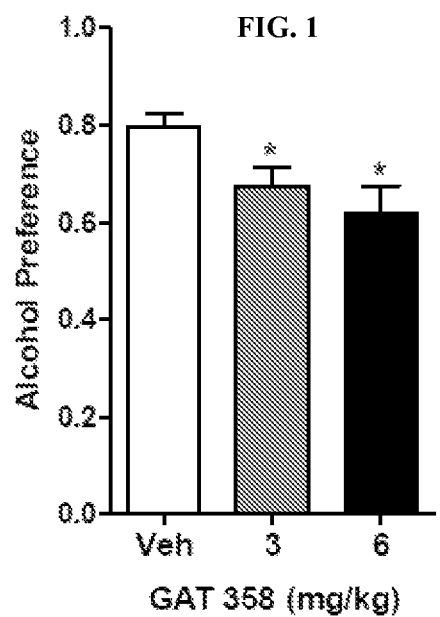
FIG. 1 shows the effects of GAT 358 at various dosages on the alcohol preference in mice, according to one embodiment.

In various aspects, the present technology provides novel compounds, compositions and methods to selectively modulate the cannabinoid 1 (CB1) receptor. The compounds provided herein can be formulated into pharmaceutical compositions and medicaments that are useful in the disclosed methods. Also provided is the use of the compounds in preparing pharmaceutical formulations and medicaments, the use of the compounds in treating addiction, metabolic syndrome, obesity, or other CB1 receptor-mediated disorders.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1] hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, among others. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to —C≡CH, —C≡CCH$_3$, —CH$_2$C≡CCH$_3$, —C≡CCH$_2$CH(CH$_2$CH$_3$)$_2$, among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Although the phrase "heteroaryl groups" includes fused ring compounds, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylate" as used herein refers to a —COOH group. A "substituted carboxylate" refers to a —C(O)O-G where G is a carboxylate protecting group. Carboxylate protecting groups are well known to one of ordinary skill in the art. An extensive list of protecting groups for the carboxylate group functionality may be found in Protective Groups in Organic Synthesis, Greene, T.W.; Wuts, P. G. M., John Wiley & Sons, New York, N.Y., (3rd Edition, 1999) which can be added or removed using the procedures set forth therein and which is hereby incorporated by reference in its entirety and for any and all purposes as if fully set forth herein.

The term "ester" as used herein refers to —COOR$^{70}$ groups. R$^{70}$ is a substituted or unsubstituted alkyl, cycloalkyl, alkenyl, alkynyl, aryl, aralkyl, heterocyclylalkyl or heterocyclyl group as defined herein.

The term "amide" (or "amido") includes C- and N-amide groups, i.e., —C(O)NR$^{71}$R$^{72}$, and —NR$^{71}$C(O)R$^{72}$ groups, respectively. R$^{71}$ and R$^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In some embodiments, the amide is —NR$^{71}$C(O)—(C$_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NR$^{73}$C(O)OR$^{74}$ and —OC(O)NR$^{73}$R$^{74}$ groups, respectively. R$^{73}$ and R$^{74}$ are independently a substituted or unsubstituted alkyl, alkenyl, alkynyl, cycloalkyl, aryl, aralkyl, heterocyclylalkyl, or heterocyclyl group as defined herein. R$^{73}$ may also be H.

The term "amine" (or "amino") as used herein refers to —NR$^{75}$R$^{76}$ groups, wherein R$^{75}$ and R$^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{78}$R$^{79}$ and —NR$^{78}$SO$_2$R$^{79}$ groups, respectively. R$^{78}$ and R$^{79}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "thiol" refers to —SH groups, while sulfides include —SR$^{80}$ groups, sulfoxides include —S(O)R$^{81}$ groups, sulfones include —SO$_2$R$^{82}$ groups, and sulfonyls include —SO$_2$OR$^{83}$. R$^{80}$, R$^{81}$, R$^{82}$, and R$^{83}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to —NR$^{84}$—C(O)—NR$^{85}$R$^{86}$ groups. R$^{84}$, R$^{85}$, and R$^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{87}$)NR$^{88}$R$^{89}$ and —NR$^{87}$C(NR$^{88}$)R$^{89}$, wherein R$^{87}$, R$^{88}$, and R$^{89}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{90}$C(NR$^{91}$)NR$^{92}$R$^{93}$, wherein R$^{90}$, R$^{91}$, R$^{92}$ and R$^{93}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{94}$)=C(R$^{95}$)NR$^{96}$R$^{97}$ and —NR$^{94}$C(R$^{95}$)=C(R$^{96}$)R$^{97}$, wherein R$^{94}$, R$^{95}$, R$^{96}$ and R$^{97}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxy" as used herein can refer to —OH or its ionized form, —O$^-$.

The term "imide" refers to —C(O)NR$^{98}$C(O)R$^{99}$, wherein R$^{98}$ and R$^{99}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{100}$(NR$^{101}$) and —N(CR$^{100}$R$^{101}$) groups, wherein R$^{100}$ and R$^{101}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{100}$ and R$^{101}$ are not both simultaneously hydrogen.

The term "nitro" as used herein refers to an —NO$_2$ group.

The term "trifluoromethyl" as used herein refers to —CF$_3$.

The term "trifluoromethoxy" as used herein refers to —OCF$_3$.

The term "azido" refers to —$N_3$.

The term "trialkyl ammonium" refers to a —$N(alkyl)_3$ group. A trialkylammonium group is positively charged and thus typically has an associated anion, such as halogen anion.

The term "trifluoromethyldiazirido" refers to

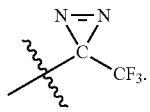 [SMILES: *C1(C(F)(F)F)N=N1]

The term "isocyano" refers to —NC.

The term "isothiocyano" refers to —NCS.

The term "pentafluorosulfanyl" refers to —$SF_5$.

The term "addictive substance" refers to those substances that when internalized can generate a compulsive desire and/or need for the addictive substance that is habit forming. Without being bound by theory, addictive substances activates the reward pathways of the brain of a subject in some manner, leading to a desire to repeat the internalization of the addictive substance. Exemplary addictive substances include, but are not limited to, nicotine, ethanol, cocaine, opiods, amphetamines, marijuana, and synthetic cannabinoid agonists.

The phrase "selectively inhibits" as used herein will be understood by persons of ordinary skill in the art and will vary to some extent depending upon the context in which the phrase is used. If there are uses of the phrase which are not clear to persons of ordinary skill in the art, given the context in which the phrase is used, the phrase at minimum refers to the compounds acting through a specific mechanism of action, resulting in fewer off-target effects because the compounds target a particular mechanism such as β-arrestin recruitment over other mechanisms such as cyclic AMP formation. The phrase may further be modified as discussed herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g. $Na^+$, $Li^+$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

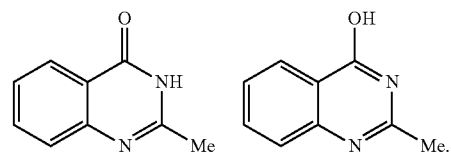

As another example, guanidines may exhibit the following isomeric forms in protic organic solution, also referred to as tautomers of each other:

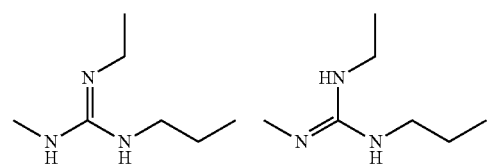

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Cannabinoid receptors are G protein-coupled receptors ("GPCRs"). Approximately 30% of Food and Drug Administration (FDA) approved small molecules are thought to target GPCRs. Synthetic ligands are known for only a fraction of the known GPCRs. Among the cannabinoid receptors, the cannabinoid 1 ("CB1") receptor subtype is the most abundant GPCR in the brain with high density in the cerebellum, hippocampus, and striatum. CB1 receptors are present in the various important parts of the brain and play an important role in rewards, learning, memory, motor control and addiction. In particular, pathological activity in these areas has been identified in the etiology of important disease states (e.g., obesity, metabolic syndrome, substance abuse, and neurodegenerative diseases) that present important medical problems worldwide. Many issues contribute to the challenges of discovering novel selective agonists or antagonists that bind at the orthosteric site of the receptor. Orthosteric sites for specific endogenous ligands across cannabinoid subtypes are often conserved, making it difficult to achieve high selectivity between members of the subfamily.

An alternative approach is the development of allosteric modulators of CB1 receptor. These ligands would bind to a site which is distinct from orthosteric site, commonly known as an "allosteric site," and potentiate or inhibit activation of receptor by its natural ligands. Allosteric sites in a given receptor or enzyme may be under less evolutionary pressure for their conservation between subtypes of the receptor/enzyme, thus protentially allowing for high subtype selectivity. This approach has been highly successful in case of the ligand-gated ion channels.

Allosteric modulators of the CB1 receptor would bind to the receptor at the site distinct to the orthosteric sites leading to the change in receptor conformation. As a result, interactive properties of the receptor with respect to orthosteric ligand(s) and cellular host environment can be modified in either a positive or negative direction, respectively referred to as positive allosteric modulators ("PAMs") and negative allosteric modulators ("NAMs"). Allosteric modulators can exhibit the following pharmacological properties: (i) affinity modulation, where the resulting conformation can alter either association or dissociation rate of on orthosleric ligand; (ii) efficacy modulation, where the allosteric effect can modify intracellular response and lead to a change in the signaling capacity of the orthosteric ligand; and/or (iii) agonism/inverse agonism, where the allosteric modulator can perturb receptor signaling in either a positive or negative direction, irrespective of presence of orthosteric modulator.

The present technology provides compounds, compositions, and methods for the negative allosteric modulation of CB1 receptor mediated pathways. Unlike CB1 receptor antagonists, the allosteric modulators of the present technology fine tune the downstream signaling and lack inverse agonism with respect to the CB1 receptor. Moreover, the present technology provides functionally selective compounds that do not completely block CB1 receptor mediated signaling and may show selectivity in modulating a particular type of signaling over other signaling performed by the CB1 receptor, thereby providing therapeutic benefits with minimum or no side effects. Thus, the compounds and compositions of the present technology are useful for the treatment of CB1 receptor mediated disorders without exhibiting the side effects known to accompany CB1 antagonist-related and CB1 inverse agonist-related treatments. For example, the present application provides data evidencing that the compounds of the present technology are useful in treating or in the prophylaxis of drug addiction, especially alcohol addiction, without exhibiting the side effects known to accompany CB1 receptor antagonist-related treatments. It is appreciated that the various modes of treatment can mean "substantial" treatment, which includes total but also less than total treatment, and in which some biologically or medically relevant result is achieved. Furthermore, treatment or treating can refer to therapeutic treatment and prophylactic or preventative measures in which the object is to prevent, slow down (lessen) a disease state, condition or malady. For example, a subject can be successfully treated for an addiction if, after receiving through administration an effective or therapeutic amount of one or more compounds described herein, the subject shows observable and/or measurable reduction in or absence of one or more signs and symptoms of the particular addiction. The present technology also provides for methods of administering one or more compounds of the present technology to a patient in an effective amount for the treatment of a CB1 receptor-mediated disorder including, but not limited to, addiction, metabolic syndrome, obesity, and other CB1 receptor-mediated disorders.

Thus, in an aspect of the present technology, a compound of formula I is provided

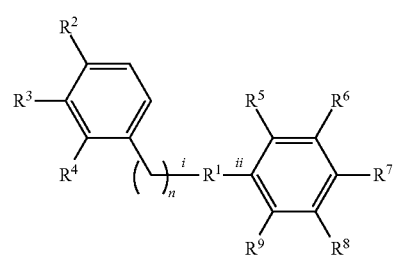

as well as stereoisomers thereof, tautomers thereof, solvates thereof, or pharmaceutically acceptable salts thereof; wherein i and ii designate the particular bonds indicated in formula I; R¹ is selected from formulas A, B, C, or D

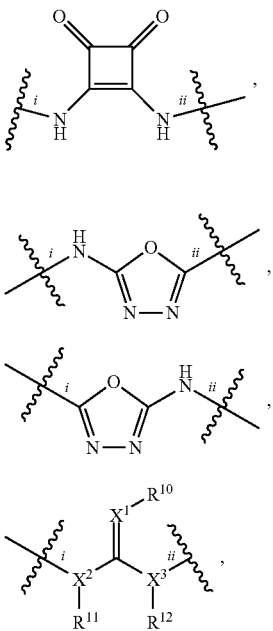

A

B

C

D

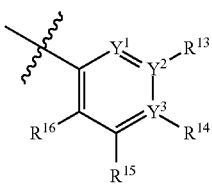

where $X^1$, $X^2$, and $X^3$ are each independently O, N, or S; and $R^{10}$, $R^{11}$, and $R^{12}$ are each independently H, cyano, amino, or a substituted or unsubstituted alkyl, alkanoyl, alkanoyloxy, or aryl group when $X^1$, $X^2$, or $X^3$ are respectively N and are absent when $X^1$, $X^2$, and $X^3$ are respectively O or S; or $R^{11}$ and $R^4$ together form a substituted or unsubstituted 5- or 6-membered heterocylyl ring; $R^2$, $R^3$, and $R^4$ are each independently H, halo, cyano, trifluoromethyl, nitro, trialkyl ammonium, azido, trifluoromethyldiazirido, isocyano, isothiocyano, pentafluorosulfanyl, or a substituted or unsubstituted alkyl, alkoxy, aryl, aryloxy, alkynyl, heterocyclylalkyl, alkanoyl, alkanoyloxy, aryloyl, aryloyloxy, carboxylate, or ester group, or where $R^2$ and $R^3$ or $R^3$ and $R^4$ form a substituted or unsubstituted 5- or 6-membered cycloalkyl, aryl, or heteroaryl ring, or $R^3$ and $R^4$ together form a substituted or unsubstituted 5- or 6-membered cycloalkyl, aryl, or heteroaryl ring; one of $R^5$, $R^6$, or $R^7$ is

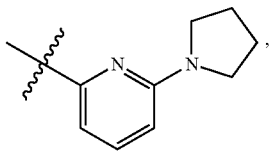

and the remaining $R^5$, $R^6$, or $R^7$ are each independently H, halo, azido, trifluoromethyldiazirido, isocyano, isothiocyano, or a substituted or unsubstituted alkyl, alkanoyl, alkanoyloxy, aryloyl, or aryloyloxy group; where one of $R^{13}$ or $R^{14}$ is

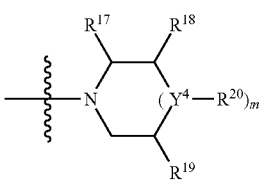

and the other is H, azido, trifluoromethyldiazirido, isocyano, isothiocyano, or a substituted or unsubstituted alkyl, alkanoyl, alkanoyloxy, aryloyl, or aryloyloxy group; $R^{15}$ and $R^{16}$ are each independently H, halo, azido, trifluoromethyldiazirido, isocyano, isothiocyano, or a substituted or unsubstituted alkyl, alkanoyl, alkanoyloxy, aryloyl, or aryloyloxy group; $Y^1$ is CH or N; $Y^2$ and $Y^3$ are each independently C or N, provided that when $Y^2$ or $Y^3$ is N then $R^{13}$ or $R^{14}$ respectively is absent; $Y^4$ is CH, N O, S, S(O), or S(O)$_2$; $R^{17}$, $R^{18}$, and $R^{19}$ are each independently H, azido, trifluoromethyldiazirido, isocyano, isothiocyano, or a substituted or unsubstituted alkyl group; $R^{20}$ is H or a substituted or unsubstituted alkyl group when $Y^4$ is CH or N and is absent when $Y^4$ is O, S, S(O), or S(O)$_2$; m is 0 or 1; $R^8$ and $R^9$ are each independently H or a substituted or unsubstituted alkyl group; and n is 0 or 1;

with the proviso that $R^2$ is not Cl when $R^1$ is formula D, $X^1$ is O, $X^2$ and $X^3$ are each N, $R^3$ and $R^4$ are each H, $R^5$, $R^7$, $R^8$, and $R^9$ are each H, $R^6$ is $R^{11}$ and $R^{12}$ are each H, and n is 0. In those embodiments where n is 0, it is understood that the position is a continuation of the covalent bond i. In some embodiments of a compound of formula I, at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group. In some embodiments of a compound of formula I, one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group, and the remaining $R^2$, $R^3$, and $R^4$ are not.

In some embodiments of a compound of formula I, two of $R^2$, $R^3$, and $R^4$ are each independently halo, cyano, trifluoromethyl, nitro, trialkyl ammonium, azido, trifluoromethyldiazirido, isocyano, isothiocyano, pentafluorosulfanyl, or a substituted or unsubstituted alkyl, alkoxy, aryl, aryloxy, alkynyl, heterocyclylalkyl, alkanoyl, alkanoyloxy, aryloyl, aryloyloxy, carboxylate, or ester group. In some embodiments of a compound of formula I, at least one of $R^2$, $R^3$, and $R^4$ is halo, cyano, trifluoromethyl, nitro, azido, trifluoromethyldiazirido, isocyano, isothiocyano, or a substituted or unsubstituted alkoxy, aryloxy, alkanoyl, alkanoyloxy, aryloyl, aryloyloxy, carboxylate, or ester group and at least one of the remaining $R^2$, $R^3$, and $R^4$ is a substituted or unsubstituted alkyl, aryl, or alkynyl group. In some embodiments of a compound of formula I, at least one of $R^2$, $R^3$, and $R^4$ is halo, cyano, trifluoromethyl, nitro, or a substituted or unsubstituted alkoxy, aryloxy, alkanoyl, alkanoyloxy, aryloyl, aryloyloxy, carboxylate, or ester group and at least one of the remaining $R^2$, $R^3$, and $R^4$ is a substituted or unsubstituted alkyl, aryl, or alkynyl group.

In embodiments where at least one of $R^2$, $R^3$, $R^4$, $R^5$, $R^6$, $R^7$, $R^{13}$, $R^{14}$, $R^{15}$, $R^{16}$, $R^{17}$, $R^{18}$, or $R^{19}$ is halo, azido, trifluoromethyldiazirido, isocyano, isothiocyano, or a substituted or unsubstituted alkoxy, aryloxy, alkanoyl, alkanoyloxy, aryloyl, aryloyloxy, carboxylate, or ester group, such a functional group may provide for a covalent bond within the allosteric binding site. By way of an illustrative example, isothiocyano-bearing compounds offer the advantage of high selectivity in reacting with amino- and sulfide-containing side chains suitably positioned in the allosteric active site because such groups are relatively slow to react with water and other hydroxyl groups. This irreversible binding not only permits analysis of the compound-receptor interaction, but also provides for an increased potency and longer duration of effect by the compound as compared to a similar compound that does not form a covalent bond. Such compounds that may provide for a covalent bond within the allosteric binding site are excellent for use in the treatment of chronic addiction. Thus, in some embodiments of a compound of formula I, one of $R^2$, $R^3$, $R^4$, $R^5$, $R^6$, $R^7$, $R^{13}$, $R^{14}$, $R^{15}$, $R^{16}$, $R^{17}$, $R^{18}$, or $R^{19}$ is azido, trifluoromethyldiazirido isocyano, or isothiocyano. In some embodiments of a compound of formula I, only one of $R^2$, $R^3$, $R^4$, $R^5$, $R^6$, $R^7$, $R^{13}$, $R^{14}$, $R^{15}$, $R^{16}$, $R^{17}$, $R^{18}$, or $R^{19}$ is azido, trifluoromethyldiazirido, isocyano or isothiocyano and the remaining $R^2$, $R^3$, $R^4$, $R^5$, $R^6$, $R^7$, $R^{13}$, $R^{14}$, $R^{15}$, $R^{16}$, $R^{17}$, $R^{18}$, and $R^{19}$ are not azido, trifluoromethyldiazirido, isocyano, or isothiocyano.

In some embodiments of a compound of formula I, $R^1$ is formula A, as represented by formula III

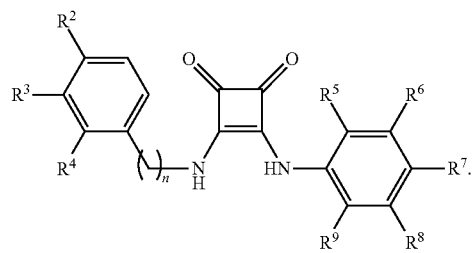

In some embodiments of a compound of formula III, one of $Y^1$, $Y^2$, and $Y^3$ is N while the remaining $Y^1$, $Y^2$, and $Y^3$ are not N. In some embodiments of formula I, at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group. In some embodiments of a compound of formula III, one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group, and the remaining $R^2$, $R^3$, and $R^4$ are not.

In any of the above embodiments of a compound of formula III, it may be that two of $R^2$, $R^3$, and $R^4$ are each independently halo, cyano, trifluoromethyl, nitro, trialkyl ammonium, azido, trifluoromethyldiazirido, isocyano, isothiocyano, or a substituted or unsubstituted alkyl, alkoxy, aryl, aryloxy, alkynyl, heterocyclylalkyl, alkanoyl, alkanoyloxy, aryloyl, aryloyloxy, carboxylate, or ester group. In any of the above embodiments of a compound of formula III, it may be that at least one of $R^2$, $R^3$, and $R^4$ is halo, cyano, trifluoromethyl, nitro, azido, trifluoromethyldiazirido, isocyano, isothiocyano, or a substituted or unsubstituted alkoxy, aryloxy, alkanoyl, alkanoyloxy, aryloyl, aryloyloxy, carboxylate, or ester group and at least one of the remaining $R^2$, $R^3$, and $R^4$ is a substituted or unsubstituted alkyl, aryl, or alkynyl group. In any of the above embodiments of a compound of formula III, it may be that at least one of $R^2$, $R^3$, and $R^4$ is halo, cyano, trifluoromethyl, nitro, or a substituted or unsubstituted alkoxy, arlyoxy, alkanoyl, alkanoyloxy, aryloyl, aryloyloxy, carboxylate, or ester group and at least one of the remaining $R^2$, $R^3$, and $R^4$ is a substituted or unsubstituted alkyl, aryl, or alkynyl group. In any of the above embodiments of a compound of formula III, it may be that one of $R^2$, $R^3$, $R^4$, $R^5$, $R^6$, $R^7$, $R^{13}$, $R^{14}$, $R^{15}$, $R^{16}$, $R^{17}$, $R^{18}$, or $R^{19}$ is azido, trifluoromethyldiazirido, isocyano, or isothiocyano. In any of the above embodiments of a compound of formula III, it may be that only one of $R^2$, $R^3$, $R^4$, $R^5$, $R^6$, $R^7$, $R^{13}$, $R^{14}$, $R^{15}$, $R^{16}$, $R^{17}$, $R^{18}$, or $R^{19}$ is azido, trifluoromethyldiazirido, isocyano, or isothiocyano and the remaining $R^2$, $R^3$, $R^4$, $R^5$, $R^6$, $R^7$, $R^{13}$, $R^{14}$, $R^{15}$, $R^{16}$, $R^{17}$, $R^{18}$, and $R^{19}$ are not azido, trifluoromethyldiazirido, isocyano, or isothiocyano.

In some embodiments of a compound of formula III, $R^2$, $R^3$, and $R^4$ are each independently H, halo, cyano, trifluoromethyl, nitro, trialkyl ammonium, or a substituted or unsubstituted alkyl, alkoxy, aryl, aryloxy, alkynyl, heterocyclylalkyl, alkanoyl, alkanoyloxy, aryloyl, aryloyloxy, carboxylate, or ester group; one of $R^5$, $R^6$, or $R^7$ is

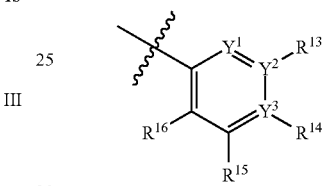

and the remaining $R^5$, $R^6$, or $R^7$ are each independently H, halo, or a substituted or unsubstituted alkyl, alkanoyl, alkanoyloxy, aryloyl, or aryloyloxy group; where one of $R^{13}$ or $R^{14}$ is

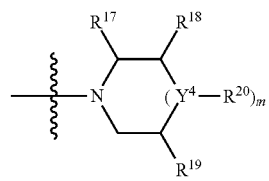

and the other is H, or a substituted or unsubstituted alkyl, alkanoyl, alkanoyloxy, aryloyl, or aryloyloxy group; $R^{15}$ and $R^{16}$ are each independently H, halo, or a substituted or unsubstituted alkyl, alkanoyl, alkanoyloxy, aryloyl, or aryloyloxy group; and $R^{17}$, $R^{18}$, and $R^{19}$ are each independently H, or a substituted or unsubstituted alkyl group. In some embodiments of a compound of formula III, at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group.

In some embodiments of a compound of formula III, $R^2$, $R^3$, and $R^4$ are each independently H, halo, cyano, trifluoromethyl, nitro, or a substituted or unsubstituted alkyl, alkoxy, aryl, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;

one of $R^5$, $R^6$, or $R^7$ is

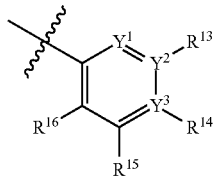

and the remaining $R^5$, $R^6$, or $R^7$ are each independently H or a substituted or unsubstituted alkyl, alkanoyl, alkanoyloxy, aryloyl, or aryloyloxy group; where one of $R^{13}$ or $R^{14}$ is

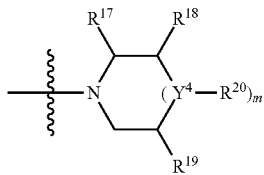

and the other is H or absent; $R^{15}$ and $R^{16}$ are each independently H or a substituted or unsubstituted alkyl, alkanoyl, alkanoyloxy, aryloyl, or aryloyloxy group; and $R^{17}$, $R^{18}$, and $R^{19}$ are each independently H, or a substituted or unsubstituted alkyl group.

In some embodiments of a compound of formula III, $R^2$, $R^3$, and $R^4$ are each independently H, halo, cyano, trifluoromethyl, nitro, or a substituted or unsubstituted alkyl, alkoxy, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;
one of $R^5$, $R^6$, or $R^7$ is

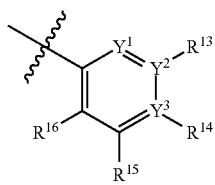

and the remaining $R^5$, $R^6$, or $R^7$ are each independently H or a substituted or unsubstituted alkyl group; where one of $R^{13}$ or $R^{14}$ is

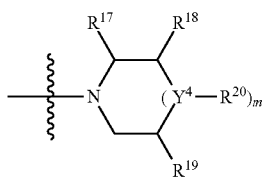

and the other is H or absent; $R^{15}$ and $R^{16}$ are each independently H or a substituted or unsubstituted alkyl group; and $R^{17}$, $R^{18}$, and $R^{19}$ are each independently H, or a substituted or unsubstituted alkyl group. In some embodiments of formula III, $R^2$, $R^3$, and $R^4$ are each independently H, halo, cyano, trifluoromethyl, nitro, or a substituted or unsubstituted alkyl, alkoxy, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;
one of $R^5$, $R^6$, or $R^7$ is

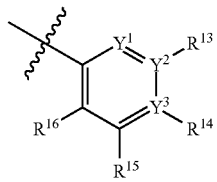

and the remaining $R^5$, $R^6$, or $R^7$ are each independently H or an unsubstituted alkyl group; where one of $R^{13}$ or $R^{14}$ is

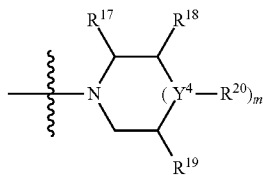

and the other is H or absent; $R^{15}$ and $R^{16}$ are each independently H or a substituted or unsubstituted alkyl group; $R^{17}$, $R^{18}$, and $R^{19}$ are each independently H or a substituted or unsubstituted alkyl group; $Y^4$ is CH, N, or O; $R^{20}$ is H or an unsubstituted alkyl group when $Y^4$ is CH or N and is absent when $Y^4$ is O; and $R^8$ and $R^9$ are each independently H.

In some embodiments of a compound of formula III, $R^2$, $R^3$, and $R^4$ are each independently H, halo, cyano, trifluoromethyl, nitro, or a substituted or unsubstituted alkyl, alkoxy, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;
one of $R^5$, $R^6$, or $R^7$ is

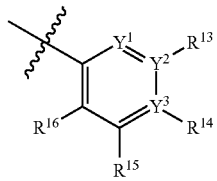

and the remaining $R^5$, $R^6$, or $R^7$ are each independently H or an unsubstituted alkyl group; where one of $R^{13}$ or $R^{14}$ is

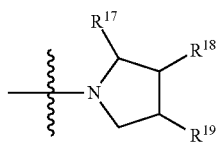

and the other is H or absent; $R^{15}$ and $R^{16}$ are each independently H or a substituted or unsubstituted alkyl group; $R^{17}$, $R^{18}$, and $R^{19}$ are each independently H or a substituted or unsubstituted alkyl group; and $R^8$ and $R^9$ are each independently H.

In some embodiments of a compound of formula III, $R^2$, $R^3$, and $R^4$ are each independently H, halo, cyano, trifluoromethyl, nitro, or a substituted or unsubstituted alkyl, alkoxy, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;

one of $R^5$, $R^6$, or $R^7$ is

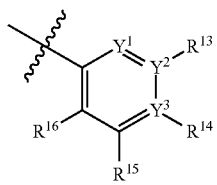

and the remaining $R^5$, $R^6$, or $R^7$ are each independently H or an unsubstituted alkyl group; where one of $R^{13}$ or $R^{14}$ is

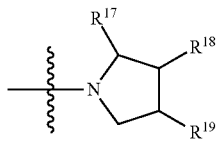

and the other is H or absent; $R^{15}$ and $R^{16}$ are each independently H or an unsubstituted alkyl group; one of $Y^1$, $Y^2$, and $Y^3$ is N while the remaining $Y^1$, $Y^2$, and $Y^3$ are not N; $R^{17}$, $R^{18}$, and $R^{19}$ are each independently H or an unsubstituted alkyl group; and $R^8$ and $R^9$ are each independently H.

In some embodiments of a compound of formula III, $R^2$, $R^3$, and $R^4$ are each independently H, halo, cyano, trifluoromethyl, nitro, or a substituted or unsubstituted alkyl, alkoxy, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;

one of $R^5$, $R^6$, or $R^7$ is

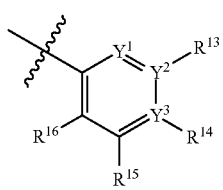

and the remaining $R^5$, $R^6$, or $R^7$ are each independently H; where one of $R^{13}$ or $R^{14}$ is

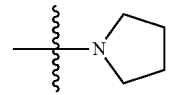 [SMILES: *N1CCCC1]

and the other is H or absent; $R^{15}$ and $R^{16}$ are each independently H or an unsubstituted alkyl group; one of $Y^1$, $Y^2$, and $Y^3$ is N while the remaining $Y^1$, $Y^2$, and $Y^3$ are not N; and $R^8$ and $R^9$ are each independently H.

In some embodiments of a compound of formula III, one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group, and the remaining $R^2$, $R^3$, and $R^4$ are each independently H;

one of $R^5$, $R^6$, or $R^7$ is

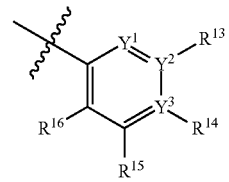

and the remaining $R^5$, $R^6$, or $R^7$ are each independently H; where one of $R^{13}$ or $R^{14}$ is

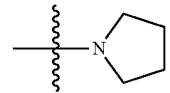 [SMILES: *N1CCCC1]

and the other is H or absent; $R^{15}$ and $R^{16}$ are each independently H or an unsubstituted alkyl group; one of $Y^1$, $Y^2$, and $Y^3$ is N while the remaining $Y^1$, $Y^2$, and $Y^3$ are not N; and $R^8$ and $R^9$ are each independently H.

In some embodiments of a compound of formula I, wherein $R^1$ is formula B as represented by formula IV, or $R^1$ is formula C as represented by formula V

IV

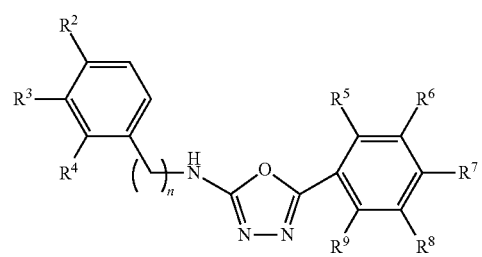

V

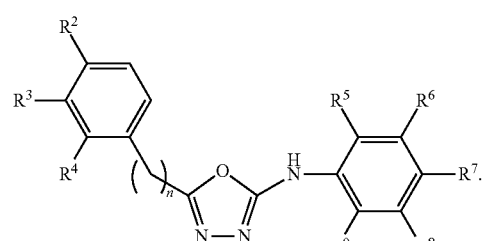

In some embodiments of a compound of formulas IV or V, one of $Y^1$, $Y^2$, and $Y^3$ is N while the remaining $Y^1$, $Y^2$, and $Y^3$ are not N. In some embodiments of formulas IV or V, at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group. In some embodiments of a compound of formulas IV or V, one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group, and the remaining $R^2$, $R^3$, and $R^4$ are not.

In any of the above embodiments of a compound of formulas IV or V, it may be that two of $R^2$, $R^3$, and $R^4$ are each independently halo, cyano, trifluoromethyl, nitro, trialkyl ammonium, azido, trifluoromethyldiazirido, isocyano, isothiocyano, or a substituted or unsubstituted alkyl, alkoxy, aryl, aryloxy, alkynyl, heterocyclylalkyl, alkanoyl, alkanoyloxy, aryloyl, aryloyloxy, carboxylate, or ester group. In any of the above embodiments of a compound of formulas IV or V, it may be that at least one of $R^2$, $R^3$, and $R^4$ is halo, cyano, trifluoromethyl, nitro, azido, trifluoromethyldiazirido, isocyano, isothiocyano, or a substituted or unsubstituted alkoxy, aryloxy, alkanoyl, alkanoyloxy, aryloyl, aryloyloxy, carboxylate, or ester group and at least one of the remaining $R^2$, $R^3$, and $R^4$ is a substituted or unsubstituted alkyl, aryl, or alkynyl group. In any of the above embodiments of a compound of formulas IV or V, it may be that at least one of $R^2$, $R^3$, and $R^4$ is halo, cyano, trifluoromethyl, nitro, or a substituted or unsubstituted alkoxy, aryloxy, alkanoyl, alkanoyloxy, aryloyl, aryloyloxy, carboxylate, or ester group and at least one of the remaining $R^2$, $R^3$, and $R^4$ is a substituted or unsubstituted alkyl, aryl, or alkynyl group. In any of the above embodiments of a compound of formulas IV or V, it may be that one of $R^2$, $R^3$, $R^4$, $R^5$, $R^6$, $R^7$, $R^{13}$, $R^{14}$, $R^{15}$, $R^{16}$, $R^{17}$, $R^{18}$, or $R^{19}$ is azido, trifluoromethyldiazirido, isocyano, or isothiocyano. In any of the above embodiments of a compound of formulas IV or V, it may be that only one of $R^2$, $R^3$, $R^4$, $R^5$, $R^6$, $R^7$, $R^{13}$, $R^{14}$, $R^{15}$, $R^{16}$, $R^{17}$, $R^{18}$, or $R^{19}$ is azido, trifluoromethyldiazirido, isocyano, or isothiocyano and the remaining $R^2$, $R^3$, $R^4$, $R^5$, $R^6$, $R^7$, $R^{13}$, $R^{14}$, $R^{15}$, $R^{16}$, $R^{17}$, $R^{18}$, and $R^{19}$ are not azido, trifluoromethyldiazirido, isocyano, or isothiocyano.

In some embodiments of a compound of formulas IV or V, $R^2$, $R^3$, and $R^4$ are each independently H, halo, cyano, trifluoromethyl, nitro, trialkyl ammonium, or a substituted or unsubstituted alkyl, alkoxy, aryl, aryloxy, alkynyl, heterocyclylalkyl, alkanoyl, alkanoyloxy, aryloyl, aryloyloxy, carboxylate, or ester group;

one of $R^5$, $R^6$, or $R^7$ is

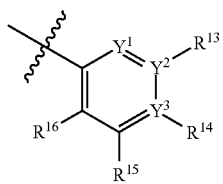

and the remaining $R^5$, $R^6$, or $R^7$ are each independently H, halo, or a substituted or unsubstituted alkyl, alkanoyl, alkanoyloxy, aryloyl, or aryloyloxy group; where one of $R^{13}$ or $R^{14}$ is

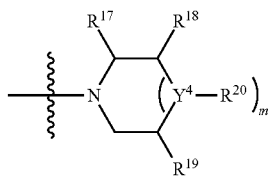

and the other is H, or a substituted or unsubstituted alkyl, alkanoyl, alkanoyloxy, aryloyl, or aryloyloxy group; $R^{15}$ and $R^{16}$ are each independently H, halo, or a substituted or unsubstituted alkyl, alkanoyl, alkanoyloxy, aryloyl, or aryloyloxy group; and $R^{17}$, $R^{18}$, and $R^{19}$ are each independently H or a substituted or unsubstituted alkyl group.

In some embodiments of a compound of formulas IV or V, $R^2$, $R^3$, and $R^4$ are each independently H, halo, cyano, trifluoromethyl, nitro, or a substituted or unsubstituted alkyl, alkoxy, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;

one of $R^5$, $R^6$, or $R^7$ is

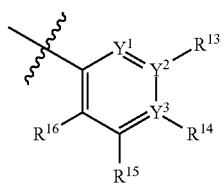

and the remaining $R^5$, $R^6$, or $R^7$ are each independently H or an unsubstituted alkyl group; where one of $R^{13}$ or $R^{14}$ is

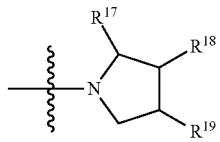

and the other is H or absent; $R^{15}$ and $R^{16}$ are each independently H or an unsubstituted alkyl group; one of $Y^1$, $Y^2$, and $Y^3$ is N while the remaining $Y^1$, $Y^2$, and $Y^3$ are not N; $R^{17}$, $R^{18}$, and $R^{19}$ are each independently H or an unsubstituted alkyl group; and $R^8$ and $R^9$ are each independently H.

In some embodiments of a compound of formulas IV or V, $R^2$, $R^3$, and $R^4$ are each independently H, halo, cyano, trifluoromethyl, nitro, or a substituted or unsubstituted alkyl, alkoxy, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;

one of $R^5$, $R^6$, or $R^7$ is

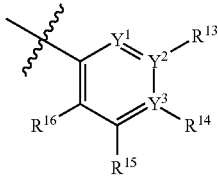

and the remaining $R^5$, $R^6$, or $R^7$ are each independently H; where one of $R^{13}$ or $R^{14}$ is

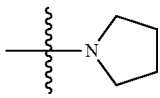 [SMILES: *N1CCCC1]

and the other is H or absent; $R^{15}$ and $R^{16}$ are each independently H or an unsubstituted alkyl group; one of $Y^1$, $Y^2$, and $Y^3$ is N while the remaining $Y^1$, $Y^2$, and $Y^3$ are not N; and $R^8$ and $R^9$ are each independently H.

In some embodiments of a compound of formulas IV or V, one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group, and the remaining $R^2$, $R^3$, and $R^4$ are each independently H;

one of $R^5$, $R^6$, or $R^7$ is

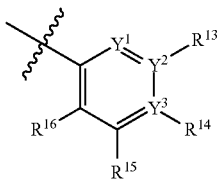

and the remaining $R^5$, $R^6$, or $R^7$ are each independently H; where one of $R^{13}$ or $R^{14}$ is

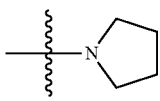

and the other is H or absent; $R^{15}$ and $R^{16}$ are each independently H or an unsubstituted alkyl group; one of $Y^1$, $Y^2$, and $Y^3$ is N while the remaining $Y^1$, $Y^2$, and $Y^3$ are not N; and $R^8$ and $R^9$ are each independently H.

In some embodiments of a compound of formula I, $R^1$ is formula D, as represented by formula VI

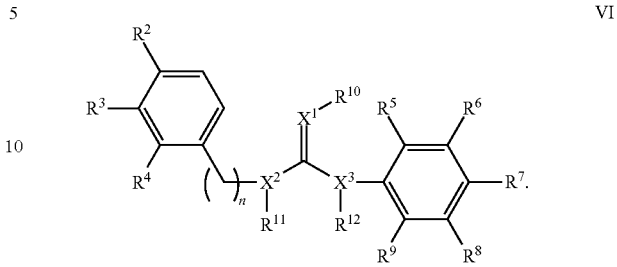

In some embodiments of a compound of formula VI, it may be that two of $R^2$, $R^3$, and $R^4$ are each independently halo, cyano, trifluoromethyl, nitro, trialkyl ammonium, azido, trifluoromethyldiazirido, isocyano, isothiocyano, or a substituted or unsubstituted alkyl, alkoxy, aryl, aryloxy, alkynyl, heterocyclylalkyl, alkanoyl, alkanoyloxy, aryloyl, aryloyloxy, carboxylate, or ester group. In any of the above embodiments of a compound of formula VI, it may be that at least one of $R^2$, $R^3$, and $R^4$ is halo, cyano, trifluoromethyl, nitro, azido, trifluoromethyldiazirido, isocyano, isothiocyano, or a substituted or unsubstituted alkoxy, aryloxy, alkanoyl, alkanoyloxy, aryloyl, aryloyloxy, carboxylate, or ester group and at least one of the remaining $R^2$, $R^3$, and $R^4$ is a substituted or unsubstituted alkyl, aryl, or alkynyl group. In any of the above embodiments of a compound of formula VI, it may be that at least one of $R^2$, $R^3$, and $R^4$ is halo, cyano, trifluoromethyl, nitro, or a substituted or unsubstituted alkoxy, aryloxy, alkanoyl, alkanoyloxy, aryloyl, aryloyloxy, carboxylate, or ester group and at least one of the remaining $R^2$, $R^3$, and $R^4$ is a substituted or unsubstituted alkyl, aryl, or alkynyl group. In any of the above embodiments of a compound of formula VI, it may be that one of $R^2$, $R^3$, $R^4$, $R^5$, $R^6$, $R^7$, $R^{13}$, $R^{14}$, $R^{15}$, $R^{16}$, $R^{17}$, $R^{18}$, or $R^{19}$ is azido, trifluoromethyldiazirido, isocyano, or isothiocyano. In any of the above embodiments of a compound of formula VI, it may be that only one of $R^2$, $R^3$, $R^4$, $R^5$, $R^6$, $R^7$, $R^{13}$, $R^{14}$, $R^{15}$, $R^{16}$, $R^{17}$, $R^{18}$, or $R^{19}$ is azido, trifluoromethyldiazirido, isocyano, or isothiocyano and the remaining $R^2$, $R^3$, $R^4$, $R^5$, $R^6$, $R^7$, $R^{13}$, $R^{14}$, $R^{15}$, $R^{16}$, $R^{17}$, $R^{18}$, and $R^{19}$ are not azido, trifluoromethyldiazirido, isocyano, or isothiocyano.

In some embodiments of a compound of formula VI, at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group. In some embodiments of a compound of formula VI, one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group, and the remaining $R^2$, $R^3$, and $R^4$ are not. In some embodiments of a compound of formula VI, $R^2$, $R^3$, and $R^4$ are each independently H, halo, cyano, trifluoromethyl, nitro, trialkyl ammonium, or a substituted or unsubstituted alkyl, alkoxy, aryl, aryloxy, alkynyl, heterocyclylalkyl, alkanoyl, alkanoyloxy, aryloyl, aryloyloxy, carboxylate, or ester group;

one of $R^5$, $R^6$, or $R^7$ is

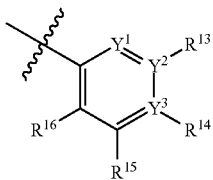

and the remaining $R^5$, $R^6$, or $R^7$ are each independently H, halo, or a substituted or unsubstituted alkyl, alkanoyl, alkanoyloxy, aryloyl, or aryloyloxy group; where one of $R^{13}$ or $R^{14}$ is

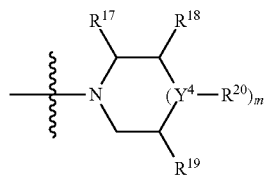

and the other is H, or a substituted or unsubstituted alkyl, alkanoyl, alkanoyloxy, aryloyl, or aryloyloxy group; and $R^{15}$ and $R^{16}$ are each independently H, halo, or a substituted or unsubstituted alkyl, alkanoyl, alkanoyloxy, aryloyl, or aryloyloxy group.

In some embodiments of a compound of formula VI, $R^2$, $R^3$, and $R^4$ are each independently H, halo, cyano, trifluoromethyl, nitro, or a substituted or unsubstituted alkyl, alkoxy, aryl, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;

one of $R^5$, $R^6$, or $R^7$ is

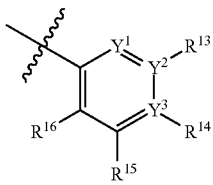

and the remaining $R^5$, $R^6$, or $R^7$ are each independently H or a substituted or unsubstituted alkyl, alkanoyl, alkanoyloxy, aryloyl, or aryloyloxy group; where one of $R^{13}$ or $R^{14}$ is

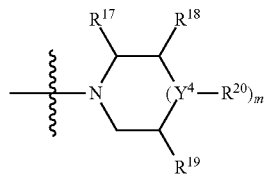

and the other is H or absent; $R^{15}$ and $R^{16}$ are each independently H or a substituted or unsubstituted alkyl, alkanoyl, alkanoyloxy, aryloyl, or aryloyloxy group; and $R^{17}$, $R^{18}$, and $R^{19}$ are each independently H or a substituted or unsubstituted alkyl group.

In some embodiments of a compound of formula VI, $R^2$, $R^3$, and $R^4$ are each independently H, halo, cyano, trifluoromethyl, nitro, or a substituted or unsubstituted alkyl, alkoxy, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;

one of $R^5$, $R^6$, or $R^7$ is

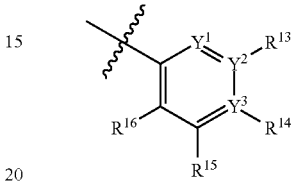

and the remaining $R^5$, $R^6$, or $R^7$ are each independently H or a substituted or unsubstituted alkyl group; where one of $R^{13}$ or $R^{14}$ is

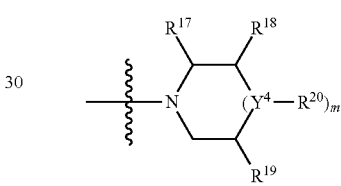

and the other is H or absent; $R^{15}$ and $R^{16}$ are each independently H or a substituted or unsubstituted alkyl group; and $R^{17}$, $R^{18}$, and $R^{19}$ are each independently H or a substituted or unsubstituted alkyl group.

In some embodiments of a compound of formula VI, $R^2$, $R^3$, and $R^4$ are each independently H, halo, cyano, trifluoromethyl, nitro, or a substituted or unsubstituted alkyl, alkoxy, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;

one of $R^5$, $R^6$, or $R^7$ is

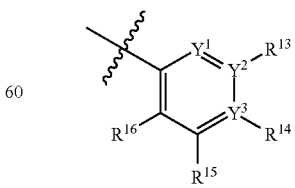

and the remaining $R^5$, $R^6$, or $R^7$ are each independently H or an unsubstituted alkyl group; where one of $R^{13}$ or $R^{14}$ is

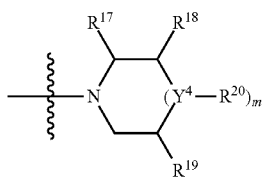

and the other is H or absent; $R^{15}$ and $R^{16}$ are each independently H or a substituted or unsubstituted alkyl group; $R^{17}$, $R^{18}$, and $R^{19}$ are each independently H or a substituted or unsubstituted alkyl group; $Y^4$ is CH, N, or O; $R^{20}$ is H or an unsubstituted alkyl group when $Y^4$ is CH or N and is absent when $Y^4$ is O; and $R^8$ and $R^9$ are each independently H.

In some embodiments of a compound of formula VI, $R^2$, $R^3$, and $R^4$ are each independently H, halo, cyano, trifluoromethyl, nitro, or a substituted or unsubstituted alkyl, alkoxy, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;

one of $R^5$, $R^6$, or $R^7$ is

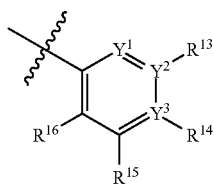

and the remaining $R^5$, $R^6$, or $R^7$ are each independently H or an unsubstituted alkyl group; where one of $R^{13}$ or $R^{14}$ is

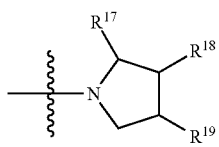

and the other is H or absent; $R^{15}$ and $R^{16}$ are each independently H or a substituted or unsubstituted alkyl group; $R^{17}$, $R^{18}$, and $R^{19}$ are each independently H, or a substituted or unsubstituted alkyl group; and $R^8$ and $R^9$ are each independently H.

In some embodiments of a compound of formula VI, $R^2$, $R^3$, and $R^4$ are each independently H, halo, cyano, trifluoromethyl, nitro, or a substituted or unsubstituted alkyl, alkoxy, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;

one of $R^5$, $R^6$, or $R^7$ is

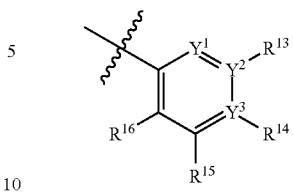

and the remaining $R^5$, $R^6$, or $R^7$ are each independently H or an unsubstituted alkyl group; where one of $R^{13}$ or $R^{14}$ is

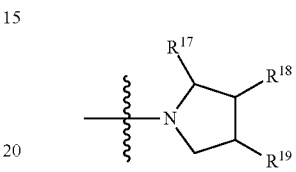

and the other is H or absent; $R^{15}$ and $R^{16}$ are each independently H or an unsubstituted alkyl group; one of $Y^1$, $Y^2$, and $Y^3$ is N while the remaining $Y^1$, $Y^2$, and $Y^3$ are not N; $R^{17}$, $R^{18}$, and $R^{19}$ are each independently H or an unsubstituted alkyl group; and $R^8$ and $R^9$ are each independently H.

In some embodiments of a compound of formula VI, $R^2$, $R^3$, and $R^4$ are each independently H, halo, cyano, trifluoromethyl, nitro, or a substituted or unsubstituted alkyl, alkoxy, aryloxy, alkynyl, heterocyclylalkyl, alkanoyl, alkanoyloxy, aryloyl, aryloyloxy, carboxylate, or ester group, wherein at least one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group;

one of $R^5$, $R^6$, or $R^7$ is

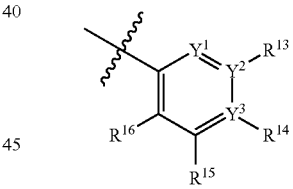

and the remaining $R^5$, $R^6$, or $R^7$ are each independently H; where one of $R^{13}$ or $R^{14}$ is

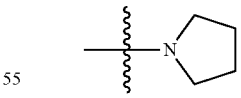

and the other is H or absent; $R^{15}$ and $R^{16}$ are each independently H or an unsubstituted alkyl group; one of $Y^1$, $Y^2$, and $Y^3$ is N while the remaining $Y^1$, $Y^2$, and $Y^3$ are not N; and $R^8$ and $R^9$ are each independently H.

In some embodiments of a compound of formula VI, one of $R^2$, $R^3$, or $R^4$ is halo, cyano, trifluoromethyl, nitro, or a substituted or unsubstituted alkoxy, aryloxy, alkynyl, alkanoyl, alkanoyloxy, aryloyl, aryloyloxy, carboxylate, or ester group, and the remaining $R^2$, $R^3$, and $R^4$ are each independently H;

one of $R^5$, $R^6$, or $R^7$ is

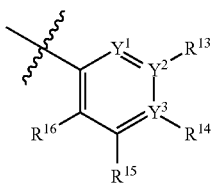

and the remaining $R^5$, $R^6$, or $R^7$ are each independently H; where one of $R^{13}$ or $R^{14}$ is

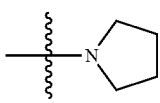 [SMILES: *N1CCCC1]

and the other is H or absent; $R^{15}$ and $R^{16}$ are each independently H or an unsubstituted alkyl group; one of $Y^1$, $Y^2$, and $Y^3$ is N while the remaining $Y^1$, $Y^2$, and $Y^3$ are not N; and $R^8$ and $R^9$ are each independently H.

In any of the above aspects and embodiments of compounds of formulas I, III, IV, V, or VI, it may be that $R^2$ is not halo when $R^1$ is formula D, $X^1$ is O, $X^2$ and $X^3$ are N, $R^3$ and $R^4$ are H, $R^5$, $R^7$, $R^8$, and $R^9$ are H, $R^6$ is

$R^{11}$ and $R^{12}$ are H, and n is 0.

In an aspect, a compound of formula II is provided

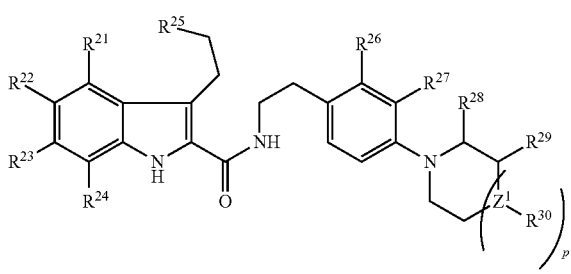

as well as stereoisomers thereof, tautomers thereof, solvates thereof, or pharmaceutically acceptable salts thereof; where $R^{21}$, $R^{22}$, $R^{23}$, $R^{24}$, $R^{25}$, $R^{26}$, $R^{27}$, $R^{28}$, and $R^{29}$ are each independently H, halo, cyano, trifluoromethyl, nitro, trialkyl ammonium, azido, trifluoromethyldiazirido, isocyano, isothiocyano, pentafluorosulfanyl, or a substituted or unsubstituted alkyl, alkoxy, aryl, aryloxy, alkynyl, heterocyclylalkyl, alkanoyl, alkanoyloxy, aryloyl, aryloyloxy, carboxylate, or ester group, provided that at least one of $R^{21}$, $R^{22}$, $R^{23}$, or $R^{24}$ is halo, cyano, trifluoromethyl, nitro, trialkyl ammonium, azido, trifluoromethyldiazirido, isocyano, isothiocyano, or a substituted or unsubstituted alkoxy, aryloxy, alkanoyl, alkanoyloxy, aryloyl, aryloyloxy, carboxylate, or ester group; $Z^1$ is CH, N, O, S, S(O), or S(O)$_2$; $R^{30}$ is H, halo, cyano, trifluoromethyl, nitro, trialkyl ammonium, azido, trifluoromethyldiazirido, isocyano, isothiocyano, or a substituted or unsubstituted alkyl, alkoxy, aryl, aryloxy, alkynyl, heterocyclylalkyl, alkanoyl, alkanoyloxy, aryloyl, aryloyloxy, carboxylate, or ester group, provided that $R^{30}$ is absent when $Z^1$ is O, S, S(O), or S(O)$_2$; p is 0 or 1;

with the proviso that $R^{22}$ is not Cl when p is 1, $R^{21}$, $R^{23}$, $R^{24}$, $R^{26}$, $R^{27}$, $R^{28}$, $R^{29}$, and $R^{30}$ are each H, $R^{25}$ is H or unsubstituted alkyl, and $Z^1$ is CH. In some embodiments of a compound of formula II, $R^{21}$, $R^{22}$, $R^{23}$, $R^{24}$, $R^{25}$, $R^{26}$, $R^{27}$, $R^{28}$, and $R^{29}$ are each independently H, halo, cyano, trifluoromethyl, nitro, azido, trifluoromethyldiazirido, isocyano, isothiocyano, or a substituted or unsubstituted alkyl, alkoxy, aryl, aryloxy, alkynyl, heterocyclylalkyl, alkanoyl, alkanoyloxy, aryloyl, aryloyloxy, carboxylate, or ester group, provided that at least one of $R^{21}$, $R^{22}$, $R^{23}$, or $R^{24}$ is halo, cyano, trifluoromethyl, nitro, azido, trifluoromethyldiazirido, isocyano, isothiocyano, or a substituted or unsubstituted alkoxy, aryloxy, alkanoyl, alkanoyloxy, aryloyl, aryloyloxy, carboxylate, or ester group; and $R^{30}$ is H, halo, cyano, trifluoromethyl, nitro, azido, trifluoromethyldiazirido, isocyano, isothiocyano, or a substituted or unsubstituted alkyl, alkoxy, aryl, aryloxy, alkynyl, heterocyclylalkyl, alkanoyl, alkanoyloxy, aryloyl, aryloyloxy, carboxylate, or ester group, provided that $R^{30}$ is absent when $Z^1$ is O, S, S(O), or S(O)$_2$.

In some embodiments of a compound of formula II, at least one of $R^{21}$, $R^{22}$, $R^{23}$, $R^{24}$, $R^{25}$, $R^{26}$, $R^{27}$, $R^{28}$, $R^{29}$ or $R^{30}$ is azido, trifluoromethyldiazirido, isocyano, or isothiocyano. In any of the embodiments of a compound of formula II, it may be that $R^{20}$ is not halo when p is 1, $R^{21}$, $R^{23}$, $R^{24}$, $R^{25}$, $R^{26}$, $R^{27}$, $R^{28}$, $R^{29}$, and $R^{30}$ are each H, and $Z^1$ is CH. In any of the embodiments of a compound of formula II, it may be that $R^{20}$ is not halo when p is 1, $R^{21}$, $R^{23}$, $R^{24}$, $R^{26}$, $R^{27}$, $R^{28}$, $R^{29}$, and $R^{30}$ are each H, $R^{25}$ is H or unsubstituted alkyl, and $Z^1$ is CH.

In an aspect, a compound according to formula VII is provided

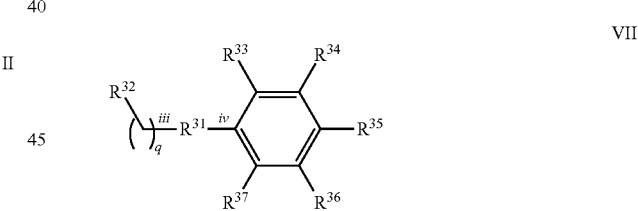

as well as stereoisomers thereof, tautomers thereof, solvates thereof, or pharmaceutically acceptable salts thereof; where iii and iv designate the particular bonds indicated in formula VII; $R^{31}$ is selected from formulas E, F, G, or H

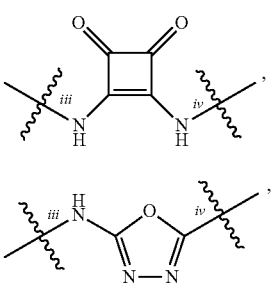

-continued

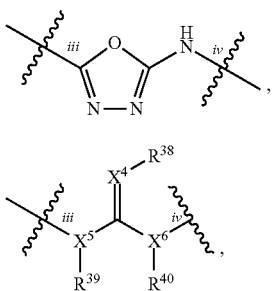

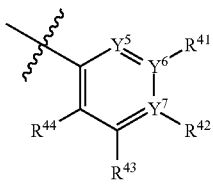

where $X^4$, $X^5$, and $X^6$ are each independently O, N, or S; $R^{38}$, $R^{39}$, and $R^{40}$ are each independently H, cyano, amino, or a substituted or unsubstituted alkyl, alkanoyl, alkanoyloxy, or aryl group when $X^4$, $X^5$, or $X^6$ are respectively N and are absent when $X^4$, $X^5$, and $X^6$ are respectively O or S; $R^{32}$ is H or an unsubstituted alkyl, cycloalkyl, or heterocylyl group;
one of $R^{33}$, $R^{34}$, or $R^{35}$ is

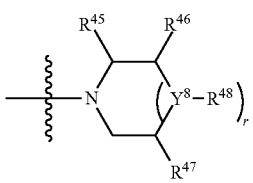

and the remaining $R^{33}$, $R^{34}$, or $R^{35}$ are each independently H, halo, azido, trifluoromethyldiazirido, isocyano, isothiocyano, or a substituted or unsubstituted alkyl, alkanoyl, alkanoyloxy, aryloyl, or aryloyloxy group; where one of $R^{41}$ or $R^{42}$ is

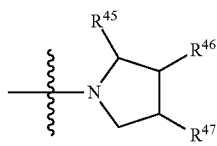

and the other is H, azido, trifluoromethyldiazirido, isocyano, isothiocyano, or a substituted or unsubstituted alkyl, alkanoyl, alkanoyloxy, aryloyl, or aryloyloxy group; $R^{43}$ and $R^{44}$ are each independently H, halo, azido, trifluoromethyldiazirido, isocyano, isothiocyano, or a substituted or unsubstituted alkyl, alkanoyl, alkanoyloxy, aryloyl, or aryloyloxy group; $Y^5$ is CH or N; $Y^6$ and $Y^7$ are each independently C or N, provided that when $Y^6$ or $Y^7$ is N then $R^{41}$ or $R^{42}$ respectively is absent; $Y^8$ is CH, N, O, S, S(O), or S(O)$_2$; $R^{45}$, $R^{46}$, and $R^{47}$ are each independently H, azido, trifluoromethyldiazirido, isocyano, isothiocyano, or a substituted or unsubstituted alkyl group; $R^{48}$ is H or a substituted or unsubstituted alkyl group when $Y^8$ is CH or N and is absent when $Y^8$ is O, S, S(O), or S(O)$_2$; r is 0 or 1; $R^{36}$ and $R^{37}$ are each independently H or a substituted or unsubstituted alkyl group; and q is 0 or 1. In embodiments where q is 0, it is understood that the position is a continuation of the covalent bond iii.

In some embodiments of a compound of formula VII, one of $R^{33}$, $R^{34}$, or $R^{35}$ is

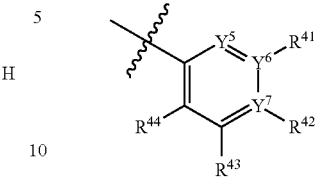

and the remaining $R^{33}$, $R^{34}$, or $R^{35}$ are each independently H or an unsubstituted alkyl group; where one of $R^{41}$ or $R^{42}$ is

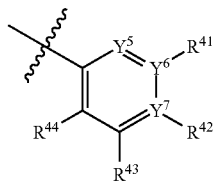

and the other is H or absent; $R^{43}$ and $R^{44}$ are each independently H or an unsubstituted alkyl group; one of $Y^5$, $Y^6$, and $Y^7$ is N while the remaining $Y^5$, $Y^6$, and $Y^7$ are not N; $R^{45}$, $R^{46}$, and $R^{47}$ are each independently H or an unsubstituted alkyl group; and $R^{36}$ and $R^{37}$ are each independently H. In some embodiments of a compound of formula VII, $R^{31}$ is formula H; one of $R^{33}$, $R^{34}$, or $R^{35}$ is

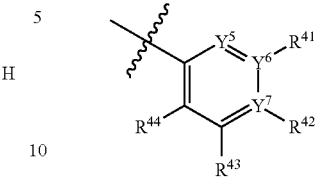

and the remaining $R^{33}$, $R^{34}$, or $R^{35}$ are each independently H or an unsubstituted alkyl group; where one of $R^{41}$ or $R^{42}$ is

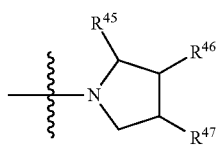

and the other is H or absent; $R^{43}$ and $R^{44}$ are each independently H or an unsubstituted alkyl group; one of $Y^5$, $Y^6$, and $Y^7$ is N while the remaining $Y^5$, $Y^6$, and $Y^7$ are not N; $R^{45}$, $R^{46}$, and $R^{47}$ are each independently H or an unsubstituted alkyl group; and $R^{36}$ and $R^{37}$ are each independently H.

In some embodiments of a compound of formula VII, $R^{31}$ is

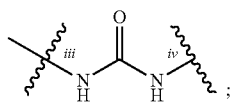

$R^{32}$ is an unsubstituted alkyl or cycloalkyl group; one of $R^{33}$, $R^{34}$, or $R^{35}$ is

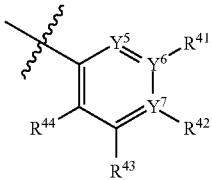

and the remaining $R^{33}$, $R^{34}$, or $R^{35}$ are each independently H or an unsubstituted alkyl group; where one of $R^{41}$ or $R^{42}$ is

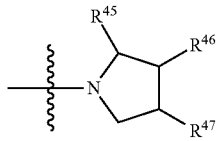

and the other is H or absent; $R^{43}$ and $R^{44}$ are each independently H or an unsubstituted alkyl group; one of $Y^5$, $Y^6$, and $Y^7$ is N while the remaining $Y^5$, $Y^6$, and $Y^7$ are not N; $R^{45}$, $R^{46}$, and $R^{47}$ are each independently H or an unsubstituted alkyl group; and $R^{36}$ and $R^{37}$ are each independently H.

In an aspect, a compound according to formula VIII is provided

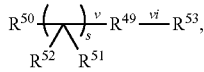
VIII as well as stereoisomers thereof, tautomers thereof, solvates thereof, or pharmaceutically acceptable salts thereof; wherein v and vi designate the particular bonds indicated in formula VIII; $R^{49}$ is selected from formulas J, K, L, or M:

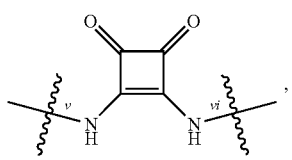
J

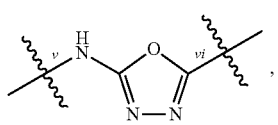
K

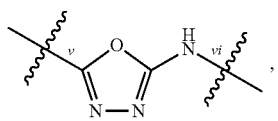
L

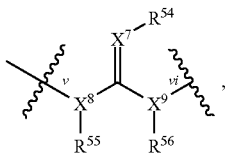
M where $X^7$, $X^8$, and $X^9$ are each independently O, N, or S; $R^{54}$, $R^{55}$, and $R^{56}$ are each independently H, cyano, amino, or a substituted or unsubstituted alkyl, alkanoyl, alkanoyloxy, or aryl group when $X^7$, $X^8$, or $X^9$ are respectively N and are absent when $X^7$, $X^8$, or $X^9$ are respectively O or S; $R^{50}$ is a substituted or unsubstituted aryl or heteroaryl group; $R^{51}$ and $R^{52}$ are each independently H or a substituted or unsubstituted alkyl group, or $R^{51}$ and $R^{52}$ together form a 3- or 4-membered cycloalkyl ring; $R^{53}$ is a substituted aryl or heteroaryl group where at least one of the substituents is

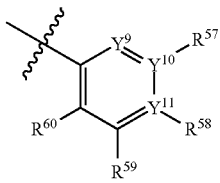

and the other substitutents, if present, are not; where one of $R^{57}$ or $R^{58}$ is

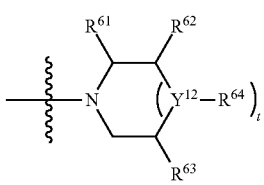

and the other is H, azido, trifluoromethyldiazirido, isocyano, isothiocyano, pentafluorosulfanyl, or a substituted or unsubstituted alkyl, alkanoyl, alkanoyloxy, aryloyl, or aryloyloxy group; $R^{59}$ and $R^{60}$ are each independently H, halo, azido, trifluoromethyldiazirido, isocyano, isothiocyano, pentafluorosulfuryl, or a substituted or unsubstituted alkyl, alkanoyl, alkanoyloxy, aryloyl, or aryloyloxy group; $Y^9$ is CH or N; $Y^{10}$ and $Y^{11}$ are each independently C or N, provided that when $Y^{10}$ or $Y^{11}$ is N then $R^{41}$ or $R^{42}$ respectively is absent; $Y^{12}$ is CH, N, O, S, S(O), or S(O)$_2$; $R^{61}$, $R^{62}$ and $R^{63}$ are each independently H, azido, trifluoromethyldiazirido, isocyano, isothiocyano, or a substituted or unsubstituted alkyl group; $R^{64}$ is H or a substituted or unsubstituted alkyl group when $Y^{12}$ is CH or N and is absent when $Y^{12}$ is O, S, S(O), or S(O)$_2$; t is 0 or 1; and s is 0 or 1. In embodiments where s is 0, it is understood that the position is a continuation of the covalent bond v.

In an aspect of the present technology, a composition is provided that includes any one of the aspects and embodiments of compounds of formulas I-VIII and a pharmaceutically acceptable carrier. In a related aspect, a pharmaceutical composition for treating a condition is provided, the pharmaceutical composition including a therapeutically effective amount of the compound of any one of the aspects and embodiments of compounds of formulas I-VIII; and where the condition is, addiction, metabolic syndrome, obesity, or other CB1 receptor-mediated disorders. In a further related aspect, a method is provided that includes administering a therapeutically effective amount of a compound of any one of the aspects and embodiments of compounds of formulas I-VIII or administering a pharmaceutical composition comprising a therapeutically effective amount of a compound of any one of the aspects and embodiments of compounds of formulas I-VIII to a subject suffering from, addiction, metabolic syndrome, obesity, or other CB1 receptor-mediated disorders.

"Effective amount" refers to the amount of a compound or composition required to produce a desired effect. One example of an effective amount includes amounts or dosages that yield acceptable toxicity and bioavailability levels for therapeutic (pharmaceutical) use including, but not limited to, the treatment of alcohol addiction. Another example of an effective amount includes amounts or dosages that are capable of reducing symptoms associated with metabolic syndrome, such as, for example, obesity and/or cardiometabolic abnormalities. In some embodiments, the effective amount of the compound selectively inhibits β-arrestin recruitment. In some embodiments, the effective amount of the compound selectively inhibits β-arrestin recruitment at least 5 times more than inhibiting cyclic AMP formation. In some embodiments, the effective amount of the compound selectively inhibits β-arrestin recruitment at least 10 times more than inhibiting cyclic AMP formation. As used herein, a "subject" or "patient" is a mammal, such as a cat, dog, rodent or primate. Typically the subject is a human, and, preferably, a human suffering from or suspected of suffering from an addiction. The term "subject" and "patient" can be used interchangeably.

Thus, the instant present technology provides pharmaceutical compositions and medicaments comprising any of the compounds disclosed herein (e.g., compounds of formulas I-VIII) and a pharmaceutically acceptable carrier or one or more excipients or fillers. The compositions may be used in the methods and treatments described herein. Such compositions include a β-arrestin inhibitory effective amount of any compound as described herein, including but not limited to a compound of formulas I-VIII. In some embodiments, the pharmaceutical composition is packaged in unit dosage form. The unit dosage form is effective in treating addiction by reducing desire for an addictive substance(s), and/or effective in treating a metabolic disorder by reducing symptoms associated with the metabolic disorder when administered to a subject in need thereof.

The pharmaceutical compositions may be prepared by mixing one or more compounds of the present technology, pharmaceutically acceptable salts thereof, stereoisomers thereof, tautomers thereof, or solvates thereof, with pharmaceutically acceptable carriers, excipients, binders, diluents or the like to prevent and treat disorders associated with the effects of increased plasma and/or hepatic lipid levels. The compounds and compositions described herein may be used to prepare formulations and medicaments that prevent or treat a variety of disorders associated with, addiction, metabolic syndrome, obesity, and/or other CB1 receptor-mediated disorders. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections.

The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of compounds of the present technology by inhalation.

Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Those skilled in the art are readily able to determine an effective amount by simply administering a compound of the present technology to a patient in increasing amounts until (for addiction) the motivation to internalize the addictive substance and/or relapse-like behavior is decreased or stopped, or (for metabolic syndrome and/or obesity) the elevated plasma or elevated white blood cell count or hepatic cholesterol or triglycerides or progression of the disease state is decreased or stopped. For metabolic syndrome and/or obesity, the progression of the disease state can be assessed using in vivo imaging, as described, or by taking a tissue sample from a patient and observing the target of interest therein. The compounds of the present technology can be administered to a patient at dosage levels in the range of about 0.1 to about 1,000 mg per day. For a normal human adult having a body weight of about 70 kg, a dosage in the range of about 0.01 to about 100 mg per kg of body weight per day is sufficient. The specific dosage used, however, can vary or may be adjusted as considered appropriate by those of ordinary skill in the art. For example, the dosage can depend on a number of factors including the requirements of the patient, the severity of the condition being treated and the pharmacological activity of the compound being used. The determination of optimum dosages for a particular patient is well known to those skilled in the art.

Various assays and model systems can be readily employed to determine the therapeutic effectiveness of the viral treatment according to the present technology.

Effectiveness of the compositions and methods of the present technology may also be demonstrated by a decrease in the symptoms of an addiction, such as, for example, motivation to internalize the addictive substance and/or relapse-like behavior. Effectiveness of the compositions and methods of the present technology may also be demonstrated by a decrease in the symptoms of metabolic disorder, obesity, and/or other CB1 receptor-mediated disorders.

For each of the indicated conditions described herein, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

In an aspect, a method is provided where the method includes inhibiting β-arrestin in a subject by administering a therapeutically effective amount of a compound of any one of the aspects and embodiments of compounds of formulas I, II, III, IV, V, or VII. In some embodiments, the method includes inhibiting β-arrestin recruitment at least 5 times more than inhibiting cyclic AMP formation by administering the therapeutically effective amount of the compound. In some embodiments, the method includes inhibiting β-arrestin recruitment at least 10 times more than inhibiting cyclic AMP formation by administering the therapeutically effective amount of the compound. In any of these embodiments, the subject may be suffering from addiction, a metabolic disorder, obesity, or cancer. In any of these embodiments, the addiction is to at least one of nicotine, ethanol, cocaine, opiods, amphetamines, marijuana, or a synthetic cannabinoid agonist.

In an aspect, a method for treating an addiction in a subject is provided that includes administering a therapeutically effective amount of a compound of any one of the aspects and embodiments of compounds of formulas I, II, III, IV, V, or VII. In some embodiments, the addiction is to at least one of nicotine, ethanol, cocaine, opiods, amphetamines, marijuana, or a synthetic cannabinoid agonist.

In an aspect, a method of inhibiting β-arrestin recruitment is provided that includes contacting a CB1 receptor with a compound of any one of the aspects and embodiments of compounds of formulas I, II, III, IV, V, or VII. In such embodiments, it may be that β-arrestin recruitment is inhibited at least 10 times more than cyclic AMP formation in the contacting step. Such methods may be performed outside of a subject, such as in an assay.

The compounds of the present technology can also be administered to a patient along with other conventional therapeutic agents that may be useful in the treatment of addiction, metabolic syndrome, obesity, and/or CB1 receptor-mediated disorders. The administration may include oral administration, parenteral administration, or nasal administration. In any of these embodiments, the administration may include subcutaneous injections, intravenous injections, intraperitoneal injections, or intramuscular injections. In any of these embodiments, the administration may include oral administration. The methods of the present technology can also comprise administering, either sequentially or in combination with one or more compounds of the present technology, a conventional therapeutic agent in an amount that can potentially or synergistically be effective for the treatment of addiction, metabolic syndrome, obesity, and/or CB1 receptor-mediated disorders.

In one aspect, a compound of the present technology is administered to a patient in an amount or dosage suitable for therapeutic use. Generally, a unit dosage comprising a compound of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a compound of the present technology can vary from $1 \times 10^{-4}$ g/kg to 1 g/kg, preferably, $1 \times 10^{-3}$ g/kg to 1.0 g/kg. Dosage of a compound of the present technology can also vary from 0.01 mg/kg to 100 mg/kg or, preferably, from 0.1 mg/kg to 10 mg/kg.

A compound of the present technology can also be modified, for example, by the covalent attachment of an organic moiety or conjugate to improve pharmacokinetic properties, toxicity or bioavailability (e.g., increased in vivo half-life). The conjugate can be a linear or branched hydrophilic polymeric group, fatty acid group or fatty acid ester group. A polymeric group can comprise a molecular weight that can be adjusted by one of ordinary skill in the art to improve, for example, pharmacokinetic properties, toxicity or bioavailability. Exemplary conjugates can include a polyalkane glycol (e.g., polyethylene glycol (PEG), polypropylene glycol (PPG)), carbohydrate polymer, amino acid polymer or polyvinyl pyrolidone and a fatty acid or fatty acid ester group, each of which can independently comprise from about eight to about seventy carbon atoms. Conjugates for use with a compound of the present technology can also serve as linkers to, for example, any suitable substituents or groups, radiolabels (marker or tags), halogens, proteins, enzymes, polypeptides, other therapeutic agents (for example, a pharmaceutical or drug), nucleosides, dyes, oligonucleotides, lipids, phospholipids and/or liposomes. In one aspect, conjugates can include polyethylene amine (PEI), polyglycine, hybrids of PEI and polyglycine, polyethylene glycol (PEG) or methoxypolyethylene glycol (mPEG). A conjugate can also link a compound of the present technology to, for example, a label (fluorescent or luminescent) or marker (radionuclide, radioisotope and/or isotope) to comprise a probe of the present technology. Conjugates for use with a compound of the present technology can, in one aspect, improve in vivo half-life. Other exemplary conjugates for use with a compound of the present technology as well as applications thereof and related techniques include those generally described by U.S. Pat. No. 5,672,662, which is hereby incorporated by reference herein.

In another aspect, the present technology provides methods of identifying a target of interest including contacting the target of interest with a detectable or imaging effective quantity of a labeled compound of the present technology. A detectable or imaging effective quantity is a quantity of a labeled compound of the present technology necessary to be detected by the detection method chosen. For example, a detectable quantity can be an administered amount sufficient to enable detection of binding of the labeled compound to a target of interest including, but not limited to, an allosteric site in CB1. Suitable labels are known by those skilled in the art and can include, for example, radioisotopes, radionuclides, isotopes, fluorescent groups, biotin (in conjunction with streptavidin complexation), and chemoluminescent groups. Upon binding of the labeled compound to the target of interest, the target may be isolated, purified and further characterized such as by determining the amino acid sequence.

The terms "associated" and/or "binding" can mean a chemical or physical interaction, for example, between a compound of the present technology and a target of interest. Examples of associations or interactions include covalent bonds, ionic bonds, hydrophilic-hydrophilic interactions, hydrophobic-hydrophobic interactions and complexes. Associated can also refer generally to "binding" or "affinity" as each can be used to describe various chemical or physical interactions. Measuring binding or affinity is also routine to those skilled in the art. For example, compounds of the present technology can bind to or interact with a target of interest or precursors, portions, fragments and peptides thereof and/or their deposits.

The examples herein are provided to illustrate advantages of the present technology and to further assist a person of ordinary skill in the art with preparing or using the compounds of the present technology or salts, pharmaceutical compositions, derivatives, metabolites, prodrugs, racemic mixtures or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

General synthetic and analytical details: All reagents and solvents were purchased from Sigma-Aldrich and Alfa Aesar unless otherwise specified, and used without further purification. All anhydrous reactions were performed under an argon or nitrogen atmosphere in flame-dried glassware using scrupulously dry solvents. Complete conversion of starting materials was monitored by TLC. Flash column chromatography employed silica gel 60 (230-400 mesh) and was performed on an Interchim Puriflash450. All compounds were demonstrated to be homogeneous by analytical TLC on precoated silica gel TLC plates (Merck, 60 F245 on glass, layer thickness 250 μm), and chromatograms were visualized by phosphomolybdic acid or anisaldehyde reagent staining. Melting points were determined on a micromelting point apparatus and are uncorrected. IR spectra were recorded on a Perkin-Elmer Spectrum One FT-IR spectrometer. NMR spectra were recorded in $CDCl_3$, $CD_3OD$, DMSO-d6 or in acetone-d6, on Varian 500 MHz and Varian 400 Mz spectrometers, and the chemical shifts (δ) reported are given in parts per million (ppm) relative to TMS as an internal standard. For example, 0.03% TMS was included in CDCl3, and 0.05% TMS in DMSO-d6 or acetone-d6. The spin multiplicities are reported as br (broadened), s (singlet), d (doublet), t (triplet), q (quartet), m (multiplet), and coupling constants (J) are in Hertz (Hz). Mass spectra were recorded in the Department of Chemistry and Chemical Biology at Northeastern University.

Synthesis and Evaluation of Exemplary Allosteric Modulators of the Present Technology

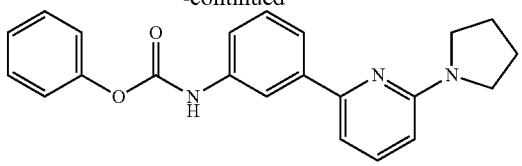

8

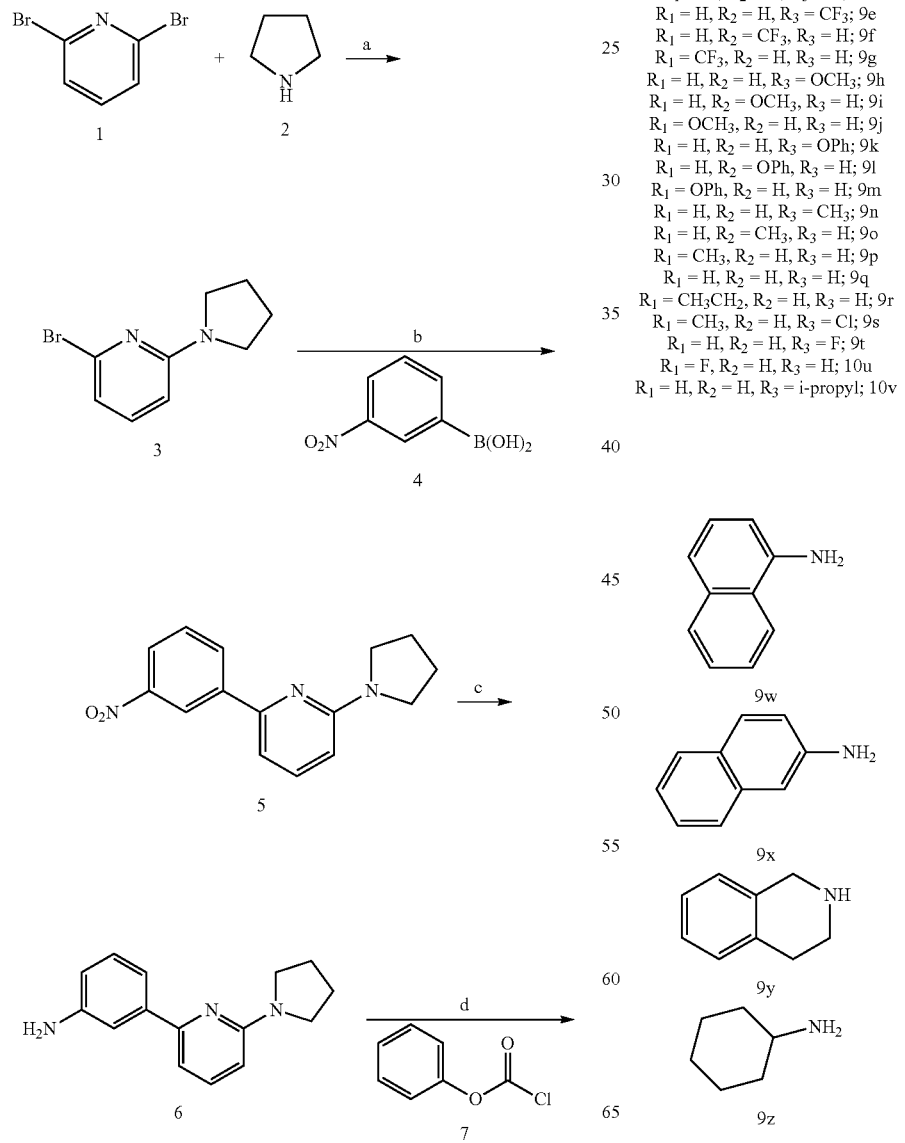

9
- $R_1$ = H, $R_2$ = H, $R_3$ = Cl; 9a
- $R_1$ = H, $R_2$ = H, $R_3$ = I; 9b
- $R_1$ = H, $R_2$ = Cl, $R_3$ = H; 9c
- $R_1$ = Cl, $R_2$ = H, $R_3$ = H; 9d
- $R_1$ = H, $R_2$ = H, $R_3$ = $CF_3$; 9e
- $R_1$ = H, $R_2$ = $CF_3$, $R_3$ = H; 9f
- $R_1$ = $CF_3$, $R_2$ = H, $R_3$ = H; 9g
- $R_1$ = H, $R_2$ = H, $R_3$ = $OCH_3$; 9h
- $R_1$ = H, $R_2$ = $OCH_3$, $R_3$ = H; 9i
- $R_1$ = $OCH_3$, $R_2$ = H, $R_3$ = H; 9j
- $R_1$ = H, $R_2$ = H, $R_3$ = OPh; 9k
- $R_1$ = H, $R_2$ = OPh, $R_3$ = H; 9l
- $R_1$ = OPh, $R_2$ = H, $R_3$ = H; 9m
- $R_1$ = H, $R_2$ = H, $R_3$ = $CH_3$; 9n
- $R_1$ = H, $R_2$ = $CH_3$, $R_3$ = H; 9o
- $R_1$ = $CH_3$, $R_2$ = H, $R_3$ = H; 9p
- $R_1$ = H, $R_2$ = H, $R_3$ = H; 9q
- $R_1$ = $CH_3CH_2$, $R_2$ = H, $R_3$ = H; 9r
- $R_1$ = $CH_3$, $R_2$ = H, $R_3$ = Cl; 9s
- $R_1$ = H, $R_2$ = H, $R_3$ = F; 9t
- $R_1$ = F, $R_2$ = H, $R_3$ = H; 10u
- $R_1$ = H, $R_2$ = H, $R_3$ = i-propyl; 10v

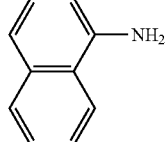

9w

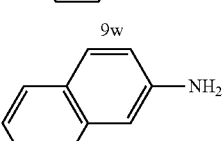

9x

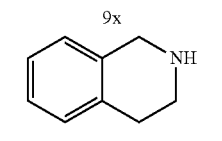

9y

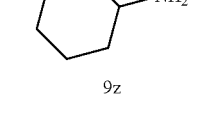

9z

-continued

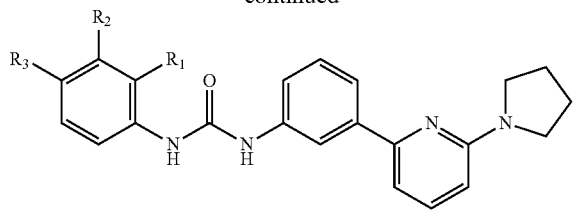

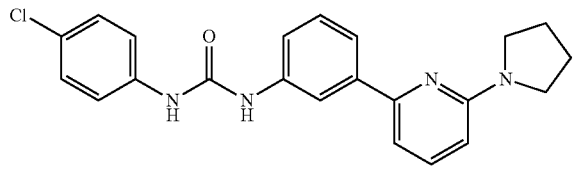 [SMILES: O=C(Nc1ccc(Cl)cc1)Nc1cccc(-c2cccc(N3CCCC3)n2)c1]

10a

10
R₁ = H, R₂ = H, R₃ = Cl; 10a
R₁ = H, R₂ = H, R₃ = I; 10b
R₁ = H, R₂ = Cl, R₃ = H; 10c
R₁ = Cl, R₂ = H, R₃ = H; 10d
R₁ = H, R₂ = H, R₃ = CF₃; 10e
R₁ = H, R₂ = CF₃, R₃ = H; 10f
R₁ = CF₃, R₂ = H, R₃ = H; 10g
R₁ = H, R₂ = H, R₃ = OCH₃; 10h
R₁ = H, R₂ = OCH₃, R₃ = H; 10i
R₁ = OCH₃, R₂ = H, R₃ = H; 10j
R₁ = H, R₂ = H, R₃ = OPh; 10k
R₁ = H, R₂ = OPh, R₃ = H; 10l
R₁ = OPh, R₂ = H, R₃ = H; 10m
R₁ = H, R₂ = H, R₃ = CH₃; 10n
R₁ = H, R₂ = CH₃, R₃ = H; 10o
R₁ = CH₃, R₂ = H, R₃ = H; 10p
R₁ = H, R₂ = H, R₃ = H; 10q
R₁ = CH₃CH₂, R₂ = H, R₃ = H; 10r
R₁ = CH₃, R₂ = H, R₃ = Cl; 10s
R₁ = H, R₂ = H, R₃ = F; 10t
R₁ = F, R₂ = H, R₃ = H; 10u
R₁ = H, R₂ = H, R₃ = i-propyl; 10v

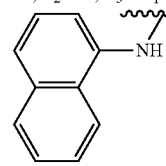

10w

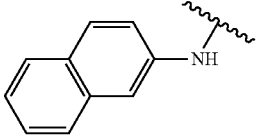

10x

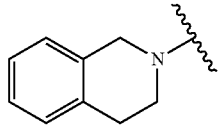

10y

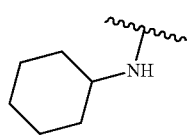

10z

Reagents and Conditions: (a) neat, RT, overnight, 89%; (b) Pd(PPh₃)₄, NaHCO₃, DME, reflux, overnight, 89%; (c) H₂, Pd/C, cat. acetic acid, 1-(4-Chlorophenyl)-3-(3-(6-(pyrrolidin-1-yl)pyridin-2-yl)phenyl)urea (10a): To a solution of 8 (200 mg, 0.556 mmol) in dimethylformamide ("DMF"; 4 mL) was added 4-chloroaniline (78 mg, 0.612 mmol) followed by diisopropylethyl amine ("DIEA"; 0.292 mL, 1.669 mmol) and the mixture heated to 50° C. overnight. Complete conversion of starting material was observed by thin layer chromatography ("TLC"). The reaction mixture was diluted in 100 mL dichloromethane ("DCM") and 100 mL water. The organic layer was separated, washed with water (2×50 mL), dried (MgSO₄) and concentrated under reduced pressure. The crude product was purified by silica gel chromatography eluting with 10-50% ethyl acetate:hexanes to afford the desired product 10a (118 mg, 0.300 mmol, 54% yield) as white solid. $^1$H NMR (500 MHz, DMSO) δ: 8.83 (d, J=20 Hz, 1H), 8.07 (s, 1H), 7.63 (d, J=7.5 Hz, 1H), 7.56 (dd, J=8.0 Hz, J=1.0 Hz, 2H), 7.50 (dd, J=7.0 Hz, J=2.0 Hz, 2H), 7.38-7.31 (m, 3H), 7.05 (d, J=7.0 Hz, 1H), 6.42 (d, J=8.0 Hz, 1H), 3.48 (br s, 4H), 1.98 (quintet, J=3.0 Hz, 4H). MS m/z (M⁺+1): 393.2.

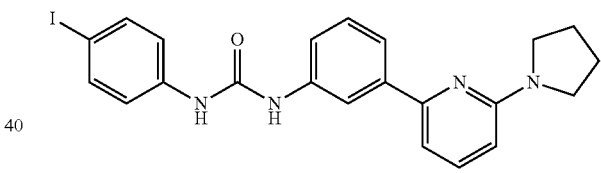

10b 1-(4-Iodophenyl)-3-(3-(6-(pyrrolidin-1-yl)pyridin-2-yl)phenyl)urea (10b): The synthesis was carried out similarly to 10a using 8 (50 mg, 0.139 mmol) and 4-iodoaniline (33.5 mg, 0.153 mmol) in DMF (1.5 mL) followed by DIEA (0.049 mL, 0.278 mmol) to afford the desired product 10b (32 mg, 0.072 mmol, 52% yield) as a light brown solid. $^1$H NMR (500 MHz, CD₃OD) δ: 8.06 (t, J=2.0 Hz, 1H), 7.66 (d, J=8.0 Hz, 1H), 7.60 (d, J=9.0 Hz, 2H), 7.54 (dd, J=8.5 Hz, J=7.0 Hz, 1H), 7.49 (ddd, J=8.0 Hz, J=2.0 Hz, J=1.0 Hz, 1H), 7.35 (t, J=8.0 Hz, 1H), 7.28 (d, J=8.5 Hz, 2H), 7.03 (d, J=7.0 Hz, 1H), 6.41 (d, J=8.5 Hz, 1H), 3.54 (t, J=7.0 Hz, 4H), 2.04 (quintet, J=3.5 Hz, 4H). MS m/z (M⁺+1): 485.0.

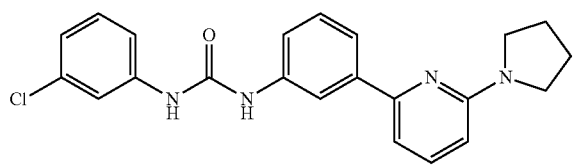 [SMILES: O=C(Nc1cccc(Cl)c1)Nc1cccc(-c2cccc(N3CCCC3)n2)c1]

10c 1-(3-Chlorophenyl)-3-(3-(6-(pyrrolidin-1-yl)pyridin-2-yl)phenyl)urea (10c): The synthesis was carried out as described for 10a using 8 (25 mg, 0.070 mmol) and 3-chloroaniline (9.76 mg, 0.077 mmol) in DMF (1 mL) followed by DIEA (0.036 mL, 0.209 mmol) to afford the desired product 10c (15 mg, 0.038 mmol, 55% yield) as a white solid. $^1$H NMR (500 MHz, CD$_3$OD) δ: 8.03-7.99 (m, 1H), 7.95 (dd, J=9.5 Hz, J=7.5 Hz, 1H), 7.67 (t, J=2.0 Hz, 1H), 7.52-7.48 (m, 2H), 7.44-7.39 (m, 1H), 7.30-7.26 (m, 2H), 7.07-6.99 (m, 3H), 3.69 (t, J=6.5 Hz, 4H), 2.01 (quintet, J=3.0 Hz, 4H). MS m/z (M$^+$+1): 393.3.

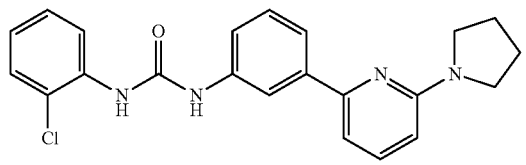 [SMILES: O=C(Nc1cccc(-c2cccc(N3CCCC3)n2)c1)Nc1ccccc1Cl]

1-(2-Chlorophenyl)-3-(3-(6-(pyrrolidin-1-yl)pyridin-2-yl)phenyl)urea: (10d): The synthesis was carried out as described for 10a using 8 (25 mg, 0.070 mmol) and chloroaniline (9.76 mg, 0.077 mmol) in DMF (1 mL) followed by DIEA (0.036 mL, 0.209 mmol) to afford the desired product 10d (18 mg, 0.046 mmol, 66% yield) as a white solid. $^1$H NMR (500 MHz, CD$_3$OD) δ: 8.11 (dd, J=8.5 Hz, J=2.0 Hz, 1H), 8.08 (t, J=2.0 Hz, 1H), 7.98 (dd, J=9.5 Hz, J=7.5 Hz, 1H), 7.52 (t, J=8.0 Hz, 1H), 7.46 (td, J=8.0 Hz, J=1.0 Hz, 1H), 7.43 (dd, J=8.5 Hz, J=1.5 Hz, 2H), 7.29 (dt, J=8.0 Hz, J=1.5 Hz, 1H), 7.09-7.03 (m, 3H), 3.70 (t, J=6.5 Hz, 4H), 2.16 (quintet, J=3.0 Hz, 4H). MS m/z (M$^+$+1): 393.4.

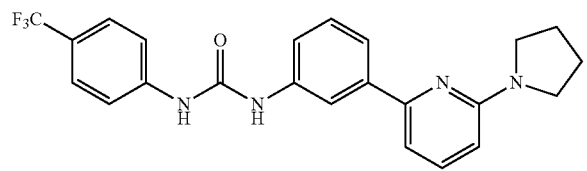 [SMILES: Cc1ccc(NC(=O)Nc2cccc(-c3cccc(N4CCCC4)n3)c2)cc1]

1-(3-(6-(Pyrrolidin-1-yl)pyridin-2-yl)phenyl)-3-(4-(trifluoromethyl) phenyl)urea (10e): The synthesis was carried out as described for 10a using 8 (25 mg, 0.070 mmol) and 4-(trifluoromethyl)aniline (12.33 mg, 0.077 mmol) in DMF (1 mL) followed by DIEA (0.036 mL, 0.209 mmol) to afford the desired product 10e (17 mg, 0.042 mmol, 60% yield) as a white solid. $^1$H NMR (500 MHz, CD$_3$OD) δ: 8.05 (t, J=1.5 Hz, 1H), 8.0 (dd, J=9.0 Hz, J=7.0 Hz, 1H), 7.66 (d, J=9.0 Hz, 2H), 7.53 (t, J=8.5 Hz, 1H), 7.47 (ddd, J=8.5 Hz, J=2.0 Hz, J=1.0 Hz, 1H), 7.41 (ddd, J=8.5 Hz, J=2.0 Hz, J=1.0 Hz, 1H), 7.07 (dt, J=9.0 Hz, J=1.0 Hz, 2H), 3.72 (t, J=7.0 Hz, 4H), 2.17 (quintet, J=3.0 Hz, 4H). MS m/z (M$^+$+1): 427.1.

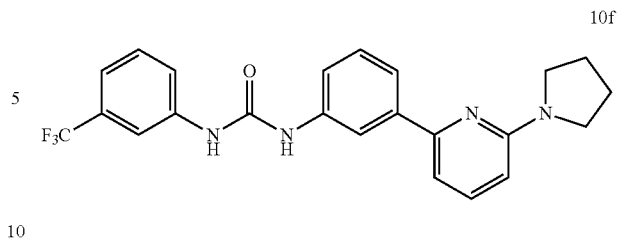

1-(3-(6-(Pyrrolidin-1-yl)pyridin-2-yl)phenyl)-3-(3-(trifluoromethyl) phenyl)urea (10f): The synthesis was carried out as described for 10a using 8 (25 mg, 0.070 mmol) and 3-(trifluoromethyl)aniline (12.33 mg, 0.077 mmol) in DMF (1 mL) followed by DIEA (0.036 mL, 0.209 mmol) to afford the desired product 10f (20 mg, 0.047 mmol, 67% yield) as a white solid. $^1$H NMR (500 MHz, CD$_3$OD) δ: 8.04 (t, J=2.0 Hz, 1H), 7.99 (dd, J=8.5 Hz, J=2.0 Hz, 1H), 7.95 (br s, 1H), 7.62 (dd, J=8.0 Hz, J=2.0 Hz, 1H), 7.54-7.45 (m, 3H), 7.42 (td, J=6.5 Hz, J=2.0 Hz, 1H), 7.31 (dd, J=2.0 Hz, J=1.0 Hz, 1H), 7.07 (d, J=1.5 Hz, 1H), 7.06 (s, 1H), 3.71 (t, J=7.0 Hz, 4H), 2.17 (quintet, J=3.5 Hz, 4H). MS m/z (M$^+$+1): 427.1.

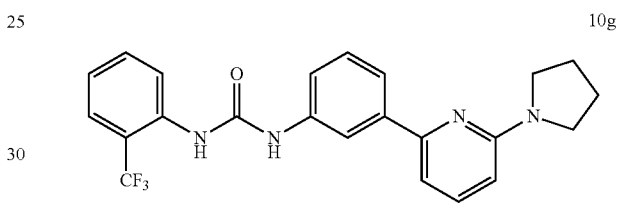

1-(3-(6-(Pyrrolidin-1-yl)pyridin-2-yl)phenyl)-3-(2-(trifluoromethyl) phenyl)urea (10g): The synthesis was carried out as described for 10a using 8 (25 mg, 0.070 mmol) and 3-(trifluoromethyl)aniline (12.33 mg, 0.077 mmol) in DMF (1 mL) followed by DIEA (0.036 mL, 0.209 mmol) to afford the desired product 10 g (15 mg, 0.035 mmol, 50% yield) as a white solid. $^1$H NMR (500 MHz, CD$_3$OD) δ: 8.08 (t, J=2.0 Hz, 1H), 7.98 (dd, J=9.0 Hz, J=7.0 Hz, 1H), 7.92 (d, J=8.5 Hz, 1H), 7.69 (d, J=8.0 Hz, 1H), 7.63 (dt, J=8.0 Hz, J=1.0 Hz, 1H), 7.53 (t, J=8.0 Hz, 1H), 7.47-7.40 (m, 2H), 7.33 (t, J=8.0 Hz, 1H), 7.07 (d, J=2.0 Hz, 1H), 7.05 (s, 1H), 3.70 (t, J=6.5 Hz, 4H), 2.17 (quintet, J=3.5 Hz, 4H). MS m/z (M$^+$+1): 427.3.

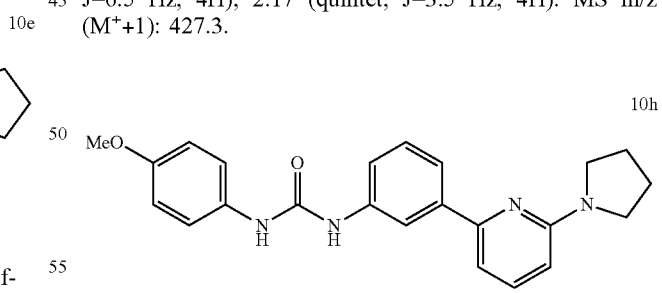

1-(4-Methoxyphenyl)-3-(3-(6-(pyrrolidin-1-yl)pyridin-2-yl)phenyl)urea (10h): The synthesis was carried out as described for 10a using 8 (50 mg, 0.139 mmol) and 4-methoxyaniline (18.85 mg, 0.153 mmol) in DMF (2 mL) followed by DIEA (53.5 μl, 0.306 mmol) to afford the desired product 10h (30 mg, 0.077 mmol, 55% yield) as a white solid. $^1$H NMR (500 MHz, CD$_3$OD) δ: 8.03-7.95 (m, 2H), 7.50 (dd as t, J=8.0 Hz, 1H), 7.42 (dd, J=8.0 Hz, J=1.0 Hz, 1H), 7.39 (ddd, J=8.0 Hz, J=2.0 Hz, J=1.0 Hz, 1H), 7.35-7.28 (m, 2H), 7.09-6.99 (m, 2H), 6.91-6.83 (m, 2H), 3.77 (s, 3H), 3.71 (t, J=6.0 Hz, 4H), 2.17 (quintet, J=3.0 Hz, 4H). MS m/z (M++1): 389.2.

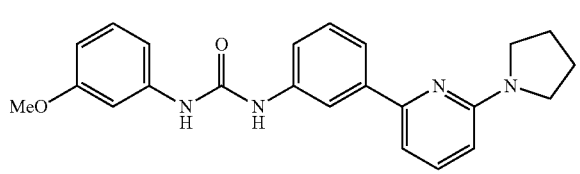 [SMILES: COc1cccc(NC(=O)Nc2cccc(-c3cccc(N4CCCC4)n3)c2)c1]

1-(3-Methoxyphenyl)-3-(3-(6-(pyrrolidin-1-yl)pyridin-2-yl)phenyl)urea (10i): The synthesis was carried out as described for 10a using 8 (50 mg, 0.139 mmol) and 3-methoxyaniline (18.85 mg, 0.153 mmol) in DMF (2 mL) followed by DIEA (53.5 µl, 0.306 mmol) to afford the desired product 10i (36 mg, 0.093 mmol, 67% yield) as a white solid. $^1$H NMR (500 MHz, CD$_3$OD) δ: 8.01 (t, J=2.0 Hz, 1H), 7.96 (dd, J=9.0 Hz, J=7.5 Hz, 1H), 7.50 (dd as t, J=7.5 Hz, 1H), 7.47 (td, J=8.0 Hz, J=2.0 Hz, 1H), 7.40 (td, J=7.5 Hz, J=2.0 Hz, 1H), 7.19-7.15 (m, 2H), 7.03 (t, J=7.5 Hz, 2H), 6.96-6.91 (m, 1H), 6.61 (ddd, J=8.5 Hz, J=2.0 Hz, J=1.0 Hz, 1H), 3.78 (s, 3H), 3.71 (t, J=6.0 Hz, 4H), 2.17 (quintet, J=3.0 Hz, 4H). MS m/z (M++1): 389.2.

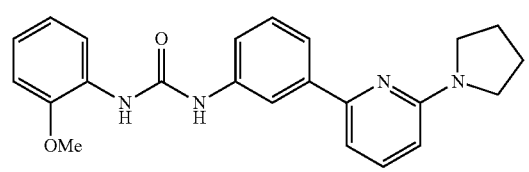 [SMILES: COc1ccccc1NC(=O)Nc1cccc(-c2cccc(N3CCCC3)n2)c1]

1-(2-Methoxyphenyl)-3-(3-(6-(pyrrolidin-1-yl)pyridin-2-yl)phenyl)urea (10j): The synthesis was carried out as described for 10a using 8 (50 mg, 0.139 mmol) and 2-methoxyaniline (18.85 mg, 0.153 mmol) in DMF (2 mL) followed by DIEA (53.5 µl, 0.306 mmol) to afford the desired product 10j (37 mg, 0.095 mmol, 68% yield) as a white solid. $^1$H NMR (500 MHz, CD$_3$OD) δ: 8.09 (m, 2H), 7.99 (dd, J=9.0 Hz, J=7.5 Hz, 1H), 7.51 (t, J=7.5 Hz, 1H), 7.40 (dt, J=7.5 Hz, J=1.0 Hz, 2H), 7.07 (d, J=2.5 Hz, 1H), 7.06 (d, J=1.0 Hz, 1H), 7.02-6.98 (m, 2H), 6.94-6.89 (m, 1H), 3.92 (s, 3H), 3.71 (t, J=7.0 Hz, 4H), 2.17 (quintet, J=3.5 Hz, 4H). MS m/z (M++1): 389.2.

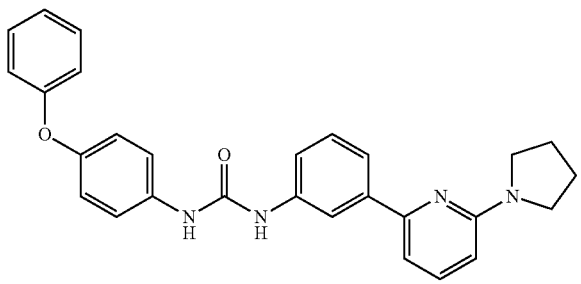 [SMILES: O=C(Nc1ccc(Oc2ccccc2)cc1)Nc1cccc(-c2cccc(N3CCCC3)n2)c1]

1-(4-Phenoxyphenyl)-3-(3-(6-(pyrrolidin-1-yl)pyridin-2-yl)phenyl)urea (10k): The synthesis was carried out as described for 10a using 8 (30 mg, 0.083 mmol) and 4-phenoxyaniline (17.01 mg, 0.092 mmol) in DMF (2 mL) followed by DIEA (0.032 mL, 0.184 mmol) to afford the desired product 10k (24 mg, 0.053 mmol, 64% yield) as a white solid. $^1$H NMR (500 MHz, CD$_3$OD) δ: 8.04 (t, J=9.0 Hz, 1H), 7.99 (dd, J=9.0 Hz, J=7.5 Hz, 1H), 7.51 (t, J=7.5 Hz, 1H), 7.46-7.42 (m, 3H), 7.40 (ddd, J=8.0 Hz, J=2.0 Hz, J=1.0 Hz, 1H), 7.35-7.30 (m, 2H), 7.08-7.03 (m, 3H), 6.98-6.93 (m, 4H), 3.71 (t, J=7.0 Hz, 4H), 2.17 (quintet, J=3.5 Hz, 4H). MS m/z (M++1): 451.5.

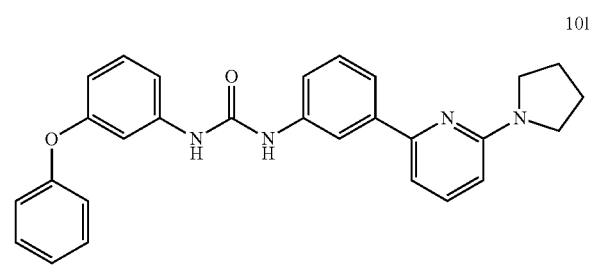

1-(3-Phenoxyphenyl)-3-(3-(6-(pyrrolidin-1-yl)pyridin-2-yl)phenyl)urea (10l): The synthesis was carried out as described for 10a using 8 (30 mg, 0.083 mmol) and 3-phenoxyaniline (17.01 mg, 0.092 mmol) in DMF (2 mL) followed by DIEA (0.032 mL, 0.184 mmol) to afford the desired product 10l (22 mg, 0.049 mmol, 59% yield) as a white solid. $^1$H NMR (500 MHz, CD$_3$OD) δ: 8.02 (t, J=9.0 Hz, 1H), 7.98 (dd, J=9.0 Hz, J=7.0 Hz, 1H), 7.50 (t, J=8.0 Hz, 1H), 7.43-7.38 (m, 2H), 7.37-7.33 (m, 2H), 7.29-7.26 (m, 2H), 7.12 (dd, J=2.0 Hz, J=1.0 Hz, 1H), 7.11-7.09 (m, 1H), 7.06 (d, J=3.5 Hz, 1H), 7.04 (d, J=2.0 Hz, 1H), 7.00 (dd, J=9.0 Hz, J=1.0 Hz, 2H), 6.65 (ddd, J=7.5 Hz, J=2.5 Hz, J=1.0 Hz, 1H), 3.71 (t, J=7.0 Hz, 4H), 2.17 (quintet, J=3.5 Hz, 4H). MS m/z (M++1): 451.1.

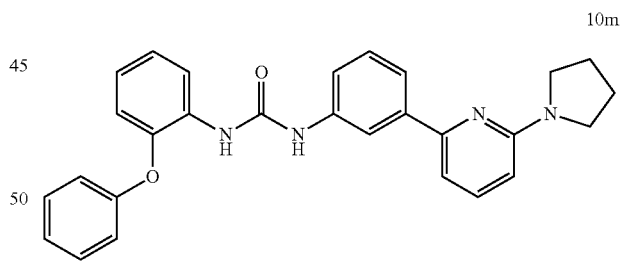

1-(2-Phenoxyphenyl)-3-(3-(6-(pyrrolidin-1-yl)pyridin-2-yl)phenyl)urea (10m): The synthesis was carried out as described for 10a using 8 (30 mg, 0.083 mmol) and 2-phenoxyaniline (17.01 mg, 0.092 mmol) in DMF (2 mL) followed by DIEA (0.032 mL, 0.184 mmol) to afford the desired product 10m (25 mg, 0.055 mmol, 66% yield) as a white solid. $^1$H NMR (500 MHz, CD$_3$OD) δ: 8.20 (dd, J=8.5 Hz, J=1.5 Hz, 1H), 8.06 (t, J=3.0 Hz, 1H), 7.99 (dd, J=9.0 Hz, J=7.0 Hz, 1H), 7.49 (t, J=8.5 Hz, 1H), 7.41-7.34 (m, 4H), 7.13 (ddd, J=6.0 Hz, J=3.0 Hz, J=1.0 Hz, 2H), 7.09-6.98 (m, 5H), 6.87 (dd, J=8.5 Hz, J=1.5 Hz, 1H), 3.71 (t, J=7.0 Hz, 4H), 2.17 (quintet, J=3.5 Hz, 4H). MS m/z (M++1): 451.2.

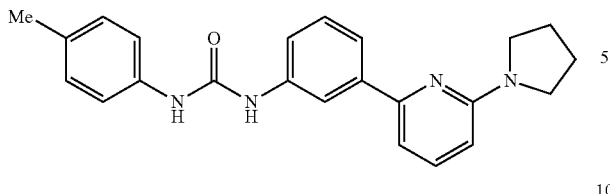

10n 7.10-7.03 (m, 3H), 3.67 (t, J=7.0 Hz, 4H), 2.31 (s, 3H), 2.16 (quintet, J=3.5 Hz, 4H). MS m/z (M++1): 373.3.

1-(3-(6-(Pyrrolidin-1-yl)pyridin-2-yl)phenyl)-3-(p-tolyl)urea (10n): The synthesis was carried out as described for 10a using 8 (50 mg, 0.139 mmol) and p-toluidine (16.40 mg, 0.153 mmol) in DMF (2 mL) followed by DIEA (0.053 mL, 0.306 mmol) to afford the desired product 10n (33 mg, 0.089 mmol, 64% yield) as a white solid. ¹H NMR (500 MHz, CD₃OD) δ: 8.03 (d, J=2.0 Hz, 1H), 7.98 (dd, J=9.5 Hz, J=7.5 Hz, 1H), 7.50 (t, J=8.0 Hz, 1H), 7.42 (ddd, J=8.0 Hz, J=2.0 Hz, J=1.0 Hz, 1H), 7.39 (ddd, J=8.0 Hz, J=2.0 Hz, J=1.0 Hz, 1H), 7.31 (d, J=9.0 Hz, 2H), 7.12 (d, J=7.5 Hz, 2H), 7.07 (d, J=3.0 Hz, 1H), 7.05 (d, J=1.5 Hz, 1H), 3.71 (t, J=6.5 Hz, 4H), 2.30 (s, 3H), 2.17 (quintet, J=3.5 Hz, 4H). MS m/z (M++1): 373.2.

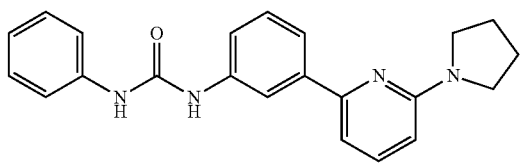

10q

1-Phenyl-3-(3-(6-(pyrrolidin-1-yl)pyridin-2-yl)phenyl)urea (10q): The synthesis was carried out as described for 10a using 8 (50 mg, 0.139 mmol) and aniline (14.25 mg, 0.153 mmol) in DMF (1 mL), followed by DIEA (0.053 mL, 0.306 mmol) to afford the desired product 10q (15 mg, 0.042 mmol, 30% yield) as a white solid. ¹H NMR MS m/z (M++1): 359.2.

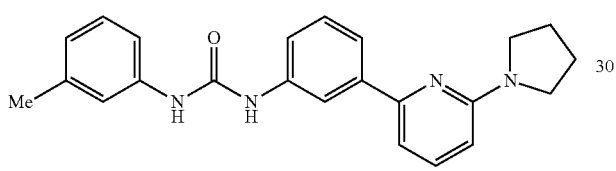

10o 1-(3-(6-(Pyrrolidin-1-yl)pyridin-2-yl)phenyl)-3-(m-tolyl)urea (10o): The synthesis was carried out as described for 10a using 8 (50 mg, 0.139 mmol) and m-toluidine (16.40 mg, 0.153 mmol) in DMF (2 mL) followed by DIEA (0.053 mL, 0.306 mmol) to afford the desired product 10o (36 mg, 0.097 mmol, 69% yield) as a white solid. ¹H NMR (500 MHz, CD₃OD) δ: 8.04 (t, J=2.0 Hz, 1H), 7.98 (dd, J=11.0 Hz, J=9.5 Hz, 1H), 7.49 (d, J=9.5 Hz, 1H), 7.46-7.38 (m, 2H), 7.29-7.22 (m, 2H), 7.17 (t, J=9.5 Hz, 1H), 7.07 (s, 1H), 7.04 (d, J=2.5 Hz, 1H), 6.91-6.85 (m, 1H), 3.71 (t, J=6.5 Hz, 4H), 2.32 (s, 3H), 2.16 (quintet, J=3.0 Hz, 4H). MS m/z (M++1): 373.1.

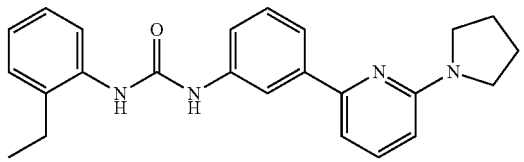

10r 1-(2-Ethylphenyl)-3-(3-(6-(pyrrolidin-1-yl)pyridin-2-yl)phenyl)urea (10r): The synthesis was carried out as described for 10a using 8 (50 mg, 0.139 mmol) and 2-ethylaniline (16.86 mg, 0.139 mmol) followed by DIEA (0.049 mL, 0.278 mmol) to afford the desired product 10r (42 mg, 0.109 mmol, 78% yield) as a white solid. ¹H NMR (500 MHz, CD₃OD) δ: 8.04 (t, J=2.0 Hz, 1H), 7.95 (dd, J=9.5 Hz, J=2.5 Hz, 1H), 7.58 (dd, J=8.0 Hz, J=1.0 Hz, 1H), 7.49 (t, J=8.0 Hz, 1H), 7.45 (td, J=8.0 Hz, J=1.5 Hz, 1H), 7.39 (td, J=8.0 Hz, J=1.0 Hz, 1H), 7.24 (dd, J=7.0 Hz, J=1.5 Hz, 1H), 7.18 (dd, J=8.0 Hz, J=1.5 Hz, 1H), 7.11 (dd, J=8.0 Hz, J=1.5 Hz, 1H), 7.03 (dd as t, J=8.0 Hz, 2H), 3.68 (t, J=7.0 Hz, 4H), 2.68 (q, J=8.0 Hz, 2H), 2.14 (quintet, J=3.0 Hz, 4H), 1.23 (t, J=8.0 Hz, 3H).

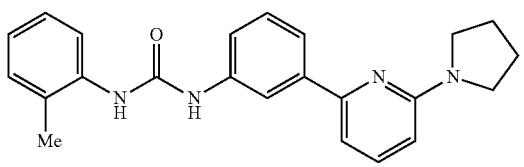

10p 1-(3-(6-(Pyrrolidin-1-yl)pyridin-2-yl)phenyl)-3-(o-tolyl)urea (10p): The synthesis was carried out as described for 10a using 8 (50 mg, 0.139 mmol) and o-toluidine (16.40 mg, 0.153 mmol) in DMF (2 mL) followed by DIEA (0.053 mL, 0.306 mmol) to afford the desired product 10p (15 mg, 0.040 mmol, 29% yield) as a white solid. ¹H NMR (500 MHz, CD₃OD) δ: 8.07 (t, J=2.5 Hz, 1H), 7.98 (dd, J=11.0 Hz, J=9.5 Hz, 1H), 7.63 (dd, J=9.5 Hz, J=1.0 Hz, 1H), 7.50 (d, J=10.5 Hz, 1H), 7.46-7.38 (m, 2H), 7.25-7.15 (m, 2H),

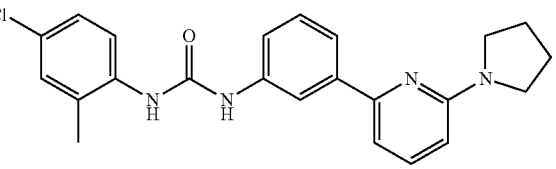

10s 1-(4-Chloro-2-methylphenyl)-3-(3-(6-(pyrrolidin-1-yl)pyridin-2-yl)phenyl)urea (10s): The synthesis was carried out as described for 10a using 8 (50 mg, 0.139 mmol) and 4-chloro-2-methylaniline (19.70 mg, 0.139 mmol) in DMF (1 mL) followed by DIEA (0.049 mL, 0.278 mmol) to afford the desired product 10s (32 mg, 0.079 mmol, 56% yield) as a white solid. ¹H NMR (500 MHz, CD₃OD) δ: 8.05 (t, J=2.0 Hz, 1H), 7.97 (dd, J=9.0 Hz, J=2.0 Hz, 1H), 7.65 (d, J=8.5 Hz, 1H), 7.50 (t, J=8.0 Hz, 1H), 7.44 (ddd, J=8.0 Hz, J=2.0 Hz, J=1.0 Hz, 1H), 7.40 (td, J=8.0 Hz, J=1.5 Hz, 1H), 7.24

(d, J=2.0 Hz, 1H), 7.17 (dd, J=8.5 Hz, J=2.5 Hz, 1H), 7.05 (d, J=1.0 Hz, 1H), 7.03 (d, J=3.0 Hz, 1H), 3.69 (t, J=6.5 Hz, 4H), 2.29 (s, 3H), 2.16 (quintet, J=3.0 Hz, 4H).

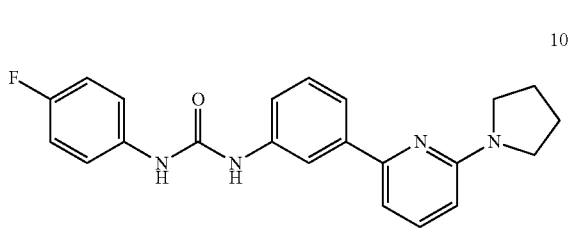

1-(4-Fluorophenyl)-3-(3-(6-(pyrrolidin-1-yl)pyridin-2-yl)phenyl)urea (10t): The synthesis was carried out as described for 10a using 8 (25 mg, 0.070 mmol) in DMF (1 mL) and 4-fluoroaniline (8.5 mg, 0.077 mmol) followed by DIEA (0.036 mL, 0.209 mmol) to afford the desired product 10t (11 mg, 0.03 mmol, 43% yield) as a white solid. $^1$H NMR (500 MHz, CD$_3$OD) δ: 8.10-7.96 (m, 2H), 7.60-7.38 (m, 5H), 7.16-7.02 (m, 4H), 3.70 (t, J=7.0 Hz, 4H), 2.17 (quintet, J=3.0 Hz, 4H).

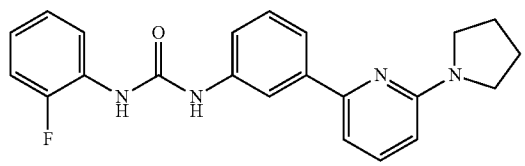

1-(2-Fluorophenyl)-3-(3-(6-(pyrrolidin-1-yl)pyridin-2-yl)phenyl)urea (10u): The synthesis was carried out as described for 10a using 8 (50 mg, 0.139 mmol) and 2-fluoroaniline (15.46 mg, 0.139 mmol) in DMF (1 mL) followed by DIEA (0.049 mL, 0.278 mmol) to afford the desired product 10u (22 mg, 0.058 mmol, 42% yield) as a white solid. $^1$H NMR (500 MHz, CD$_3$OD) δ: 8.06 (td, J=8.0 Hz, J=1.5 Hz, 2H), 7.95 (dd, J=9.0 Hz, J=7.5 Hz, 1H), 7.51 (t, J=7.5 Hz, 1H), 7.45 (ddd, J=8.0 Hz, J=2.0 Hz, J=1.0 Hz, 1H), 7.42 (td, J=7.5 Hz, J=1.5 Hz, 1H), 7.18-7.11 (m, 2H), 7.08-6.99 (m, 3H), 3.70 (t, J=6.5 Hz, 4H), 2.16 (quintet, J=3.5 Hz, 4H).

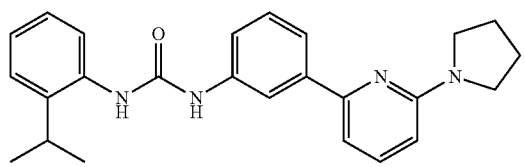

1-(2-Isopropylphenyl)-3-(3-(6-(pyrrolidin-1-yl)pyridin-2-yl)phenyl)urea (10v): The synthesis was carried out as described for 10a using a solution of 8 (50 mg, 0.139 mmol) in DMF (3 mL), 2-isopropylaniline (18.81 mg, 0.139 mmol) followed by Et$_3$N (0.039 mL, 0.278 mmol) to afford the desired product 10v (33 mg, 0.082 mmol, 59% yield) as a white solid. $^1$H NMR (500 MHz, CD$_3$OD) δ: 8.07 (br s, 1H), 7.93-7.86 (m, 1H), 7.48 (d, J=6.0 Hz, 1H), 7.47 (d, J=4.0 Hz, 1H), 7.45-7.41 (m, 2H), 7.36-7.31 (m, 1H), 7.19 (dd, J=6.5 Hz, J=4.0 Hz, 2H), 7.05 (d, J=7.5 Hz, 1H), 6.95 (br s, 1H), 3.67 (t, J=6.5 Hz, 4H), 3.23 (septet, J=2.0 Hz, 1H), 2.13 (quintet, J=3.0 Hz, 4H), 1.27 (s, 3H), 1.26 (s, 3H).

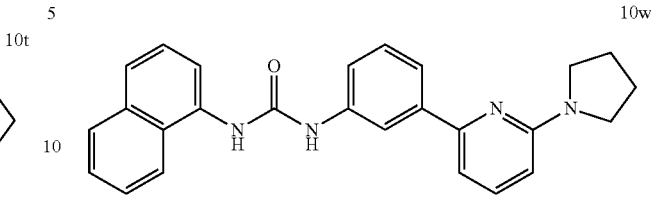

1-(Naphthalen-1-yl)-3-(3-(6-(pyrrolidin-1-yl)pyridin-2-yl)phenyl)urea (10w): The synthesis was carried out as described for 10a using 8 (50 mg, 0.139 mmol) and naphthalen-1-amine (21.91 mg, 0.153 mmol) in DMF (2 mL) followed by DIEA (53.5 µl, 0.306 mmol) to afford the desired product 10w (31 mg, 0.076 mmol, 54% yield) as a white solid. $^1$H NMR (500 MHz, CD$_3$OD) δ: 8.1 (t, J=1.5 Hz, 1H), 7.96 (dd, J=9.5 Hz, J=7.5 Hz, 1H), 7.90 (dd, J=8.0 Hz, J=1.5 Hz, 1H), 7.79 (dd, J=8.0 Hz, J=1.5 Hz, 1H), 7.72 (d, J=8.0 Hz, 1H), 7.58-7.46 (m, 5H), 7.41 (td, J=7.0 Hz, J=1.5 Hz, 1H), 7.04 (dd, J=5.5 Hz, J=1.0 Hz, 1H), 7.02 (dd, J=7.0 Hz, J=1.0 Hz, 1H), 3.71 (t, J=7.0 Hz, 4H), 2.17 (quintet, J=3.5 Hz, 4H). MS m/z (M$^+$+1): 409.

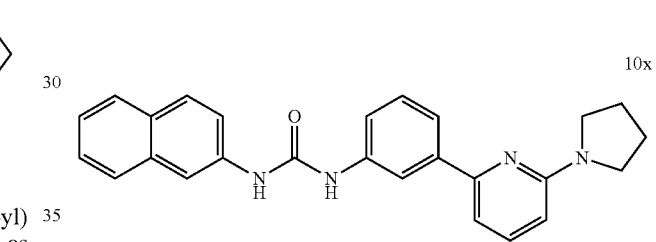

1-(Naphthalen-2-yl)-3-(3-(6-(pyrrolidin-1-yl)pyridin-2-yl)phenyl)urea (10x): The synthesis was carried out as described for 10a using 8 (50 mg, 0.139 mmol) and naphthalen-2-amine (21.91 mg, 0.153 mmol) in DMF (2 mL) followed by DIEA (53.5 µl, 0.306 mmol) to afford the desired product 10x (35 mg, 0.086 mmol, 61% yield) as a white solid. $^1$H NMR (500 MHz, CD$_3$OD) δ: 8.09 (t, J=1.5 Hz, 1H), 8.04 (d, J=2.5 Hz, 1H), 7.99 (dd, J=9.0 Hz, J=7.5 Hz, 1H), 7.83-7.73 (m, 3H), 7.55-7.47 (m, 3H), 7.46-7.40 (m, 2H), 7.37 (dt, J=7.5 Hz, J=1.5 Hz, 1H), 7.07 (dd, J=2.5 Hz, J=1.0 Hz, 1H), 7.06 (dd, J=5.0 Hz, J=1.0 Hz, 1H), 3.71 (t, J=7.0 Hz, 4H), 2.17 (quintet, J=3.5 Hz, 4H). MS m/z (M$^+$+1): 409.1.

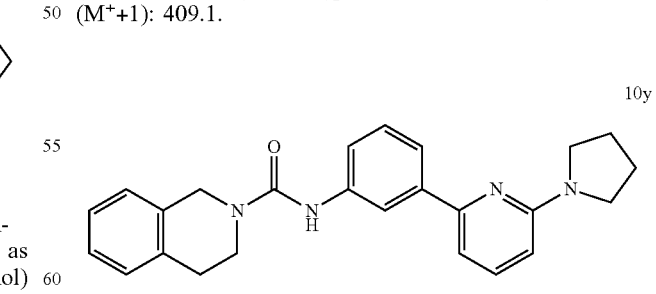

N-(3-(6-(Pyrrolidin-1-yl)pyridin-2-yl)phenyl)-3,4-dihydroisoquinoline-2(1H)-carboxamide (10y): The synthesis was carried out as described for 10a using 8 (50 mg, 0.139 mmol) and 1,2,3,4-tetrahydroisoquinoline (18.53 mg, 0.139 mmol) in DMF (2 mL) followed by DIEA (53.5 µl, 0.306 mmol) to afford the desired product 10y (35 mg, 0.088 mmol, 63% yield) as a white solid. ¹H NMR (500 MHz, CD₃OD) δ: 7.97 (dd, J=9.0 Hz, J=7.0 Hz, 1H), 7.87 (t, J=2.0 Hz, 1H), 7.52 (td, J=8.5 Hz, J=1.5 Hz, 1H), 7.49 (t, J=7.0 Hz, 1H), 7.40 (td, J=8.0 Hz, J=1.5 Hz, 1H), 7.21-7.16 (m, 4H), 7.04 (dt, J=9.5 Hz, J=1.0 Hz, 2H), 4.72 (s, 2H), 3.79 (t, J=6.0 Hz, 2H), 3.70 (t, J=6.5 Hz, 4H), 2.94 (t, J=6.0 Hz, 2H), 2.16 (quintet, J=3.0 Hz, 4H). MS m/z (M⁺+1): 399.4.

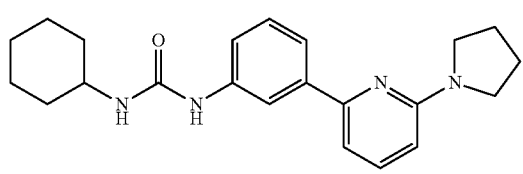

10z

1-Cyclohexyl-3-(3-(6-(pyrrolidin-1-yl)pyridin-2-yl)phenyl)urea (10z): The synthesis was carried out as described for 10a using 8 (50 mg, 0.139 mmol) and cyclohexanamine (15.18 mg, 0.153 mmol) in DMF (2 mL) followed by DIEA (0.053 mL, 0.306 mmol) to afford the desired product 10z (27 mg, 0.074 mmol, 53% yield) as a white solid. ¹H NMR (500 MHz, CD₃OD) δ: 7.97 (t, J=2.0 Hz, 1H), 7.59 (td, J=7.5 Hz, J=1.5 Hz, 1H), 7.52 (dd, J=8.5 Hz, J=7.5 Hz, 1H), 7.40 (ddd, J=9.0 Hz, J=2.0 Hz, J=1.0 Hz, 1H), 7.30 (t, J=8.0 Hz, 1H), 7.0 (d, J=7.5 Hz, 1H), 6.39 (d, J=7.0 Hz, 1H), 3.62-3.56 (m, 1H), 3.53 (t, J=6.5 Hz, 4H), 2.04 (quintet, J=3.5 Hz, 4H), 1.94 (dd, J=12.0 Hz, J=3.5 Hz, 2H), 1.75 (dt, J=13.5 Hz, J=3.5 Hz, 2H), 1.66-1.59 (m, 1H), 1.46-1.35 (m, 2H), 1.30-1.18 (m, 3H). MS m/z (M⁺+1): 365.3.

Scheme 2: General Synthetic Procedure for Certain Embodiments of Formula VI

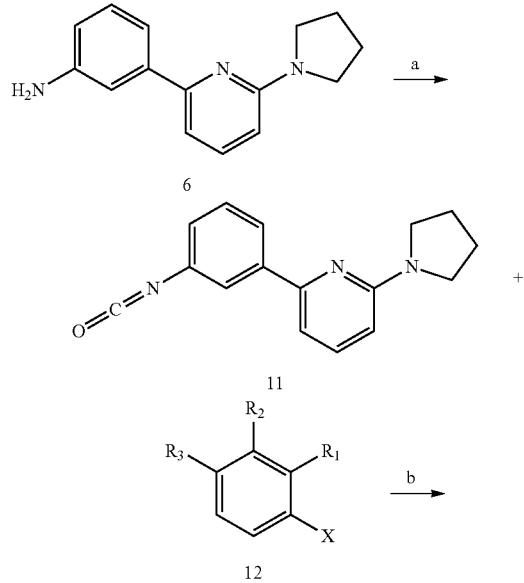

R₁ = H, R₂ = H, R₃ = Cl, X = NHCH₃; 12a
R₁ = H, R₂ = H, R₃ = Cl, X = OH; 12b
R₁ = CH₃, R₂ = H, R₃ = Cl, X = OH; 12c

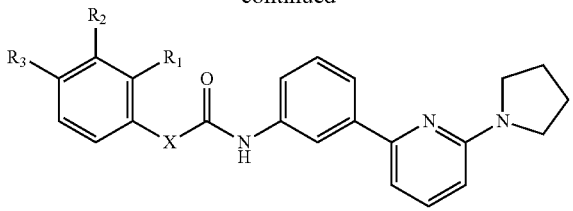

13

R₁ = H, R₂ = H, R₃ = Cl, X = NCH₃; 13a
R₁ = H, R₂ = H, R₃ = Cl, X = O; 13b
R₁ = CH₃, R₂ = H, R₃ = Cl, X = O; 13c

Reagents and Conditions: (a) Triphosgene, Et₃N, toluene, 70° C., 3 h; (b) Et₃N, DCM, 0° C., 3 h, 21-46%.

1-(4-Chlorophenyl)-1-methyl-3-(3-(6-(pyrrolidin-1-yl)pyridin-2-yl)phenyl)urea (13a): To a solution of 11 (50 mg, 0.188 mmol) in DCM (2 mL) was added 4-chloro-N-methylaniline (26.7 mg, 0.188 mmol) followed by Et₃N (0.079 mL, 0.565 mmol) and stirred at 0° C. for 6 h. The reaction mixture was diluted in 20 mL DCM and 20 mL water. The organic layer was separated, washed with water (2×20 mL), dried (MgSO₄) and concentrated under reduced pressure. The crude product was purified by silica gel chromatography by eluting with 10-50% ethyl acetate:hexanes to afford the desired product 13a (35 mg, 0.086 mmol, 46% yield) as a white solid. ¹H NMR (500 MHz, CD₃OD) δ: 7.98 (td, J=8.0 Hz, J=1.5 Hz, 1H), 7.86-7.84 (m, 1H), 7.48 (d, J=1.5 Hz, 1H), 7.46 (td, J=4.0 Hz, J=1.5 Hz, 3H), 7.43-7.39 (m, 1H), 7.38 (d, J=1.5 Hz, 1H), 7.36 (t, J=1.5 Hz, 1H), 7.06 (dd, J=9.0 Hz, J=1.0 Hz, 1H), 7.02 (dd, J=7.0 Hz, J=1.0 Hz, 1H), 3.70 (t, J=7.0 Hz, 4H), 3.35 (s, 3H), 2.16 (quintet, J=3.0 Hz, 4H).

4-Chlorophenyl (3-(6-(pyrrolidin-1-yl)pyridin-2-yl)phenyl)carbamate (13b): To a solution of 11 (25 mg, 0.094 mmol) in DCM (2 mL) was added 4-chlorophenol (12.11 mg, 0.094 mmol) followed by Et₃N (0.026 mL, 0.188 mmol) and stirred at 0° C. for 16 h. The organic layer was separated, washed with 2×20 mL water and brine, dried (MgSO₄) and concentrated under reduced pressure. The crude product was purified by silica gel chromatography with 10-50% ethyl acetate:hexanes to afford the desired product 13a (15 mg, 0.038 mmol, 40% yield) as a white solid. ¹H NMR (500 MHz, CD₃OD) δ: 8.01 (br s, 1H), 7.97 (dd, J=9.0 Hz, J=7.5 Hz, 1H), 7.61 (ddd, J=8.5 Hz, J=2.5 Hz, J=1.0 Hz, 1H), 7.54 (t, J=8.5 Hz, 1H), 7.46 (td, J=8.5 Hz, J=1.0 Hz, 1H), 7.41 (d, J=8.5 Hz, 2H), 7.21 (d, J=9.0 Hz, 2H), 7.12 (d, J=8.5 Hz, 1H), 7.04 (t, J=7.0 Hz, 2H), 6.30 (d, J=8.5 Hz, 1H), 3.69 (t, J=6.5 Hz, 4H), 2.15 (quintet, J=3.0 Hz, 4H).

4-Chloro-2-methylphenyl (3-(6-(pyrrolidin-1-yl)pyridin-2-yl)phenyl)carbamate (13c): The synthesis was carried out as described for 13a using a solution of 11 (25 mg, 0.094 mmol) in DCM (3 mL) and 4-chloro-2-methylphenol (13.44 mg, 0.094 mmol) to afford the desired product 13c (8 mg, 0.02 mmol, 21% yield) as a white solid. ¹H NMR (500 MHz, CD₃OD) δ: 8.03-7.97 (m, 2H), 7.65 (ddd, J=8.5 Hz, J=2.5 Hz, J=1.5 Hz, 1H), 7.55 (t, J=8.0 Hz, 1H), 7.47 (dd, J=8.0 Hz, J=1.0 Hz, 1H), 7.31 (d, J=2.5 Hz, 1H), 7.23 (dd, J=8.5 Hz, J=2.5 Hz, 1H), 7.12 (d, J=8.5 Hz, 1H), 7.08 (dd, J=9.0 Hz, J=1.0 Hz, 1H), 7.04 (d, J=7.0 Hz, 1H), 3.70 (t, J=7.0 Hz, 4H), 2.25 (s, 3H), 2.16 (quintet, J=3.0 Hz, 4H).

Scheme 3: General Synthetic Procedure for Certain Oxygenated Embodiments of Formula VI

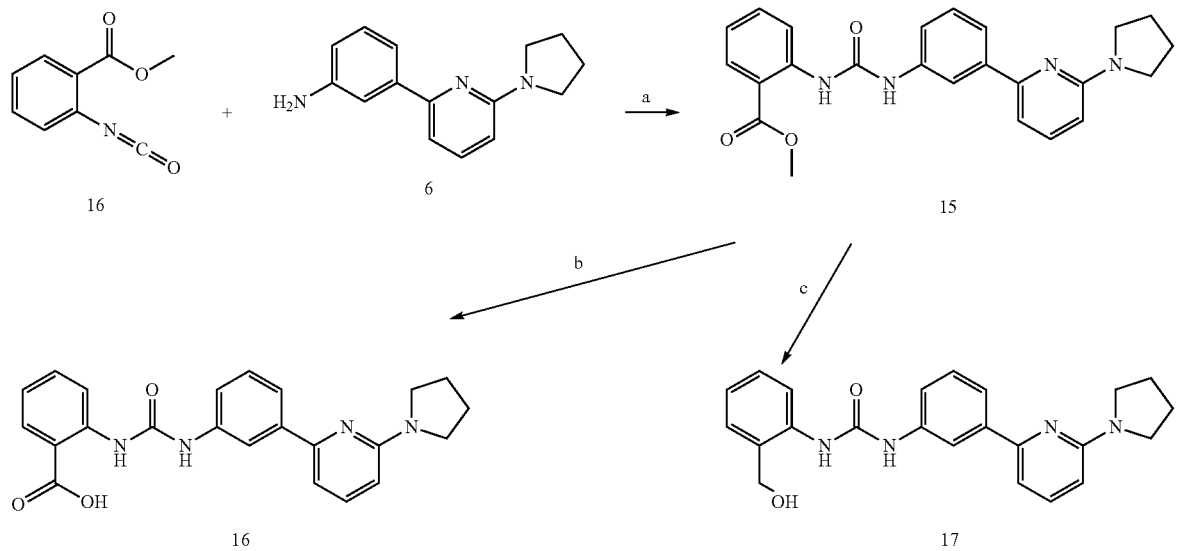

Reagents and Conditions: (a) Et₃N, DCM, 0° C., 3 h, 76%; (b) LiOH, THF, MeOH overnight, 68%; (c) LAH, THF, 0° C., 5 h, 40%

Methyl 2-(3-(3-(6-(pyrrolidin-1-yl)pyridin-2-yl)phenyl)ureido)benzoate (15): To a solution of 6 (50 mg, 0.209 mmol) in DCM (3 mL) was added 16 (37 mg, 0.209 mmol) followed by Et₃N (0.058 mL, 0.418 mmol) and stirred at room temperature for 16 h. Reaction was diluted in 20 mL DCM and 20 mL water. The organic layer was separated, washed with 2×20 mL water and brine, dried (MgSO₄) and concentrated under reduced pressure. The crude product was purified by silica gel chromatography with 10-50% ethyl acetate:hexanes to afford the desired product 15 (66 mg, 0.159 mmol, 76% yield) as a white solid. $^1$H NMR (500 MHz, CD₃OD) δ: 8.37 (d, J=8.5 Hz, 1H), 8.06 (d, J=1.0 Hz, 1H), 8.04 (d, J=1.5 Hz, 1H), 7.99 (dd, J=9.0 Hz, J=7.5 Hz, 1H), 7.58-7.51 (m, 3H), 7.42 (td, J=6.5 Hz, J=2.0 Hz, 1H), 7.11-7.0 (m, 3H), 4.42 (q, J=7.0 Hz, 2H), 3.71 (t, J=6.5 Hz, 4H), 2.17 (quintet, J=3.5 Hz, 4H), 1.42 (t, J=7.0 Hz, 3H).

2-(3-(3-(6-(Pyrrolidin-1-yl)pyridin-2-yl)phenyl)ureido)benzoic acid (16): To a solution of 15 (25 mg, 0.058 mmol) in THF (3 mL) and MeOH (3 mL) was added 1M LiOH (0.290 mL, 0.290 mmol) and stirred for 16 h at room temperature. The reaction mixture was concentrated and the crude product was purified by silica gel chromatography using 10-50% ethyl acetate:hexanes to afford the desired product 16 (16 mg, 0.040 mmol, 68% yield) as a white solid. $^1$H NMR (500 MHz, CD₃OD) δ: 8.05 (dd, J=8.0 Hz, J=1.5 Hz, 1H), 7.98 (dd, J=9.0 Hz, J=7.5 Hz, 1H), 7.83 (ddd as td, J=8.0 Hz, J=1.0 Hz, 1H), 7.75 (t, J=2.0 Hz, 1H), 7.71 (tt, J=7.5 Hz, J=1.5 Hz, 2H), 7.57 (ddd, J=8.5 Hz, J=2.0 Hz, J=1.0 Hz, 1H), 7.27 (dt, J=7.5 Hz, J=1.0 Hz, 1H), 7.24 (d, J=7.5 Hz, 1H), 7.08 (dd, J=9.0 Hz, J=1.0 Hz, 1H), 7.05 (d, J=7.5 Hz, 1H), 3.69 (t, J=6.5 Hz, 4H), 2.15 (quintet, J=3.0 Hz, 4H).

1-(2-(Hydroxymethyl)phenyl)-3-(3-(6-(pyrrolidin-1-yl)pyridin-2-yl)phenyl)urea (17): To a solution of 15 (50 mg, 0.116 mmol) in tetrahydrofuran ("THF"; 5 mL) at 0° C. was added lithium aluminum hydride ("LAH"; 0.116 mL, 0.116 mmol) and stirred for 5 h. The reaction mixture was diluted with 50 mL DCM and 50 mL 10% Rochelle salt solution. The organic layer was separated, washed with water (2×50 mL), dried (MgSO₄) and concentrated under reduced pressure. The crude product was purified using silica gel chromatography eluting with 10-50% ethyl acetate:hexanes to afford the desired product 17 (18 mg, 0.046 mmol, 40% yield) as a white solid. $^1$H NMR (500 MHz, CD₃OD) δ: 8.03 (s, 1H), 7.98 (dd, J=9.0 Hz, J=2.0 Hz, 1H), 7.75 (d, J=8.0 Hz, 1H), 7.50 (d, J=6.0 Hz, 2H), 7.39 (ddd as td, J=6.0 Hz, J=2.0 Hz, 1H), 7.33 (d, J=7.5 Hz, 1H), 7.27 (dt, J=7.5 Hz, J=1.5 Hz, 1H), 7.10 (t, J=7.5 Hz, 1H), 7.06 (d, J=4.5 Hz, 1H), 7.04 (d, J=3.0 Hz, 1H), 4.67 (s, 2H), 3.70 (t, J=6.5 Hz, 4H), 2.15 (quintet, J=3.0 Hz, 4H).

Scheme 4: Heterocyclyl Embodiments of Formula VI

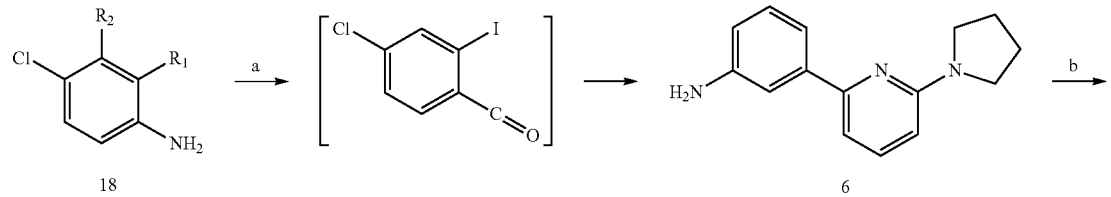

R₁ = I, R₂ = H, 18a
R₁ = H, R₂ = I, 18b

-continued
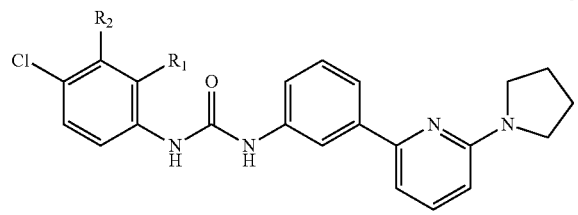
19
R₁ = I, R₂ = H; 19a
R₁ = H, R₂ = I, 19b
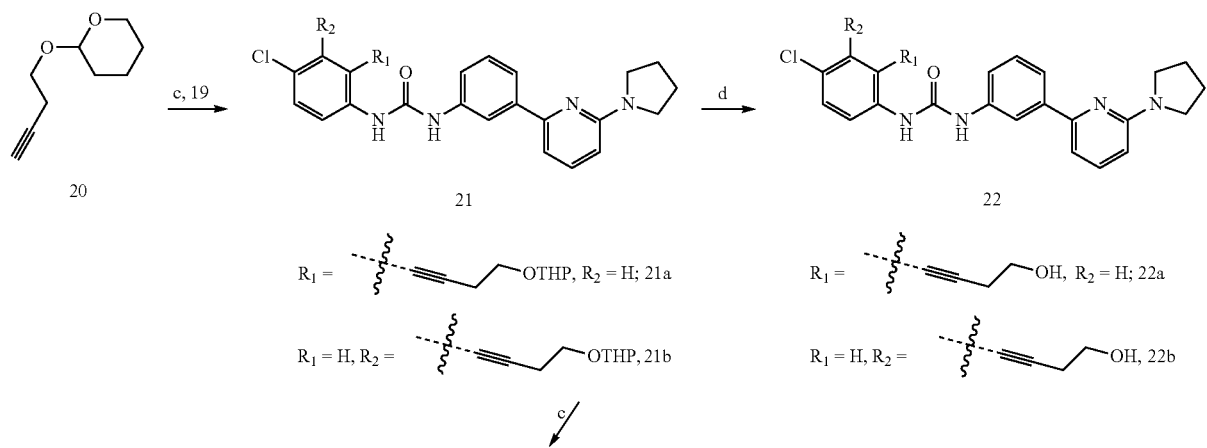
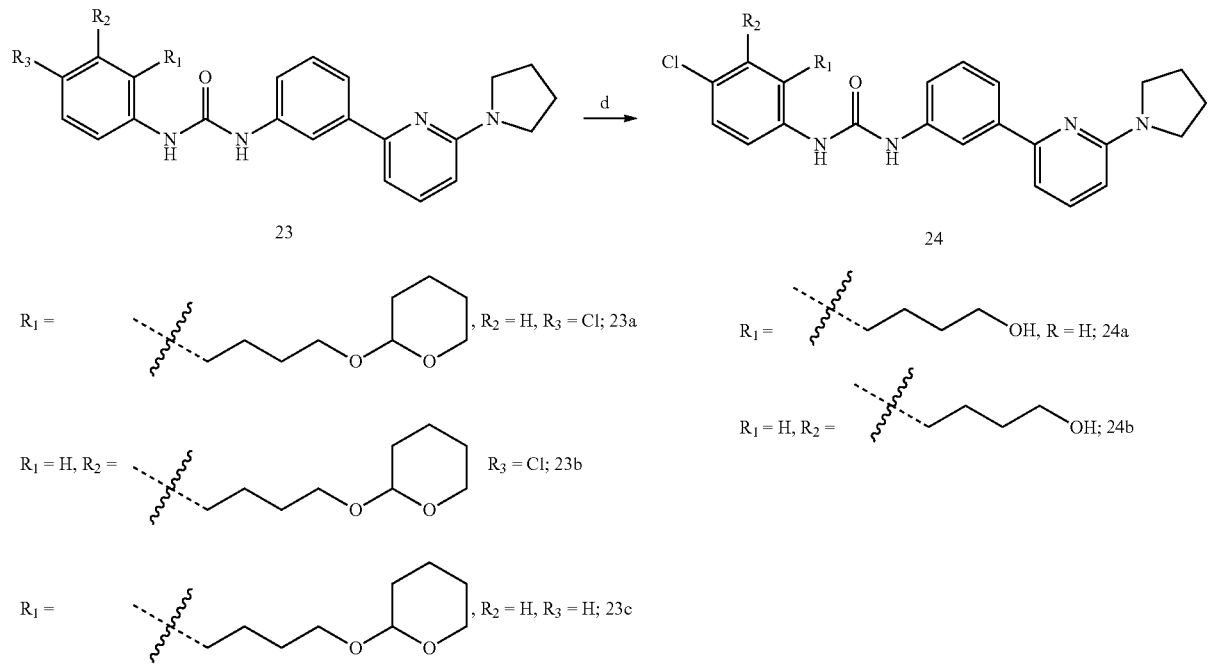
Reagents and Conditions: (a) Triphosgene, Et₃N, toluene, 70° C., 3 h; (b) Et₃N. DCM, 0° C., 3 h, 54-66%; (c) Pd(PPh₃)₂Cl₂, (Cu(I)Cl, 90° C., 2 h, 67-76%; (d) PTSA, methanol, room temp, 5 h, 52-76%; (e) Pd/C, H₂, methanol, room temp, overnight, 23-84%.

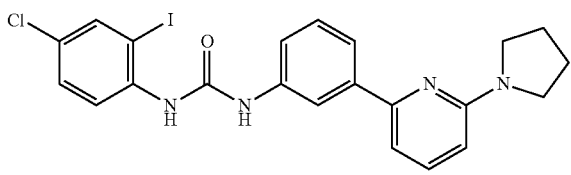

19a 1-(4-Chloro-2-iodophenyl)-3-(3-(6-(pyrrolidin-1-yl)pyridin-2-yl) phenyl)urea (19a): To a solution of triphosgene (222 mg, 0.750 mmol) in toluene (10 mL) was added a solution of 4-chloro-2-iodoaniline (500 mg, 1.973 mmol), Et$_3$N (3.3 mL, 23.68 mmol) in toluene (10 mL) under argon atmosphere. The resulting solution was heated to 70° C. for 3 h. The reaction mixture was filtered through a pad of celite and eluted with Et$_2$O. The filtrate was concentrated under reduced pressure to give the crude product as brown solid which was used for the next step without further purification. To the solution of crude intermediate in DCM (25 mL) was added 3-(6-(pyrrolidin-1-yl)pyridin-2-yl)aniline (472 mg, 1.973 mmol) followed by Et$_3$N (3.3 mL, 23.68 mmol) and stirred for 6 hours at 0° C. The reaction mixture was diluted with 100 mL DCM and 100 mL water. The organic layer was separated, washed with 2×50 mL water and brine, dried (MgSO$_4$) and concentrated under reduced pressure. The crude product was purified by silica gel chromatography eluting with 10-50% ethyl acetate:hexanes to afford the desired product 21a (676 mg, 1.302 mmol, 66% yield) as a white solid. $^1$H NMR (500 MHz, DMSO) δ: 9.57 (s, 1H), 8.09 (t, J=2.0 Hz, 1H), 7.98 (s, 1H), 7.91 (d, J=2.5 Hz, 1H), 7.88 (d, J=8.5 Hz, 1H), 7.66 (td, J=8.0 Hz, J=1.5 Hz, 1H), 7.56 (dd, J=8.5 Hz, J=7.5 Hz, 2H), 7.44 (dd, J=7.0 Hz, J=2.5 Hz, 1H), 7.36 (t, J=8.0 Hz, 1H), 7.06 (d, J=7.5 Hz, 1H), 6.42 (d, J=8.5 Hz, 1H), 3.48 (t, J=6.5 Hz, 4H), 1.97 (quintet, J=3.0 Hz, 4H). MS m/z (M$^+$+1): 519.0.

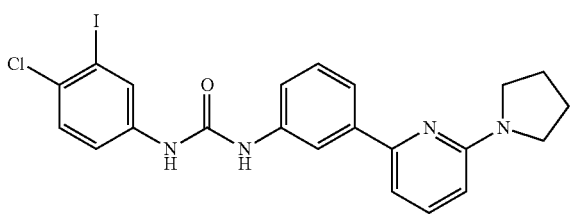

19b 1-(4-Chloro-3-iodophenyl)-3-(3-(6-(pyrrolidin-1-yl)pyridin-2-yl) phenyl)urea (19b): The synthesis was carried out as described for 19a using a solution of triphosgene (267 mg, 0.900 mmol) in toluene (10 mL), 4-chloro-3-iodoaniline (600 mg, 2.367 mmol) and Et$_3$N (3.96 mL, 28.4 mmol) in toluene (10 mL) followed by 6 (567 mg, 2.367 mmol) and Et$_3$N (3.96 mL, 28.4 mmol) to afford the desired product 19b (660 mg, 1.272 mmol, 54% yield) as a white solid. $^1$H NMR (500 MHz, CD$_3$OD+CDCl$_3$) δ: 8.12 (d, J=2.5 Hz, 1H), 8.05 (t, J=1.5 Hz, 1H), 7.67 (td, J=8.5 Hz, J=4.0 Hz, 1H), 7.54 (dd, J=8.5 Hz, J=7.0 Hz, 1H), 7.52-7.48 (m, 1H), 7.43 (dd, J=9.0 Hz, J=2.5 Hz, 1H), 7.40 (s, 1H), 7.38-7.35 (m, 1H), 7.03 (d, J=7.0 Hz, 1H), 6.41 (d, J=8.5 Hz, 1H), 3.54 (t, J=7.0 Hz, 4H), 2.04 (quintet, J=3.0 Hz, 4H).

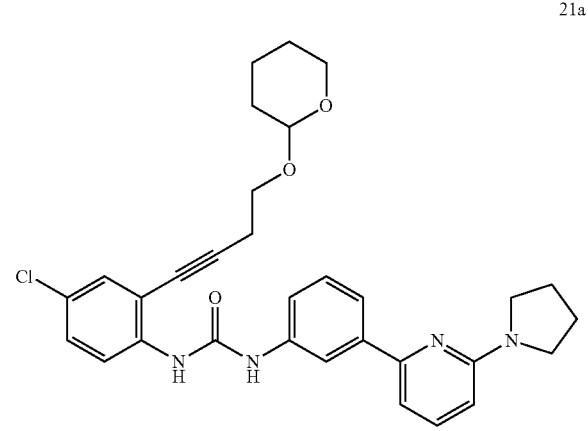

21a 1-(4-Chloro-2-(4-((tetrahydro-2H-pyran-2-yl)oxy)but-1-yn-1-yl)phenyl)-3-(3-(6-(pyrrolidin-1-yl)pyridin-2-yl)phenyl)urea (21a): A solution of 19a (500 mg, 0.964 mmol) and 2-(but-3-ynyloxy)tetrahydro-2H-pyran (163 mg, 1.060 mmol) in DMF (10 mL) was treated with Pd(PPh$_3$)$_2$Cl$_2$ (33.8 mg, 0.048 mmol) and copper(I) iodide (12.84 mg, 0.067 mmol), and the reaction was heated to 90° C. for 2 h. After cooling to the room temperature, the reaction mixture was diluted with 100 mL DCM and 100 mL water. The organic layer was separated, washed with water (2×50 mL), dried (MgSO$_4$) and concentrated under reduced pressure. The crude product was purified by silica gel chromatography using 10-50% ethyl acetate:hexanes to afford the desired product 21a (350 mg, 0.642 mmol, 67% yield) as a white solid. $^1$H NMR (500 MHz, CD$_3$OD) δ: 8.11 (d, J=9.0 Hz, 1H), 8.09 (t, J=2.0 Hz, 1H), 7.68 (d, J=8.0 Hz, 1H), 7.55 (dd, J=7.5 Hz, J=2.5 Hz, 2H), 7.38 (t, J=8.0 Hz, 1H), 7.33 (d, J=2.5 Hz, 1H), 7.27 (dd, J=9.5 Hz, J=2.5 Hz, 1H), 7.04 (d, J=7.0 Hz, 1H), 6.43 (d, J=8.5 Hz, 1H), 4.69 (dd, J=5.0 Hz, J=2.5 Hz, 1H), 3.96-3.87 (m, 2H), 3.71-3.64 (m, 1H), 3.54 (t, J=7.0 Hz, 4H), 3.52-3.47 (m, 1H), 2.81 (t, J=7.0 Hz, 2H), 2.04 (quintet, J=3.5 Hz, 4H), 1.85-1.78 (m, 1H), 1.75-1.67 (m, 1H), 1.62-1.42 (m, 4H). MS m/z (M$^+$+1): 545.2.

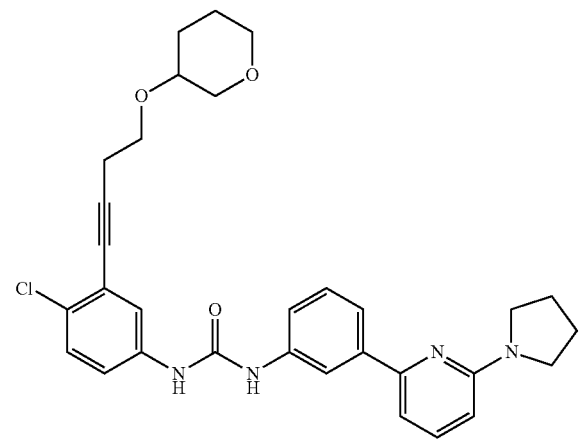

21b 1-(4-Chloro-3-(4-((tetrahydro-2H-pyran-2-yl)oxy)but-1-yn-1-yl)phenyl)-3-(3-(6-(pyrrolidin-1-yl)pyridin-2-yl)phenyl)urea (21b): The synthesis was carried out as described for 21a using 19b (500 mg, 0.964 mmol) and 2-(but-3-ynyloxy)tetrahydro-2H-pyran (163 mg, 1.060 mmol) in DMF (10 mL), Pd(PPh₃)₂Cl₂ (33.8 mg, 0.048 mmol) and copper(I)iodide (12.84 mg, 0.067 mmol) to afford the desired product 21b (400 mg, 0.734 mmol, 76% yield) as a white solid. ¹H NMR (500 MHz, CD₃OD) δ: 8.06 (t, J=2.0 Hz, 1H), 7.66 (td, J=8.0 Hz, J=2.0 Hz, 1H), 7.63 (d, J=2.5 Hz, 1H), 7.54 (dd as t, J=8.0 Hz, 1H), 7.51-7.48 (m, 1H), 7.37-7.36 (m, 1H), 7.35 (d, J=2.5 Hz, 1H), 7.32 (t, J=8.0 Hz, 1H), 7.03 (d, J=7.0 Hz, 1H), 6.41 (d, J=8.5 Hz, 1H), 4.74 (t, J=3.5 Hz, 1H), 4.0-3.86 (m, 2H), 3.69-3.62 (m, 1H), 3.54 (t, J=6.5 Hz, 4H), 3.16 (quintet, J=1.5 Hz, 1H), 2.76 (t, J=6.5 Hz, 2H), 2.04 (quintet, J=3.0 Hz, 4H), 1.92-1.82 (m, 1H), 1.78-1.68 (m, 1H), 1.65-1.48 (m, 4H). MS m/z (M⁺+1): 545.3.

1-(4-Chloro-3-(4-hydroxybut-1-yn-1-yl)phenyl)-3-(3-(6-(pyrrolidin-1-yl)pyridin-2-yl)phenyl)urea (22b): The synthesis was carried out as described for 22a by adding p-toluenesulfonic acid monohydrate (87 mg, 0.459 mmol), 21b (50 mg, 0.092 mmol) in methanol (5 mL) to afford the desired product 22b (30 mg, 0.065 mmol, 71% yield) as a white solid. ¹H NMR (500 MHz, CD₃OD) δ: 8.06 (t, J=2.0 Hz, 1H), 7.67 (td, J=7.5 Hz, J=1.50 Hz, 1H), 7.62 (d, J=2.5 Hz, 1H), 7.54 (t, J=8.0 Hz, 1H), 7.50 (ddd, J=5.5 Hz, J=2.5 Hz, J=1.0 Hz, 1H), 7.37 (dd, J=5.0 Hz, J=2.0 Hz, 1H), 7.35 (d, J=2.0 Hz, 1H), 7.32 (t, J=8.0 Hz, 1H), 7.03 (d, J=7.0 Hz, 1H), 6.41 (d J=8.5 Hz, 1H), 3.76 (t, J=7.0 Hz, 2H), 3.54 (t, J=7.0 Hz, 4H), 2.68 (t, J=7.0 Hz, 2H), 2.04 (quintet, J=3.5 Hz, 4H). MS m/z (M⁺+1): 461.2

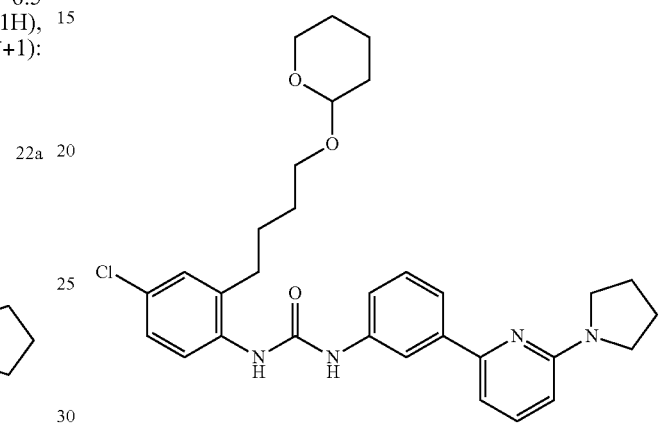

23a 1-(4-Chloro-2-(4-((tetrahydro-2H-pyran-2-yl)oxy)butyl)phenyl)-3-(3-(6-(pyrrolidin-1-yl)pyridin-2-yl)phenyl)urea (23a): To a solution of 21a (100 mg, 0.183 mmol) in methanol (25 mL) was added Pd/C (9.76 mg, 9.17 µmol) and the reaction mixture was stirred under hydrogen atmosphere for 12 h. The desired product along with dechlorinated byproduct was observed. Pd/C was filtered off and filtrate was concentrated under reduced pressure. The crude product was purified by silica gel chromatography by eluting with 5-50% ethyl acetate:hexanes to afford the desired product 23a (70 mg, 0.127 mmol, 69% yield) as a white solid. ¹H NMR (500 MHz, CD₃OD) δ: 8.08 (t, J=2.0 Hz, 1H), 7.65 (td, J=8.5 Hz, J=2.0 Hz, 1H), 7.60 (dd, J=8.0 Hz, J=1.0 Hz, 1H), 7.55-7.51 (m, 2H), 7.34 (t, J=8.0 Hz, 1H), 7.24-7.20 (m, 1H), 7.19 (dd, J=8.0 Hz, J=2.0 Hz, 1H), 7.09 (dt, J=8.0 Hz, J=1.5 Hz, 1H), 7.03 (d, J=7.0 Hz, 1H), 7.40 (d, J=8.5 Hz, 1H), 4.53 (t, J=4.0 Hz, 1H), 3.84-3.74 (m, 3H), 3.54 (t, J=7.0 Hz, 4H), 3.48-3.38 (m, 2H), 2.70 (t, J=8.0 Hz, 2H), 2.04 (quintet, J=3.0 Hz, 4H), 1.80-1.58 (m, 6H), 1.54-1.38 (m, 4H).

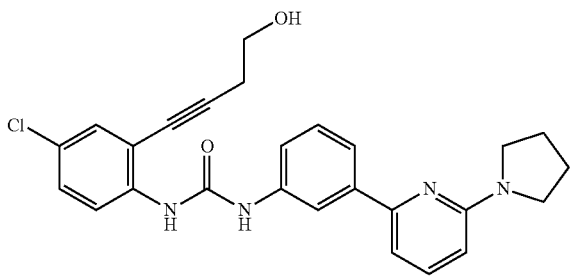

22a 1-(4-Chloro-2-(4-hydroxybut-1-yn-1-yl)phenyl)-3-(3-(6-(pyrrolidin-1-yl)pyridin-2-yl)phenyl)urea (22a)

To a solution of 21a (50 mg, 0.092 mmol) in methanol (5 mL) was added p-toluenesulfonic acid monohydrate (87 mg, 0.459 mmol) and stirred for 5 h at room temperature. The reaction solution was diluted with 100 mL DCM and 100 mL 10% NaHCO₃. The organic layer was separated, washed with 2×50 mL water and brine, dried (MgSO₄) and concentrated under reduced pressure. The crude product was purified by silica gel chromatography by eluting with 10-50% ethyl acetate:hexanes to afford the desired product 21a (32 mg, 0.069 mmol, 76% yield) as a white solid. ¹H NMR (500 MHz, CD₃OD) δ: 8.15 (d, J=9.0 Hz, 1H), 8.09 (t, J=2.0 Hz, 1H), 7.75 (dt, J=7.5 Hz, J=2.0 Hz, 1H), 7.56-7.52 (m, 2H), 7.39-7.34 (m, 2H), 7.27 (dd, J=9.0 Hz, J=2.5 Hz, 1H), 7.03 (d, J=7.0 Hz, 1H), 6.42 (d, J=8.5 Hz, 1H), 3.81 (t, J=6.0 Hz, 2H), 3.54 (t, J=7.0 Hz, 4H), 2.75 (t, J=6.0 Hz, 2H), 2.04 (quintet, J=3.5 Hz, 4H). MS m/z (M⁺+1): 461.2.

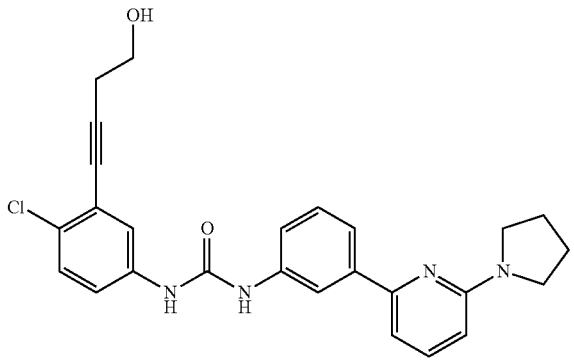

22b

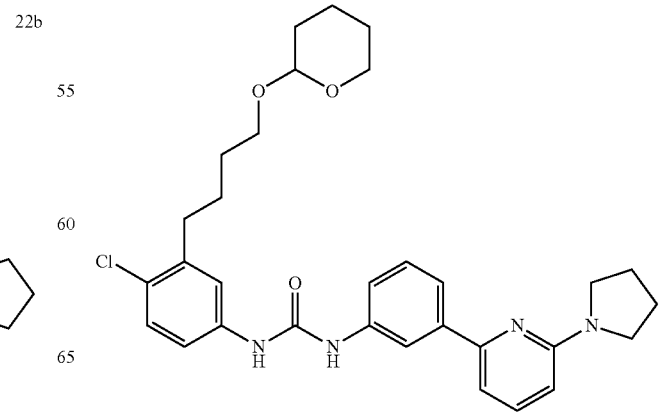

23b 1-(4-Chloro-3-(4-((tetrahydro-2H-pyran-2-yl)oxy)butyl) phenyl)-3-(3-(6-(pyrrolidin-1-yl)pyridin-2-yl)phenyl)urea (23b): The synthesis was carried out as described for 23a using 21b (80 mg, 0.147 mmol) in methanol (25 mL) and Pd/C (15.62 mg, 0.015 mmol) under hydrogen atmosphere to afford the desired product 23b (68 mg, 0.124 mmol, 84% yield) as a white solid. $^1$H NMR (500 MHz, CD$_3$OD) δ: 8.08 (t, J=2.0 Hz, 1H), 7.67 (d, J=8.0 Hz, 1H), 7.54 (t, J=7.0 Hz, 1H), 7.49 (d, J=7.5 Hz, 1H), 7.4 (d, J=2.0 Hz, 1H), 7.35 (t, J=8.0 Hz, 1H), 7.29-7.24 (m, 2H), 7.01 (d, J=7.0 Hz, 1H), 6.41 (d, J=8.5 Hz, 1H), 4.59 (t, J=4.0 Hz, 1H), 3.89-3.83 (m, 1H), 3.80-3.73 (m, 1H), 3.53 (t, J=6.5 Hz, 4H), 3.52-3.46 (m, 1H), 3.46-3.41 (m, 1H), 2.75 (t, J=7.0 Hz, 2H), 2.04 (quintet, J=3.0 Hz, 4H), 1.86-1.78 (m, 1H), 1.76-1.63 (m, 5H), 1.59-1.48 (m, 5H).

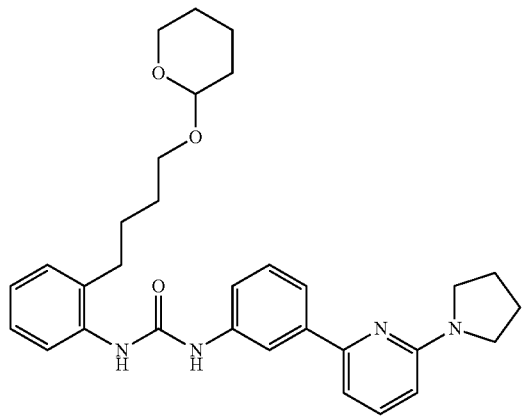

23c 1-(3-(6-(Pyrrolidin-1-yl)pyridin-2-yl)phenyl)-3-(2-(4-((tetrahydro-2H-pyran-2-yl)oxy)butyl)phenyl)urea (23c): Synthesis of 23a gave byproduct 23c (22 mg, 0.043 mmol, 23.3% yield) as a white solid. $^1$H NMR (500 MHz, DMSO) δ: 9.06 (s, 1H), 8.07 (t, J=2.0 Hz, 1H), 7.91 (s, 1H), 7.76 (d, J=8.0 Hz, 1H), 7.62 (d, J=8.0 Hz, 1H), 7.60-7.54 (m, 2H), 7.34 (t, J=8.0 Hz, 1H), 7.18 (d, J=7.5 Hz, 1H), 7.15 (d, J=7.5 Hz, 1H), 7.05 (d, J=7.5 Hz, 1H), 7.01 (t, J=7.5 Hz, 1H), 6.42 (d, J=8.5 Hz, 1H), 4.51 (t, J=3.5 Hz, 1H), 3.70 (tt, J=12.5 Hz, J=3.0 Hz, 1H), 3.66-3.61 (m, 1H), 3.48 (t, J=6.5 Hz, 4H), 3.41-3.34 (m, 2H), 2.63 (t, J=7.0 Hz, 2H), 1.97 (quintet, J=3.0 Hz, 4H), 1.70-1.50 (m, 6H), 1.46-1.32 (m, 4H).

24a

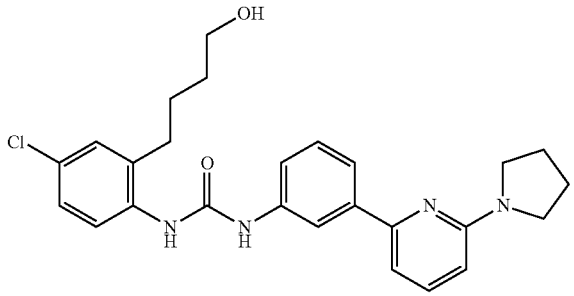

1-(4-Chloro-2-(4-hydroxybutyl)phenyl)-3-(3-(6-(pyrrolidin-1-yl)pyridin-2-yl)phenyl)urea (24a): The synthesis was carried out as described for 22a using 23a (25 mg, 0.046 mmol) in methanol (5 mL) and p-toluenesulfonic acid monohydrate (43.3 mg, 0.228 mmol) to afford the desired product 24a (12 mg, 0.026 mmol, 57% yield) as a white solid.

24b

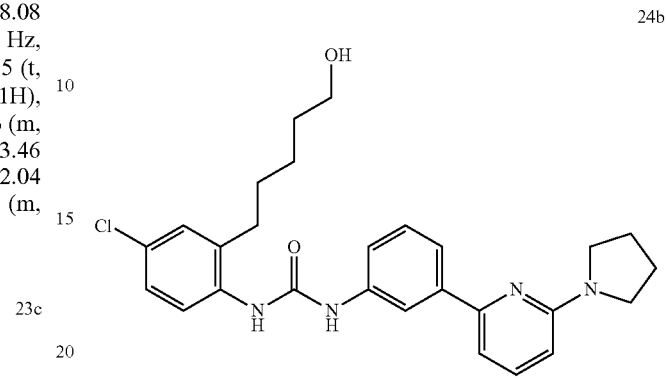

1-(4-Chloro-3-(4-hydroxybutyl)phenyl)-3-(3-(6-(pyrrolidin-1-yl)pyridin-2-yl)phenyl)urea (24b): The synthesis was carried out as described for 22a by adding p-toluenesulfonic acid monohydrate (43.3 mg, 0.228 mmol) and a solution of 23b (25 mg, 0.046 mmol) in methanol (5 mL) to afford the desired product 24b (11 mg, 0.024 mmol, 52% yield) as a white solid. $^1$H NMR (500 MHz, CD$_3$OD) δ: 8.08 (t, J=2.0 Hz, 1H), 7.67 (d, J=8.0 Hz, 1H), 7.64 (t, J=1.5 Hz, 1H), 7.56-7.50 (m, 2H), 7.35 (t, J=8.0 Hz, 1H), 7.23 (d, J=2.5 Hz, 1H), 7.18 (dd, J=9.0 Hz, J=2.5 Hz, 1H), 7.03 (d, J=7.0 Hz, 1H), 6.41 (d, J=8.5 Hz, 1H), 3.60 (t, J=6.0 Hz, 2H), 3.58 (t, J=6.0 Hz, 4H), 2.67 (t, J=7.5 Hz, 2H), 2.04 (quintet, J=3.5 Hz, 4H), 1.73-1.65 (m, 2H), 1.65-1.58 (m, 2H).

Scheme 5: Additional Synthetic Pathways to Formula VI

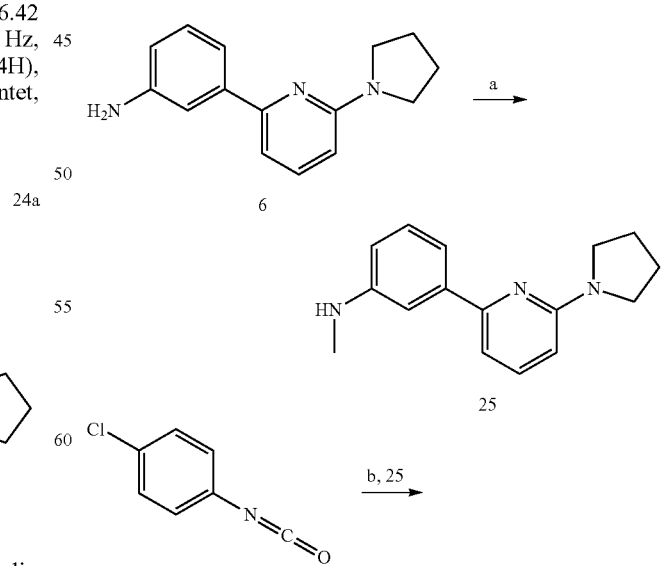

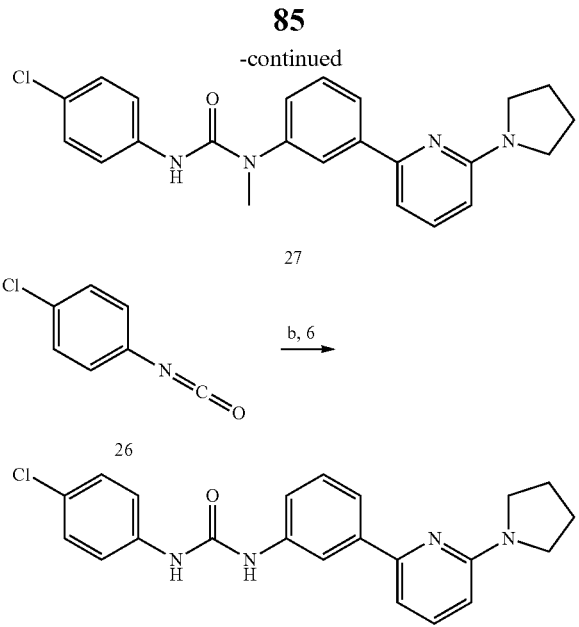

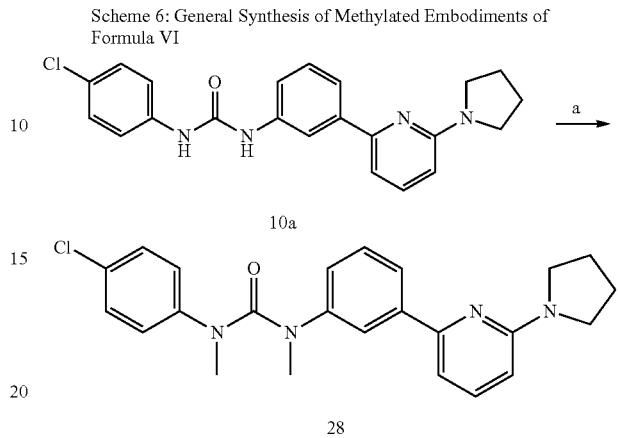

Reagents and Condtions: (a) paraformaldehyde, NaOCH₃, reflux, 3 h, 0° C., NaBH₄, reflux, 1 h, 83% (b) Et₃N, DCM, 0° C., 3 h, 72-85%.

N-Methyl-3-(6-(pyrrolidin-1-yl) pyridin-2-yl)aniline (25): To a solution of 6 (1 g, 4.18 mmol) in methanol (50 mL) was added paraformaldehyde (0.627 g, 20.89 mmol) and sodium methoxide (1.129 g, 20.89 mmol). The reaction mixture was refluxed for 3 h and then was cooled to 0° C. and NaBH₄ (0.790 g, 20.89 mmol) was added. The reaction mixture was heated to reflux for 1 h and then poured into the ice. Aqueous layer was extracted with 50 mL DCM. The organic layer was washed with water (2×50 mL), dried (MgSO₄) and concentrated under reduced pressure. The crude product was purified by silica gel chromatography eluting with 10-50% ethyl acetate:hexanes to afford the desired product 27 (0.88 g, 3.47 mmol, 83% yield) as a colorless oil. ¹H NMR (500 MHz, CD₃OD) δ: 7.47 (dd, J=8.5 Hz, J=7.5 Hz, 1H), 7.31 (t, J=2.0 Hz, 1H), 7.25 (dd, J=7.5 Hz, J=1.0 Hz, 1H), 7.18 (t, J=8.0 Hz, 1H), 6.95 (d, J=7.5 Hz, 1H), 6.64 (ddd, J=7.5 Hz, J=2.0 Hz, J=1.0 Hz, 1H), 6.33 (d, J=8.5 Hz, 1H), 3.48 (t, J=6.0 Hz, 4H), 2.80 (s, 3H), 1.99 (quintet, J=3.0 Hz, 4H). MS m/z (M⁺+1): 254.1

3-(4-Chlorophenyl)-1-methyl-1-(3-(6-(pyrrolidin-1-yl) pyridin-2-yl) phenyl)urea (27): The synthesis was carried out as described for 21a using a solution of 27 (25 mg, 0.099 mmol) in DCM (3 mL), 1-chloro-4-isocyanatobenzene (15.15 mg, 0.099 mmol) followed by Et₃N (0.014 mL, 0.099 mmol) to afford the desired product 29 (29 mg, 0.071 mmol, 72% yield) as a white solid. ¹H NMR (500 MHz, CD₃OD) δ: 7.96 (dd, J=8.5 Hz, J=7.0 Hz, 1H), 7.77 (d, J=2.0 Hz, 1H), 7.68 (d, J=8.0 Hz, 1H), 7.64 (t, J=8.0 Hz, 1H), 7.57 (dd, J=8.0 Hz, J=2.0 Hz, 1H), 7.39 (d, J=9.0 Hz, 2H), 7.25 (d, J=8.5 Hz, 2H), 7.06 (d, J=7.5 Hz, 1H), 7.04 (d, J=9.0 Hz, 1H), 3.68 (t, J=7.0 Hz, 4H), 3.44 (s, 3H), 2.15 (quintet, J=3.0 Hz, 4H).

1-(4-Chlorophenyl)-3-(3-(6-(pyrrolidin-1-yl)pyridin-2-yl)phenyl)urea (10a): To the solution of 6 in DCM (10 mL) was added 1-chloro-4-isocyanatobenzene (321 mg, 2.089 mmol) followed by Et₃N (0.582 mL, 4.18 mmol) and stirred at room temperature for 16 hrs. Reaction was concentrated under reduced pressure and crude was dissolved in methanol. DCM was added and stirred for 30 min to obtain a precipitate. The precipitate was collected by filtration to give desired product 10a (700 mg, 1.77 mmol, 85% yield) as a white solid.

Scheme 6: General Synthesis of Methylated Embodiments of Formula VI

Reagents and Conditions: (a) CH₃I, NaH, DMF, 0° C., 3 h, 78%

1-(4-Chlorophenyl)-1,3-dimethyl-3-(3-(6-(pyrrolidin-1-yl)pyridin-2-yl)phenyl)urea (28): To the solution of 10a (50 mg, 0.127 mmol) in DMF (3 mL) was added NaH (9.16 mg, 0.382 mmol) at 0° C. and stirred for 30 min. To the reaction mixture was added iodomethane (0.018 mL, 0.280 mmol) and stirred for 3 hrs. The reaction mixture was diluted in 20 mL DCM and 20 mL water. The organic layer was separated, washed with water (2×20 mL) and brine, dried (MgSO₄) and concentrated under reduced pressure. The crude product was purified by silica gel chromatography using 10-50% ethyl acetate:hexanes to afford the desired product 10a (42 mg, 0.100 mmol, 78% yield) as a white solid. ¹H NMR (500 MHz, CD₃OD) δ: 7.96 (dd, J=9.0 Hz, J=2.0 Hz, 1H), 7.38 (t, J=1.5 Hz, 1H), 7.37 (d, J=1.5 Hz, 1H), 7.19 (dd, J=5.5 Hz, J=2.0 Hz, 1H), 7.17 (br s, 1H), 7.10 (d, J=2.0 Hz, 1H), 7.08 (d, J=2.0 Hz, 1H), 7.06 (s, 1H), 6.87 (dd, J=7.0 Hz, J=2.0 Hz, 2H), 6.82 (d, J=7.0 Hz, 1H), 3.68 (t, J=7.0 Hz, 4H), 3.23 (s, 3H), 3.20 (s, 3H), 2.16 (quintet, J=3.5 Hz, 4H).

Scheme 7: General Synthesis of Carbamate Embodiments of Formula VI

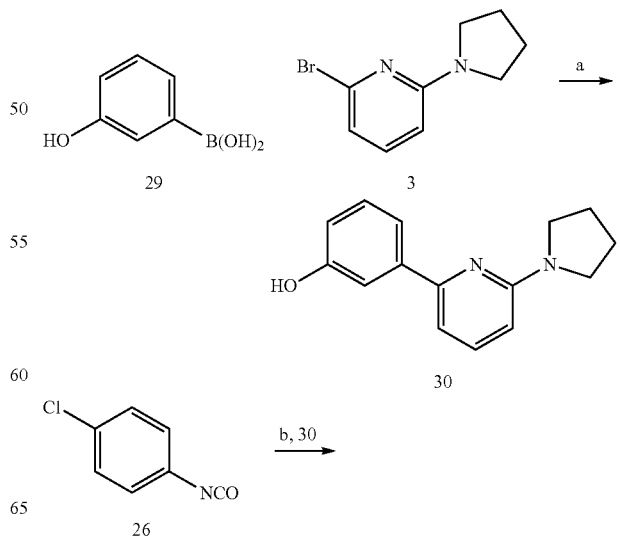

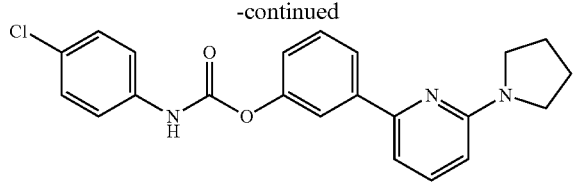

31

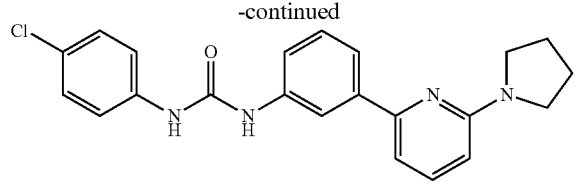

32

Reagents and Conditions: (a) Pd(PPh3)4, NaHCO3, DME, reflux, overnight, 79%; (b) Et3N, DCM, 0° C., 3 h, 61%.

Reagents and Conditions: (b) Et3N, DCM, 40° C., 3 h, 56%.

3-(6-(Pyrrolidin-1-yl)pyridin-2-yl)phenol (30): To a solution of 2-bromo-6-(pyrrolidin-1-yl)pyridine (3 g, 13.21 mmol) and 3-hydroxyphenylboronic acid (1.822 g, 13.21 mmol) in 1,2-dimethoxyethane (22 mL) was added sodium bicarbonate (3.33 g, 39.6 mmol) and water (22 mL). Argon was bubbled through the reaction solution for 2 min. Pd(Ph$_3$P)$_4$ (0.153 g, 0.132 mmol) was added to the reaction mixture and heated to reflux for 4 h. The reaction mixture was diluted with 100 mL ethyl acetate and 100 mL water. The organic layer was separated, washed with 2×50 mL water and brine, dried over MgSO$_4$ and concentrated under reduced pressure. The crude product was purified using silica gel chromatography by eluting with 2-70% ethyl acetate:hexanes to afford 32 (2.52 g, 10.49 mmol, 79% yield). $^1$H NMR (500 MHz, CD$_3$OD) δ: 7.55-7.45 (m, 2H), 7.43 (d, J=8.0 Hz, 1H), 7.22 (t, J=8.0 Hz, 1H), 6.96 (dd, J=7.5 Hz, J=5.5 Hz, 1H), 6.79 (d, J=7.5 Hz, 1H), 6.40-6.32 (m, 1H), 3.50 (br s, 4H), 2.0 (br s, 4H).

3-(6-(Pyrrolidin-1-yl)pyridin-2-yl)phenyl (4-chlorophenyl)carbamate (31): To a solution 30 (25 mg, 0.104 mmol) in DCM (3 mL) was added 1-chloro-4-isocyanatobenzene (15.98 mg, 0.104 mmol) and stirred at 0° C. for 16 h. Reaction was diluted in 20 mL DCM and 20 mL water. The organic layer was separated, washed with water (2×20 mL), dried (MgSO$_4$) and concentrated under reduced pressure. The crude product was purified using silica gel chromatography by eluting with 10-50% ethyl acetate:hexanes to afford the desired product 33 (25 mg, 0.063 mmol, 61% yield) as a white solid. $^1$H NMR (500 MHz, CD$_3$OD) δ: 7.97 (dd, J=9.0 Hz, J=7.5 Hz, 1H), 7.66 (d, J=2.0 Hz, 1H), 7.65 (dd, J=3.5 Hz, J=2.0 Hz, 1H), 7.62 (d, J=8.5 Hz, 1H), 7.51 (d, J=8.5 Hz, 2H), 7.44 (td, J=7.5 Hz, J=2.0 Hz, 1H), 7.31 (d, J=9.5 Hz, 2H), 7.06 (d, J=4.0 Hz, 1H), 7.05 (d, J=2.5 Hz, 1H), 3.69 (t, J=6.5 Hz, 4H), 2.15 (quintet, J=3.5 Hz, 4H).

Scheme 8: Synthesis of a Thio-Embodiment of Formula VI

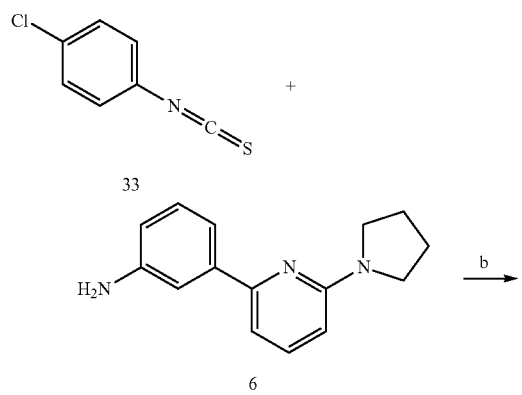

1-(4-Chlorophenyl)-3-(3-(6-(pyrrolidin-1-yl)pyridin-2-yl)phenyl)thiourea (32): To a solution of 6 (25 mg, 0.104 mmol) in DCM (5 mL) was added 1-chloro-4-isothiocyanatobenzene (17.72 mg, 0.104 mmol) followed by Et$_3$N (0.015 mL, 0.104 mmol) and stirred at room temperature for overnight. The reaction was diluted with 20 mL DCM and 20 mL water. The organic layer was separated, washed with water (2×20 mL), dried (MgSO$_4$) and concentrated under reduced pressure. The crude product was purified by silica gel chromatography eluting with 10-50% ethyl acetate:hexanes to afford the desired product 34 (24 mg, 0.059 mmol, 56% yield) as a white solid. $^1$H NMR (500 MHz, CD$_3$OD) δ: 8.03 (s, 1H), 7.94 (dd, J=9.0 Hz, J=7.0 Hz, 1H), 7.60 (td, J=7.0 Hz, J=2.0 Hz, 1H), 7.58-7.51 (m, 2H), 7.48 (d, J=9.0 Hz, 2H), 7.35 (d, J=9.0 Hz, 2H), 7.01 (t, J=8.0 Hz, 2H), 3.66 (t, J=6.0 Hz, 4H), 2.15 (quintet, J=3.0 Hz, 4H).

Scheme 9: Further Embodiments of Formula VI

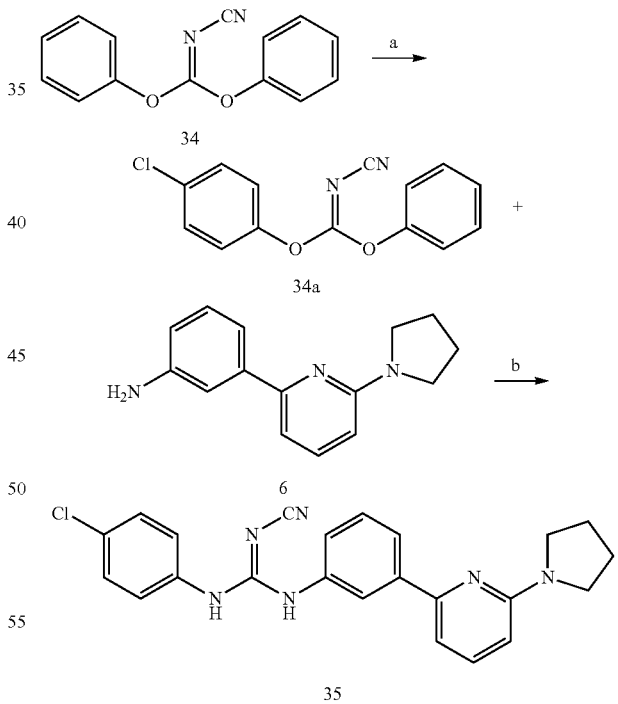

Reagents and Conditions: (a) Acetonitrile, 50° C., overnight, 74%; (b) DMF, microwave ("MW"), 150° C., 1 h, 52%.

(Z)-Phenyl N-(4-chlorophenyl)-N'-cyanocarbamimidate (34a): To a solution of 4-chloroaniline (268 mg, 2.099 mmol) in acetonitrile (21 mL) was added diphenyl cyanocarbonimidate (500 mg, 2.099 mmol) and heated to 50° C. for overnight. The reaction was concentrated and crystallized from 50 mL diethyl ether to afford the desired product 34a (420 mg, 1.546 mmol, 74% yield) as a white solid. $^1$H NMR (500 MHz, DMSO) δ: 10.92 (s, 1H), 7.51 (d, J=8.5 Hz, 2H), 7.48 (t, J=2.5 Hz, 1H), 7.46 (d, J=2.5 Hz, 1H), 7.44 (d, J=8.5 Hz, 2H), 7.33-7.28 (m, 3H).

(Z)-1-(4-Chlorophenyl)-2-cyano-3-(3-(6-(pyrrolidin-1-yl)pyridin-2-yl) phenyl)guanidine (35): 34a (50 mg, 0.184 mmol) and 6 (44.0 mg, 0.184 mmol) were dissolved in DMF (3 mL) and irradiated at 170° C. for 1 h. Major desired product was observed with LC-MS. The reaction mixture was diluted with 20 mL DCM and 20 mL water. The organic layer was separated, washed with water (2×20 mL), dried (MgSO$_4$) and concentrated under reduced pressure. The crude product was purified by silica gel chromatography eluting with 10-50% ethyl acetate:hexanes to afford the desired product 35 (20 mg, 0.048 mmol, 52% yield) as a white solid. $^1$H NMR (500 MHz, CD$_3$OD) δ: 8.0-7.92 (m, 1H), 7.86 (br s, 1H), 7.76 (d, J=8.0 Hz, 1H), 7.64 (t, J=8.0 Hz, 1H), 7.58-7.55 (m, 1H), 7.52 (t, J=2.5 Hz, 1H), 7.51-7.49 (m, 1H), 7.43 (d, J=9.0 Hz, 1H), 7.37 (d, J=2.5 Hz, 1H), 7.07-7.0 (m, 2H), 3.68 (t, J=7.0 Hz, 4H), 2.14 (quintet, J=3.5 Hz, 4H).

mmol) in ethanol (10 mL) was added 3,4-diethoxycyclobut-3-ene-1,2-dione (500 mg, 2.94 mmol) and stirred for 48 h at room temperature. The reaction mixture was concentrated and the product was crystallized by adding 20 mL diethyl ether to afford white solid 39 (668 mg, 2.65 mmol, 90% yield).

3-((4-Chlorophenyl)amino)-4-((3-(6-(pyrrolidin-1-yl)pyridin-2-yl)phenyl)amino)cyclobut-3-ene-1,2-dione (38): To the solution of 37 (25 mg, 0.099 mmol) and 6 (23.77 mg, 0.099 mmol) in DCM (5 mL) was added trimethylaluminum (0.099 mL, 0.099 mmol) at 0° C. and stirred for 1 h. The complete conversion of starting material was observed. The reaction mixture was diluted with 20 mL DCM and 20 mL 10% Rochelle salt solution. The organic layer was separated, washed with water (2×50 mL), dried (MgSO$_4$) and concentrated under reduced pressure. The crude product was purified by silica gel chromatography eluting with 10-50% ethyl acetate:hexanes to afford the desired product 38 (21 mg, 0.047 mmol, 47% yield) as a white solid. $^1$H NMR (500 MHz, CD$_3$OD) δ: 8.35 (s, 1H), 7.88 (t, J=6.0 Hz, 1H), 7.58 (d, J=8.0 Hz, 1H), 7.55-7.50 (m, 3H especially d, 7.53, J=2.5 Hz, 1H), 7.45 (d, J=6.5 Hz, 1H), 7.36 (d, J=9.0 Hz, 2H), 7.13 (d, J=7.0 Hz, 1H), 6.95-6.88 (m, 1H), 3.71 (br s, 4H), 2.15 (quintet, J=3.5 Hz, 4H).

Scheme 10: General Procedure for Certain Embodiments of Formula III

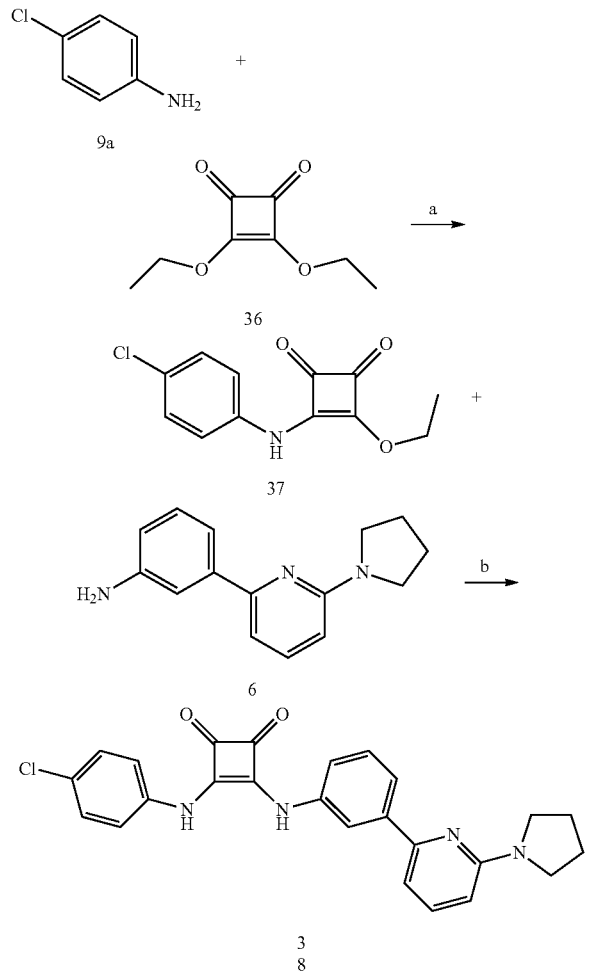

Reagents and Conditions : (a) ethanol, RT, 48 h, 90%; (b) AlMe$_3$, DMC, 0° C., 1 h, 47%.

3-((4-Chlorophenyl)amino)-4-ethoxycyclobut-3-ene-1,2-dione (37): To a solution of 4-chloroaniline (375 mg, 2.94

Scheme 11: General Procedure for Certain Embodiments of Formula IV

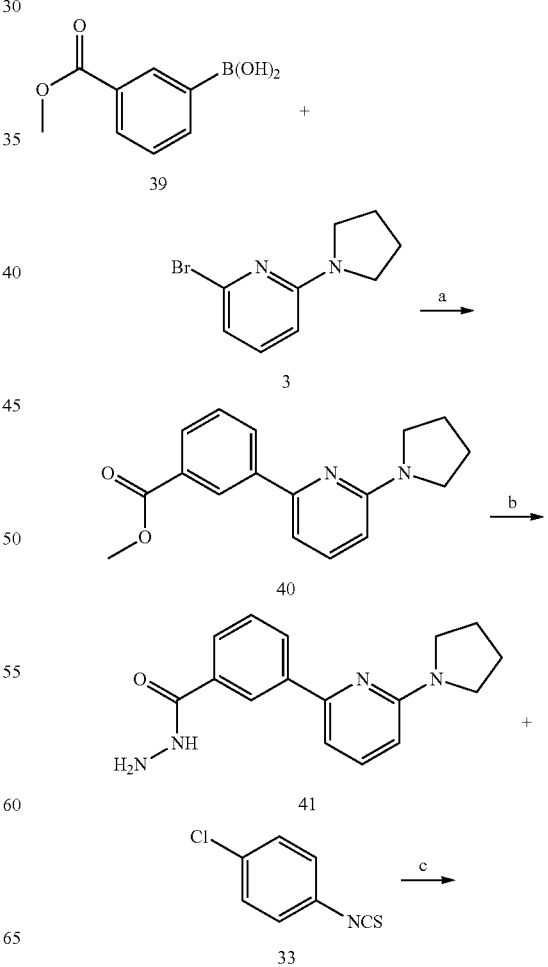

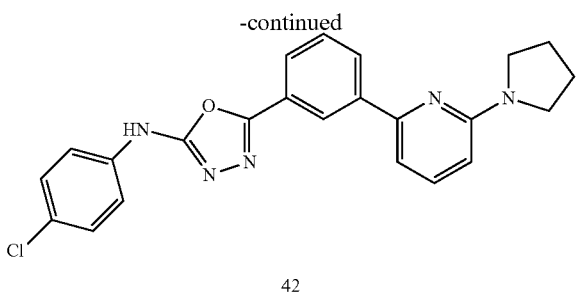

42

Reagents and Conditions: (a) Pd(PPh3)4, NaHCO3, DME, reflux, overnight, 68%; (b) hydrazine, ethanol, reflux, overnight; (c) THF, reflux, overnight, 38%.

Methyl 3-(6-(pyrrolidin-1-yl)pyridin-2-yl)benzoate (40): To a solution of 2-bromo-6-(pyrrolidin-1-yl)pyridine (250 mg, 1.101 mmol) and 3-(methoxycarbonyl) phenylboronic acid (198 mg, 1.101 mmol) in 1,2-dimethoxyethane (5 mL) was added sodium bicarbonate (185 mg, 2.202 mmol) and Water (5 mL). Argon was bubbled through reaction solution for 5 min. Pd(Ph3P)4 (6.36 mg, 5.50 µmol) was added to the reaction mixture and heated to reflux for 6 hrs. Reaction was diluted with 50 mL ethyl acetate and 50 mL water. The organic layer was separated, washed with 2×50 mL water, dried over MgSO4 and concentrated under reduced pressure. Crude product was purified by silica gel chromatography eluting with 2-70% ethyl acetate:hexanes to afford the desired product 40 (210 mg, 0.744 mmol, 68% yield) as a white solid. $^1$H NMR (500 MHz, CD$_3$OD) δ: 8.38 (t, J=2.0 Hz, 1H), 8.23 (td, J=7.5 Hz, J=1.5 Hz, 1H), 8.02-7.97 (m, 2H), 7.71 (t, J=8.0 Hz, 1H), 7.08 (t, J=8.0 Hz, 2H), 3.96 (s, 3H), 3.71 (t, J=7.0 Hz, 4H), 2.17 (quintet, J=3.5 Hz, 4H).

3-(6-(Pyrrolidin-1-yl)pyridin-2-yl)benzohydrazide (41): To a solution of 40 (100 mg, 0.354 mmol) in ethanol (5 mL) was added hydrazine hydrate (0.056 mL, 1.771 mmol) and refluxed for 6 h. The reaction was concentrated under reduced pressure to afford 41 and carried to the next step without any purification. $^1$H NMR (500 MHz, DMSO) δ: 9.87 (s, 1H), 8.45 (t, J=1.5 Hz, 1H), 8.20 (td, J=8.0 Hz, J=1.5 Hz, 1H), 7.82 (td, J=8.0 Hz, J=1.5 Hz, 1H), 7.59 (t, J=8.0 Hz, 1H), 7.52 (t, J=8.0 Hz, 1H), 7.19 (d, J=7.5 Hz, 1H), 6.44 (d, J=8.0 Hz, 1H), 4.58 (s, 2H, NH$_2$), 3.48 (t, J=6.0 Hz, 4H), 1.97 (quintet, J=3.0 Hz, 4H).

N-(4-Chlorophenyl)-5-(3-(6-(pyrrolidin-1-yl)pyridin-2-yl)phenyl)-1,3,4-oxadiazol-2-amine (42): A mixture of 41 (25 mg, 0.089 mmol) and 1-chloro-4-isothiocyanatobenzene (15.0 mg, 0.089 mmol) in THF (2 mL) was heated at refluxed for overnight. The reaction was concentrated under reduced pressure and crude product was purified by silica gel chromatography eluting with 10-50% ethyl acetate: hexanes to afford the desired product 42 (14 mg, 0.034 mmol, 38% yield) as a white solid. $^1$H NMR (500 MHz, CD$_3$OD+CDCl$_3$) δ: 8.62 (t, J=1.0 Hz, 1H), 8.17 (dd, J=3.0 Hz, J=1.0 Hz, 1H), 7.97 (td, J=2.5 Hz, J=1.5 Hz, 1H), 7.59 (dt, J=7.5 Hz, J=1.0 Hz, 1H), 7.55 (dd, J=7.0 Hz, J=2.0 Hz, 2H), 7.34 (dd, J=6.5 Hz, J=2.5 Hz, 2H), 7.08 (d, J=7.5 Hz, 1H), 6.43 (d, J=8.0 Hz, 1H), 3.58 (t, J=6.5 Hz, 4H), 1.70 (quintet, J=3.0 Hz, 4H).

Scheme 12: General Procedure for Certain Embodiments of Formula V

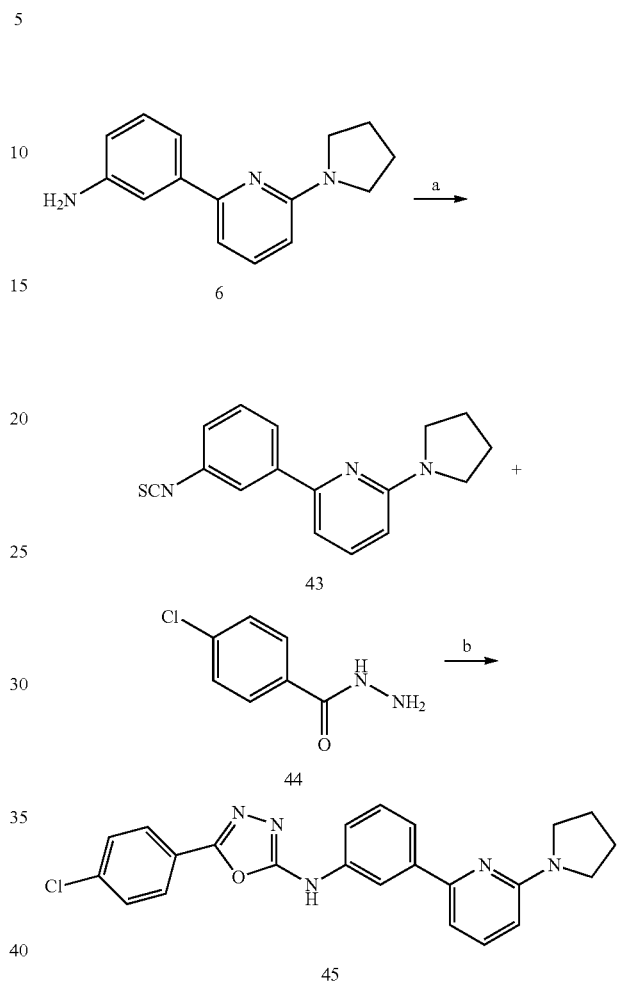

Reagents and Conditions: (a) thiophosgene, DCM, RT; (b) THF, reflux, overnight, 30%.

2-(3-Isothiocyanatophenyl)-6-(pyrrolidin-1-yl)pyridine (43): To a solution of 6 (100 mg, 0.418 mmol) in DCM (5 mL) was added thiophosgene (0.032 mL, 0.418 mmol) at 0° C. and stirred for 3 h. The reaction mixture was concentrated under reduced pressure to afford the desired product 43 (80 mg, 0.284 mmol, 68% yield) which was carried to the next step without purification.

5-(4-Chlorophenyl)-N-(3-(6-(pyrrolidin-1-yl)pyridin-2-yl)phenyl)-1,3,4-oxadiazol-2-amine (45): A mixture of 43 (25 mg, 0.089 mmol) and 4-chlorobenzohydrazide (15 mg, 0.089 mmol) in THF (2 mL) was heated at refluxed for overnight. The reaction was concentrated under reduced pressure and the crude product was purified by silica gel chromatography eluting with 10-50% ethyl acetate:hexanes to afford the desired product 45 (11 mg, 0.026 mmol, 30% yield) as a white solid. $^1$H NMR (500 MHz, CD3OD+CDCl$_3$) δ: 8.26 (d, J=1.5 Hz, 1H), 7.97 (dd, J=6.5 Hz, J=2.0 Hz, 2H), 7.71 (dd, J=6.5 Hz, J=1.0 Hz, 1H),), 7.65-7.50 (m, 4H), 7.44 (t, J=8.0 Hz, 1H), 7.08 (d, J=8.0 Hz, 1H), 6.44 (d, J=8.0 Hz, 1H), 4.28 (t, J=6.5 Hz, 3H), 3.85 (t, J=5.0 Hz, 4H), 3.61 (t, J=5.0 Hz, 4H).

Scheme 13: Synthetic Procedure for Certain Embodiments of Formula VI

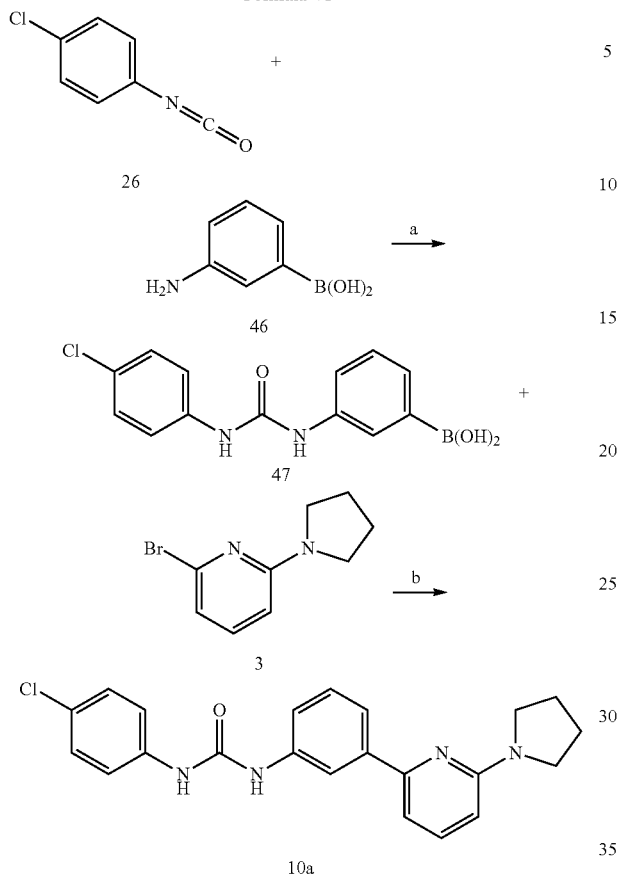

Reagents and Conditions: (a) DMF, RT, 3 h, 53%; (b) Pd(PPh₃)₄, NaHCO₃, DME, reflux, overnight, 62%.

(3-(3-(4-Chlorophenyl)ureido)phenyl)boronic acid (47): To a solution of 3-aminophenylboronic acid (250 mg, 1.826 mmol) in DCM (10 mL) was added 1-chloro-4-isocyanato-benzene (280 mg, 1.826 mmol) at room temperature. Poor solubility of starting material was observed. DMF (10 mL) was added to the reaction mixture to obtained clear solution and stirred for 3 h at room temperature. The reaction mixture was diluted with 50 mL DCM and 50 mL water. The organic layer was separated, washed with water (2×50 mL), dried (MgSO₄) and concentrated under reduced pressure. The crude product was purified by silica gel chromatography eluting with 10-50% ethyl acetate:hexanes to afford the desired product 47 (280 mg, 0.964 mmol, 53% yield). ¹H NMR (500 MHz, DMSO) δ: 8.77 (s, 1H), 8.60 (s, 1H), 8.01 (s, 2H), 7.67 (s, 1H), 7.60 (dd, J=8.0 Hz, J=1.0 Hz, 1H), 7.49 (d, J=9.0 Hz, 2H), 7.41 (d, J=7.0 Hz, 1H), 7.32 (d, J=9.0 Hz, 2H), 7.25 (t, J=7.0 Hz, 1H).

1-(4-Chlorophenyl)-3-(3-(6-(pyrrolidin-1-yl)pyridin-2-yl)phenyl)urea (10a): To a solution of 47 (500 mg, 1.721 mmol) and 3 (391 mg, 1.721 mmol) in 1,2-dimethoxyethane (10 mL) was added sodium bicarbonate (289 mg, 3.44 mmol) and water (10.00 mL). Argon was bubbled through reaction solution for 5 min. Pd(Ph₃P)₄ (9.94 mg, 8.61 μmol) was added to the reaction mixture and heated to refluxed for 4 hrs. The reaction was diluted with 50 ml ethyl acetate and 50 ml water. The organic layer was separated, washed with 2×50 ml water, dried over MgSO₄ and concentrated under reduced pressure. Crude product was purified by silica gel chromatography eluting with 10-90% ethyl acetate:hexanes to give 10a (420 mg, 1.069 mmol, 62% yield) as a white solid.

Scheme 14: Alternate Procedure for Certain Embodiments of Formula VI

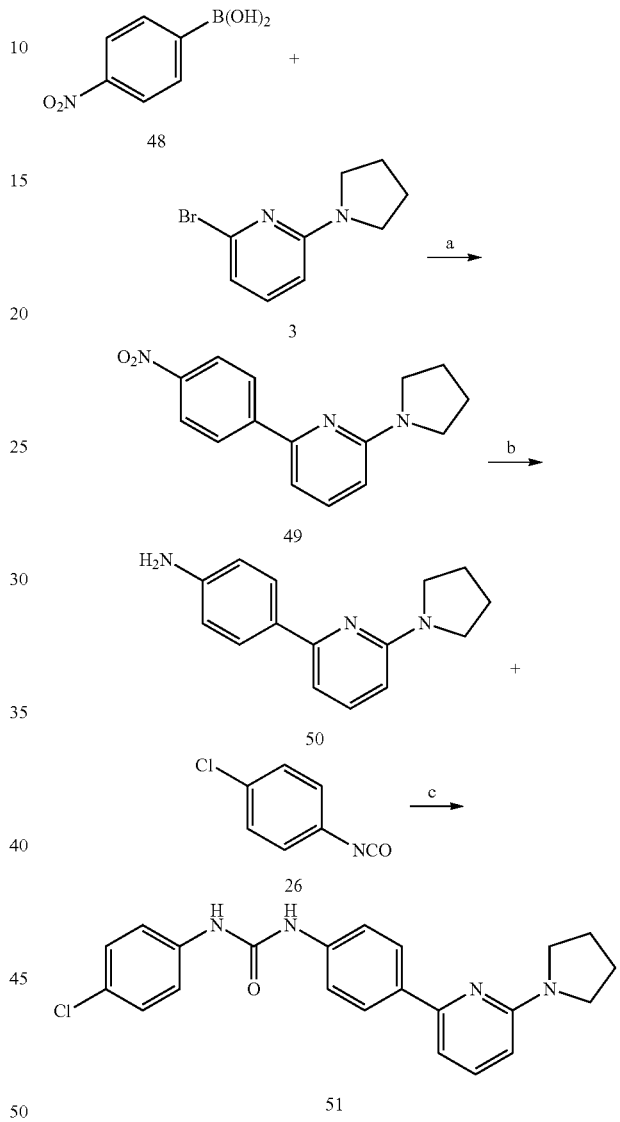

Reagents and Conditions: (a) Pd(PPh₃)₄, NaHCO₃, DME, reflux, overnight, 81%. (b) H₂, Pd/C, cat. acetic acid, ethanol, THF, RT, overnight, 84%; (c) Et₃N, DCM, 0°C., 3 h, 34%.

2-(4-Nitrophenyl)-6-(pyrrolidin-1-yl)pyridine (49): To a solution of 2-bromo-6-(pyrrolidin-1-yl)pyridine (250 mg, 1.101 mmol) and 4-nitrophenylboronic acid (184 mg, 1.101 mmol) in 1,2-dimethoxyethane (5 mL) was added sodium bicarbonate (185 mg, 2.202 mmol) and water (5 mL). Argon was bubbled through the reaction solution for 5 min. Pd(Ph₃P)₄ (6.36 mg, 5.50 μmol) was added to the reaction mixture and heated to reflux for 6 h. The reaction mixture was diluted with 50 mL ethyl acetate and 50 mL water. The organic layer was separated, washed with 2×50 mL water and brine, dried over MgSO₄ and concentrated under reduced pressure. The crude product was purified by silica gel chromatography eluting with 2-70% ethyl acetate:

hexanes to give 51 (240 mg, 0.891 mmol, 81% yield) as a yellow solid. ¹H NMR (500 MHz, DMSO) δ: 8.33-8.26 (m, 4H), 7.63 (dd, J=8.0 Hz, J=7.0 Hz, 1H), 7.27 (d, J=7.5 Hz, 1H), 6.52 (d, J=8.0 Hz, 1H), 3.47 (t, J=6.0 Hz, 4H), 1.97 (quintet, J=3.0 Hz, 4H).

4-(6-(Pyrrolidin-1-yl)pyridin-2-yl)aniline (50): To the solution of 2-(4-nitrophenyl)-6-(pyrrolidin-1-yl)pyridine (100 mg, 0.371 mmol) in ethanol (20 mL) and THF (10 mL) was added Pd/C (3.95 mg, 3.71 µmol) under argon atmosphere. Catalytic Acetic acid was added to the reaction mixture and stirred for overnight under hydrogen gas atmosphere under balloon pressure. Pd/C was filtered off and the filtrate was concentrated and was purified by silica gel chromatography eluting with 2-70% ethyl acetate:hexanes to give 50 (75 mg, 0.313 mmol, 84% yield) as a light yellow oil. ¹H NMR (500 MHz, DMSO) δ: 7.75 (d, J=8.5 Hz, 2H), 7.44 (t, J=8.0 Hz, 1H), 6.91 (d, J=7.5 Hz, 1H), 6.59 (d, J=8.5 Hz, 2H), 6.23 (d, J=8.0 Hz, 1H), 5.29 (s, 2H), 3.43 (t, J=6.5 Hz, 4H), 1.95 (quintet, J=3.0 Hz, 4H).

1-(4-Chlorophenyl)-3-(4-(6-(pyrrolidin-1-yl)pyridin-2-yl)phenyl)urea (51): A mixture of 50 (25 mg, 0.104 mmol), Et₃N (0.044 mL, 0.313 mmol) and 1-chloro-4-isocyanatobenzene (16.04 mg, 0.104 mmol) in THF (3 mL) was stirred at room temperature for 3 h under inert atmosphere. Reaction mixture was concentrated and purified by silica gel chromatography eluting with 10-50% ethyl acetate:hexanes to afford the desired product 51 (14 mg, 0.036 mmol, 34% yield) as a white solid. ¹H NMR (500 MHz, CD₃OD) δ: 7.96 (d, J=9.5 Hz, 2H), 7.53-7.48 (m, 3H), 7.44 (dd, J=7.0 Hz, J=2.0 Hz, 2H), 7.28 (dd, J=6.5 Hz, J=2.0 Hz, 2H), 7.0 (d, J=2.5 Hz, 1H), 6.36 (d, J=8.5 Hz, 1H), 3.53 (t, J=7.0 Hz, 4H), 2.04 (quintet, J=3.5 Hz, 4H).

Scheme 15: Additional Synthetic Routes to Embodiments of Formula I

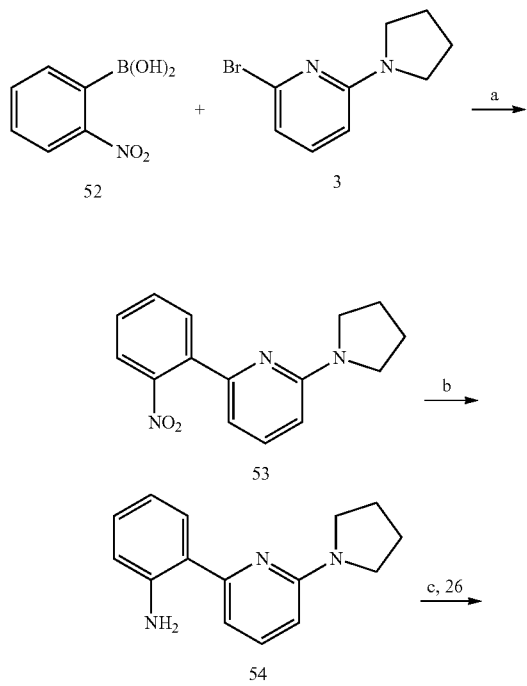

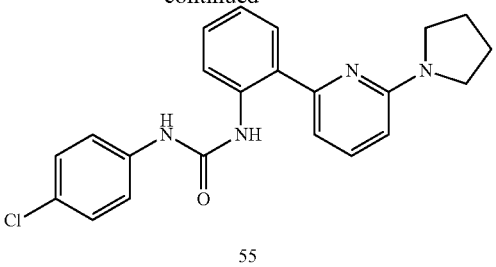

Reagents and Conditions: (a) Pd(PPh₃)₄, NaHCO₃, DME, reflux, overnight, 78%; (b) H₂, Pd/C, cat. acetic acid, ethanol, THF, RT, overnight, 90%; (c) Et₃N, DCM, 0° C., 3 h, 54%.

2-(2-Nitrophenyl)-6-(pyrrolidin-1-yl)pyridine (53): To a solution of 3 (250 mg, 1.101 mmol) and 2-nitrophenylboronic acid (184 mg, 1.101 mmol) in 1,2-Dimethoxyethane (5 mL) was added sodium bicarbonate (185 mg, 2.202 mmol) and water (5 mL). Argon was bubbled through reaction solution for 5 min. Pd(Ph₃P)₄ (6.36 mg, 5.50 µmol) was added to the reaction mixture and heated to refluxed for 6 h. The reaction mixture was diluted with 50 mL ethyl acetate and 50 mL water. The organic layer was separated, washed with 2×50 mL water and brine, dried over MgSO₄ and concentrated under reduced pressure. The crude product was purified by silica gel chromatography eluting with 2-70% ethyl acetate:hexanes to give 55 (230 mg, 0.854 mmol, 78% yield) as a yellow solid. ¹H NMR (500 MHz, CD₃OD) δ: 8.29 (dd, J=8.0 Hz, J=1.0 Hz, 1H), 7.96 (dd, J=8.5 Hz, J=6.5 Hz, 1H), 7.89 (dt, J=8.0 Hz, J=1.5 Hz, 1H), 7.83 (dt, J=8.0 Hz, J=1.5 Hz, 1H), 7.70 (dd, J=8.0 Hz, J=1.5 Hz, 1H), 7.09 (d, J=9.5 Hz, 1H), 6.84 (d, J=7.5 Hz, 1H), 3.59 (t, J=7.0 Hz, 4H), 2.14 (quintet, J=3.5 Hz, 4H).

2-(6-(Pyrrolidin-1-yl)pyridin-2-yl)aniline (54): The reaction was carried out similar to 50 using a solution of 53 (100 mg, 0.371 mmol) in ethanol (20 mL) and THF (10 mL), Pd/C (3.95 mg, 3.71 µmol) and catalytic acetic acid under hydrogen gas atmosphere under balloon pressure to afford 54 (80 mg, 0.334 mmol, 90% yield) as a light yellow oil. ¹H NMR (500 MHz, DMSO) δ: 7.92 (dd, J=8.5 Hz, J=7.0 Hz, 1H), 7.46 (dd, J=7.5 Hz, J=1.5 Hz, 1H), 7.34 (dt, J=8.5 Hz, J=1.5 Hz, 1H), 7.06-6.99 (m, 3H), 6.91 (d, J=9.5 Hz, 1H), 3.60 (t, J=6.5 Hz, 4H), 2.14 (quintet, J=3.5 Hz, 4H).

1-(4-Chlorophenyl)-3-(2-(6-(pyrrolidin-1-yl)pyridin-2-yl)phenyl)urea (55): A mixture of 54 (25 mg, 0.104 mmol) and 1-chloro-4-isocyanatobenzene (16.04 mg, 0.104 mmol) was stirred at room temperature for 3 h under inert atmosphere. The reaction mixture was concentrated and purified by silica gel chromatography eluting with 10-50% ethyl acetate:hexanes to afford the desired product 55 (22 mg, 0.056 mmol, 54% yield) as a white solid. ¹H NMR (500 MHz, CD₃OD) δ: 7.95 (dd, J=9.5 Hz, J=7.5 Hz, 1H), 7.68 (dd, J=8.5 Hz, J=1.5 Hz, 1H), 7.57 (dt, J=8.0 Hz, J=2.0 Hz, 1H), 7.52 (dd, J=8.0 Hz, J=1.5 Hz, 2H), 7.36 (dd, J=7.5 Hz, J=1.0 Hz, 2H), 7.33 (dd, J=6.5 Hz, J=2.0 Hz, 2H), 7.01 (d, J=9.0 Hz, 1H), 6.89 (d, J=7.0 Hz, 1H), 3.59 (t, J=7.0 Hz, 4H), 2.07 (quintet, J=3.5 Hz, 4H).

Scheme 16: Further Routes to Embodiments of Formula I

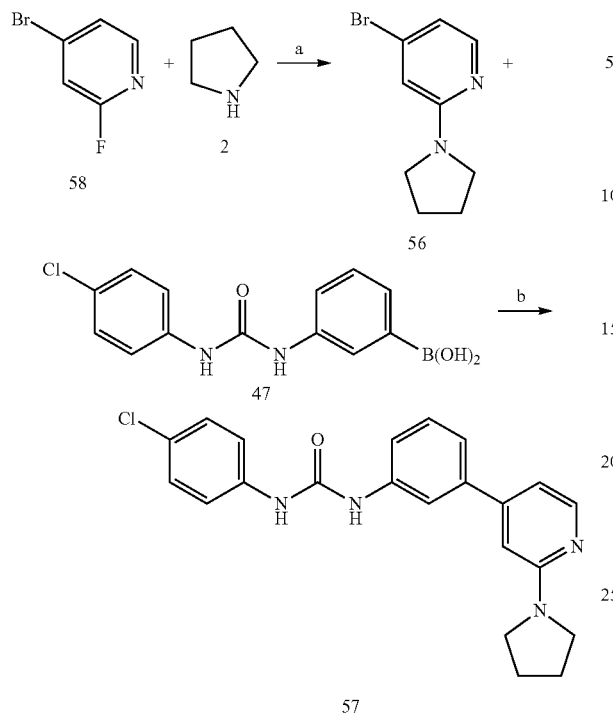

Reagents and Conditions: (a) K₂CO₃, DMF, 100° C., 16 h, 59%. (b) Pd(PPh₃)₄, NaHCO₃, DME, reflux, overnight, 53%.

Scheme 17: Additional Routes to Embodiments of Formula I

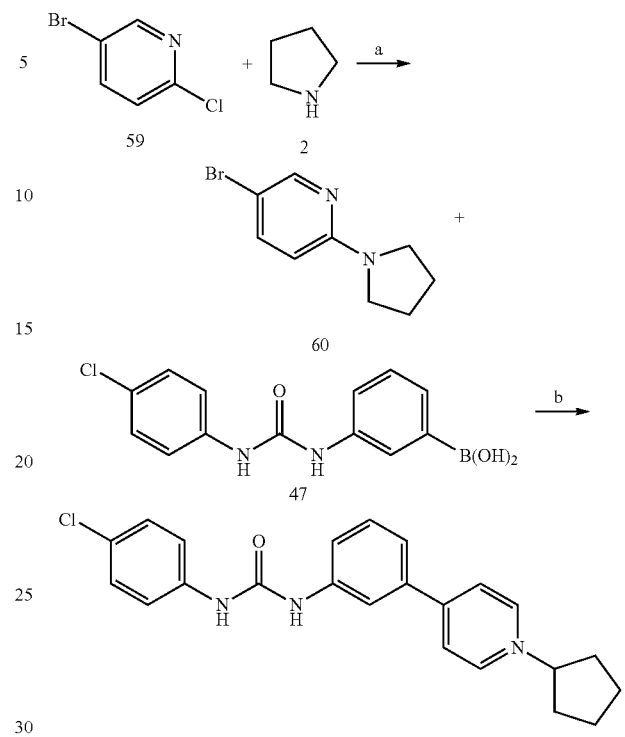

Reagents and Conditions: (a) K₂CO₃, DMF, 100° C., 7 h, 64%; (b) Pd(PPh₃)₄, NaHCO₃, DME, reflux, overnight, 62%.

4-Bromo-2-(pyrrolidin-1-yl)pyridine (56): To a solution of 4-bromo-2-fluoropyridine (250 mg, 1.421 mmol) in DMF (5 mL) was added pyrrolidine (101 mg, 1.421 mmol) followed by K₂CO₃ (196 mg, 1.421 mmol) and heated to 100° C. for 6 h. The reaction mixture was diluted with 50 mL DCM and 50 mL water. The organic layer was separated, washed with water (2×20 mL), dried (MgSO₄) and concentrated under reduced pressure. The crude product was purified by silica gel chromatography eluting with 10-50% ethyl acetate:hexanes to afford the desired product 59 (190 mg, 0.837 mmol, 59% yield). ¹H NMR (500 MHz, DMSO) δ: 7.93 (d, J=5.0 Hz, 1H), 6.71 (dd, J=5.5 Hz, J=1.5 Hz, 1H), 6.62 (d, J=1.5 Hz, 1H),), 3.36 (t, J=6.5 Hz, 4H), 1.92 (quintet, J=3.0 Hz, 4H).

1-(4-Chlorophenyl)-3-(3-(2-(pyrrolidin-1-yl)pyridin-4-yl)phenyl)urea (57): To a solution of 47 (25 mg, 0.086 mmol) and 56 (23.45 mg, 0.103 mmol) in 1,2-dimethoxyethane (3 mL) was added sodium bicarbonate (14.46 mg, 0.172 mmol) and water (3 mL). Argon was bubbled through the reaction solution for 5 min. Pd(Ph₃P)₄ (4.97 mg, 4.30 μmol) was added to the reaction mixture and heated to refluxed for 4 h. The reaction solution was diluted with 20 mL ethyl acetate and 20 mL water. The organic layer was separated, washed with 2×20 mL water, dried over MgSO₄ and concentrated under reduced pressure. The crude product was purified by silica gel chromatography eluting with 2-70% ethyl acetate:hexanes to give 57 (18 mg, 0.046 mmol, 53% yield) as a solid. ¹H NMR (500 MHz, CD₃OD) δ: 8.04 (d, J=5.0 Hz, 1H), 7.85 (td, J=2.0 Hz, 1H), 7.44 (dd, J=7.0 Hz, J=2.0 Hz, 1H), 7.43 (t, J=2.0 Hz, 1H), 7.42-7.40 (m, 1H), 7.38 (d, J=8.5 Hz, 1H), 7.35 (td, J=7.0 Hz, J=1.5 Hz, 1H), 7.28 (dd, J=7.0 Hz, J=2.0 Hz, 2H), 6.83 (dd, J=5.5 Hz, J=1.5 Hz, 1H), 6.68 (d, J=1.0 Hz, 1H), 3.50 (t, J=6.5 Hz, 4H), 2.06 (quintet, J=3.5 Hz, 4H).

5-Bromo-2-(pyrrolidin-1-yl)pyridine (60): To a solution of 5-bromo-2-chloropyridine (500 mg, 2.60 mmol) in DMF (Volume: 3 mL) was added pyrrolidine (222 mg, 3.12 mmol) followed by K₂CO₃ (718 mg, 5.20 mmol) and heated to 100° C. for 7 h. The reaction mixture was diluted with 50 mL DCM and 50 mL water. The organic layer was separated, washed with water (2×50 mL), dried (MgSO₄) and concentrated under reduced pressure. The crude product was purified by silica gel chromatography eluting with 10-50% ethyl acetate:hexanes to afford the desired product 60 (380 mg, 1.673 mmol, 64% yield). ¹H NMR (500 MHz, DMSO) δ: 8.10 (d, J=2.5 Hz, 1H), 7.61 (dd, J=9.0 Hz, J=2.5 Hz, 1H), 6.42 (d, J=9.0 Hz, 1H),), 3.34 (t, J=7.0 Hz, 4H), 1.93 (quintet, J=3.5 Hz, 4H).

1-(4-Chlorophenyl)-3-(3-(6-(pyrrolidin-1-yl)pyridin-3-yl)phenyl)urea (61): To a solution of 47 (50 mg, 0.172 mmol) and 60 (46.9 mg, 0.207 mmol) in 1,2-dimethoxyethane (3 mL) was added sodium bicarboante (28.9 mg, 0.344 mmol) and water (3 mL). Argon was bubbled through reaction solution for 5 min. Pd(Ph₃P)₄ (13.92 mg, 0.012 mmol) was added to the reaction mixture and heated to refluxed for 4 h. The reaction mixture was diluted with 20 mL ethyl acetate and 20 mL water. The organic layer was separated, washed with 2×10 mL water, dried over MgSO₄ and concentrated under reduced pressure. Crude product was purified by silica gel chromatography eluting with 2-70% ethyl acetate:hexanes to give 61 (42 mg, 0.107 mmol, 62% yield) as a white solid. ¹H NMR (500 MHz, CD₃OD) δ: 8.28 (dd, J=9.5 Hz, J=2.5 Hz, 1H), 8.06 (d, J=2.0 Hz, 1H), 7.91 (t, J=2.0 Hz, 1H), 7.45 (dd, J=7.0 Hz, J=2.0 Hz, 2H), 7.42 (t, J=8.0 Hz, 1H), 7.31 (d, J=2.0 Hz, 1H), 7.30-7.28 (m, 2H), 7.27 (d, J=4.0 Hz, 1H), 7.20 (d, J=9.5 Hz, 1H), 3.65 (t, J=6.5 Hz, 4H), 2.19 (quintet, J=3.0 Hz, 4H).

1H), 6.58 (dd, J=8.5 Hz, J=2.0 Hz, 1H), 3.50 (t, J=7.0 Hz, 4H), 2.04 (quintet, J=3.5 Hz, 4H).

Scheme 18: Further Routes to Embodiments of Formula I

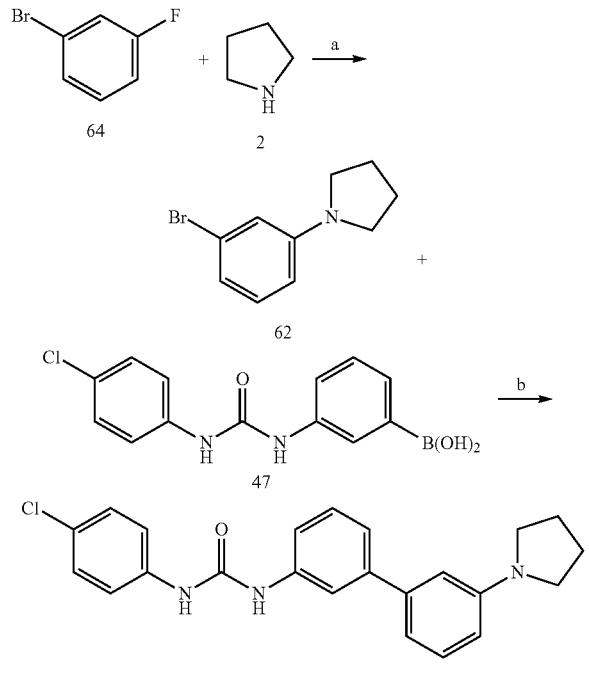

Reagents and Conditions: (a) K₂CO₃, DMF, 100° C., 7 h, 70%; (b) Pd(PPh₃)₄, NaHCO₃, DME, reflux, overnight, 53%.

Scheme 19: Halogentated Variants of Fomula I

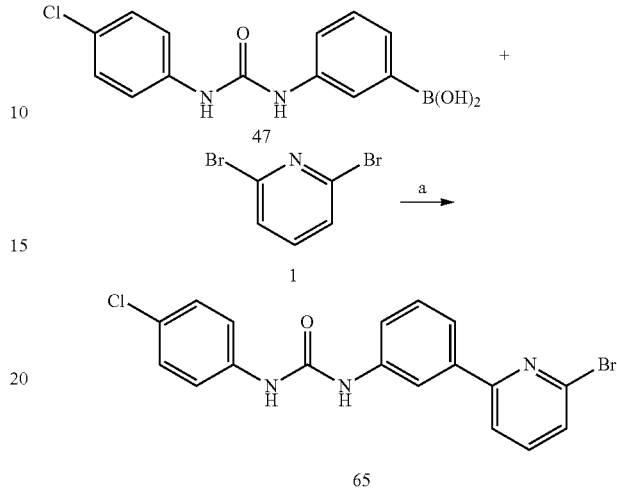

Reagents and Conditions: (a) Pd(PPh₃)₄, NaHCO₃, DME, reflux, overnight, 72%.

1-(3-Bromophenyl)pyrrolidine (62): To a solution of 1-bromo-3-fluorobenzene (250 mg, 1.429 mmol) in DMF (Volume: 5 mL) was added pyrrolidine (122 mg, 1.714 mmol) followed by K₂CO₃ (395 mg, 2.86 mmol) and heated to 100° C. for 7 h. The reaction was diluted with 50 mL DCM and 50 mL water. The organic layer was separated, washed with water (2×20 mL), dried (MgSO₄) and concentrated under reduced pressure. The crude product was purified by silica gel chromatography eluting with 10-50% ethyl acetate:hexanes to afford the desired product 62 (226 mg, 1.000 mmol, 70% yield). ¹H NMR (500 MHz, CD₃OD) δ: 7.02 (t, J=8.0 Hz, 1H), 6.68 (dd, J=8.0 Hz, J=1.0 Hz, 1H), 6.65 (t, J=2.0 Hz, 1H), 6.48 (dd, J=8.5 Hz, J=2.5 Hz, 1H), 3.23 (t, J=6.5 Hz, 4H), 2.01 (quintet, J=3.5 Hz, 4H).

1-(4-Chlorophenyl)-3-(3'-(pyrrolidin-1-yl)-[1,1'-biphenyl]-3-yl)urea (63): To a solution of 47 (25 mg, 0.086 mmol) and 62 (19.46 mg, 0.086 mmol) in 1,2-dimethoxyethane (3 mL) was added sodium bicarbonate (14.46 mg, 0.172 mmol) and Water (3 mL). Argon was bubbled through the reaction solution for 5 min. Pd(Ph₃P)₄ (4.97 mg, 4.30 μmol) was added to the reaction mixture and heated to refluxed for 4 h. The reaction was diluted with 20 mL ethyl acetate and 20 mL water. The organic layer was separated, washed with 2×20 mL water, dried over MgSO₄ and concentrated under reduced pressure. The crude product was purified by silica gel chromatography eluting with 2-70% ethyl acetate: hexanes to give 63 (18 mg, 0.046 mmol, 53% yield) as a solid. ¹H NMR (500 MHz, CD₃OD) δ: 7.70 (t, J=1.5 Hz, 1H), 7.44 (dd, J=2.0 Hz, 2H), 7.36 (td, J=8.5 Hz, J=2.0 Hz, 1H), 7.32 (d, J=8.5 Hz, 1H), 7.30-7.25 (m, 3H), 7.23 (t, J=8.5 Hz, 1H), 6.86 (d, J=7.0 Hz, 1H), 6.78 (d, J=2.0 Hz, 1-(3-(6-Bromopyridin-2-yl)phenyl)-3-(4-chlorophenyl) urea (65): To a solution of 47 (250 mg, 0.861 mmol) and 2,6-dibromopyridine (408 mg, 1.721 mmol) in 1,2-Dimethoxyethane (10 mL) was added sodium bicarbonate (217 mg, 2.58 mmol) and water (10 mL). Argon was bubbled through the reaction solution for 5 min. Pd(Ph₃P)₄ (6.96 mg, 6.02 μmol) was added to the reaction mixture and heated to refluxed for 6 h. The reaction mixture was diluted with 100 mL ethyl acetate and 100 mL water. The organic layer was separated, washed with 2×50 mL water and brine, dried over MgSO₄ and concentrated under reduced pressure. The crude product was purified by silica gel chromatography eluting with 2-70% ethyl acetate:hexanes to give 65 (250 mg, 0.621 mmol, 72.1% yield) as a white solid. ¹H NMR (500 MHz, CD₃OD) δ: 8.10 (t, J=2.0 Hz, 1H), 7.85 (d, J=8.0 Hz, 1H), 7.74 (t, J=8.0 Hz, 1H), 7.67 (td, J=8.0 Hz, J=2.0 Hz, 1H), 7.56 (ddd, J=8.5 Hz, J=2.0 Hz, J=1.0 Hz, 1H), 7.51 (d, J=8.0 Hz, 1H), 7.45 (d, J=9.0 Hz, 2H), 7.43 (t, J=3.0 Hz, 1H), 7.41 (d, J=1.5 Hz, 1H), 7.31-7.27 (m, 2H especially d, 7.28, J=2.0 Hz, 1H).

Scheme 20: Morpholino and Piperazinyl Variants of Formula I

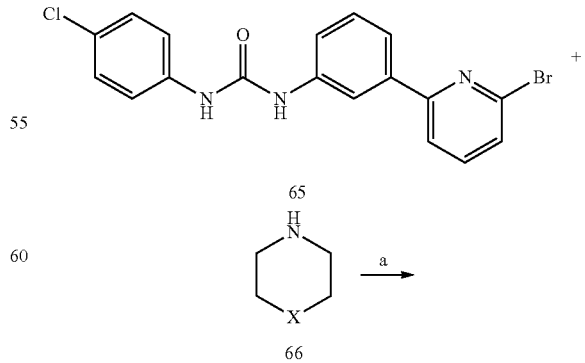

X = O; 66a
X = NH; 66b

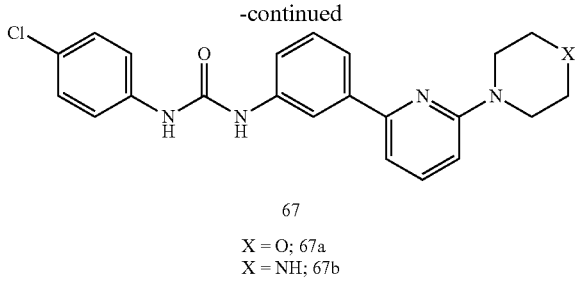

67

X = O; 67a
X = NH; 67b

Reagents and Conditions: (a) CuI, L-proline, t-BuONa, DMF, 100° C., overnight, 32-39%.

1-(4-Chlorophenyl)-3-(3-(6-morpholinopyridin-2-yl)phenyl)urea (67a): To a solution of 65 (25 mg, 0.062 mmol), K₂CO₃ (12.87 mg, 0.093 mmol), L-proline (0.5 mg, 4.35 µmol) and morpholine (8.11 mg, 0.093 mmol) in DMF (Volume: 2 mL) was added copper(I)iodide (0.82 mg, 4.32 µmol) and irradiated at 150° C. for 30 min. The reaction was diluted with 20 mL DCM and 20 mL water. The organic layer was separated, washed with water (2×50 mL), dried (MgSO₄) and concentrated under reduced pressure. The crude product was purified by silica gel chromatography eluting with 10-50% ethyl acetate:hexanes to afford the desired product 70a (10 mg, 0.024 mmol, 39% yield) as a white solid. ¹H NMR (500 MHz, CD3OD+CDCl₃) δ: 8.08 (t, J=2.0 Hz, 1H), 7.70-7.60 (m, 2H), 7.55 (dt, J=8.0 Hz, J=3.5 Hz, 1H), 7.48 (td, J=8.0 Hz, J=1.5 Hz, 1H), 7.46-7.41 (m, 2H), 7.37 (t, J=8.0 Hz, 1H), 7.28 (t, J=3.0 Hz, 1H), 7.20 (d, J=7.5 Hz, 1H), 6.73 (d, J=8.0 Hz, 1H), 3.85 (t, J=5.0 Hz, 4H), 3.61 (t, J=5.0 Hz, 4H).

1-(4-Chlorophenyl)-3-(3-(6-(piperazin-1-yl)pyridin-2-yl)phenyl)urea (67b): The synthesis was carried out similar to 67a using a solution of 65 (25 mg, 0.062 mmol), K₂CO₃ (12.87 mg, 0.093 mmol), L-proline (0.5 mg, 4.35 µmol), copper(I)iodide (0.82 mg, 4.32 µmol) and piperazine (8.0 mg, 0.093 mmol) in DMF (Volume: 2 mL) was added to afford the desired product 70b (8 mg, 0.020 mmol, 32% yield) as a white solid. ¹H NMR (500 MHz, CD₃OD) δ: 8.04 (t, J=1.5 Hz, 1H), 7.66 (td, J=8.0 Hz, J=1.5 Hz, 1H), 7.56 (dd, J=8.5 Hz, J=7.5 Hz, 1H), 7.51 (ddd, J=8.5 Hz, J=2.5 Hz, J=1.0 Hz, 1H), 7.44 (dd, J=7.0 Hz, J=2.0 Hz, 2H), 7.35 (t, J=8.0 Hz, 1H), 7.30 (dd, J=7.0 Hz, J=2.0 Hz, 2H), 7.10 (d, J=8.0 Hz, 1H), 6.71 (d, J=9.0 Hz, 1H), 3.64 (d, J=5.0 Hz, 4H), 1.70 (br s, 4H).

Scheme 21: General Synthetic Routes to Embodiments of Formula II

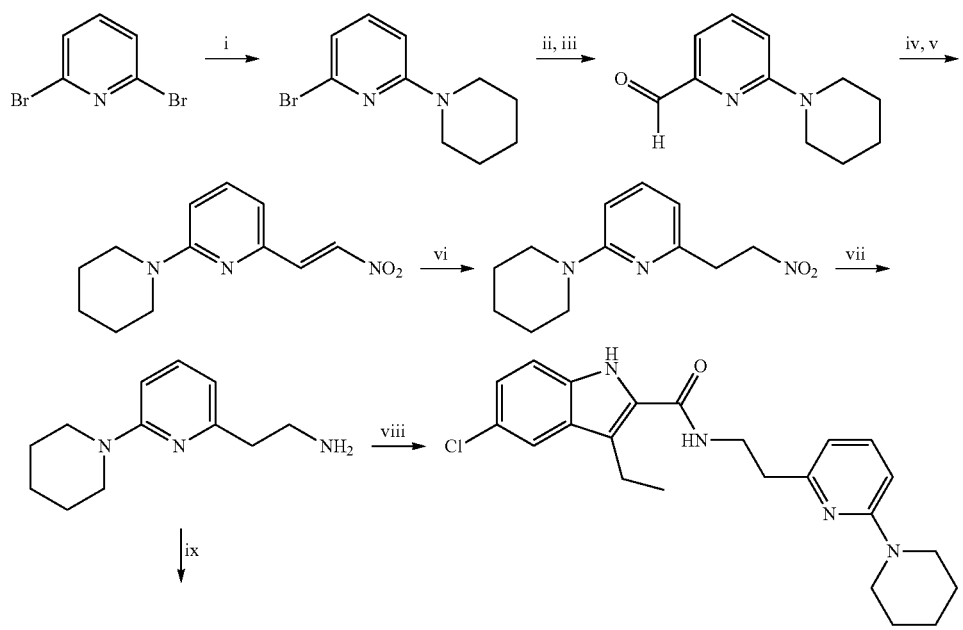

70

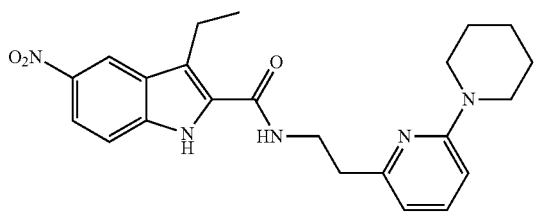

71

Reagents and conditions: i) piperidine, K₃PO₄, dioxan, reflux, 10 h, argon; ii) n-butyl lithium, n-butylmagnesium chloride, anhydrous toluene, -15° C., inert atmosphere; iii) 30% anhydrous DMF in Toluene, -15° C., inert atmosphere; iv) nitromethane, toluene, TMG, 50° C. inert atmosphere, 1 h; v) methanesulfonyl chloride, toluene, 27° C. inert atmosphere, 3 h; vi) NaBH₄, MeOH, 0° C., 3 h; vii) NiCl₂ 6H₂O, NaBH₄, MeOH, -15° C., 3 h; viii) 3-ethyl-5-chloro-1H-indole-2-carboxylic acid, EDCI, Hunig's base, HOBT, dry NMP. argon, RT, 20 h; ix) 3-ethyl-5-nitro-1H-indole-2-carboxylic acid, EDCI, Hunig's base, HOBT, dry NMP. argon, RT, 20 h.

2-bromo-6-(piperidin-1-yl)pyridine: In a 100 mL round bottom flask 2,6-dibromopyridine (1 g, 4.22 mmol), piperidine (0.395 g, 4.64 mmol), anhydrous potassium phosphate (0.896 g, 4.22 mmol) were taken in dry 1,4-Dioxane (Volume: 60 ml) and reaction was heated at 105° C. under inert conditions for 10 hr, cooled to room temp, Complete conversion of starting material was monitored by TLC, on complete conversion of dibromopyridine, solvents were removed under vacuum, residue was diluted with water, partitioned in DCM:Water, washed with brine, the organic layer was dried over sodium sulfate, filtered and conc under vacuum to give crude product, purified by flash chromatography using silica gel column (5:1 Hex/EtOAc; 80 g column) to give pure 2-bromo-6-(piperidin-1-yl)pyridine (894 mg, 3.71 mmol, 88% yield). $^1$H NMR (500 MHz, CDCl$_3$) δ ppm 7.23 (dd, J=8 Hz, J=7 Hz, 1H); 6.6 (d, J=8 Hz, 1H); 6.49 (d, J=8 Hz, 1H); 3.53-3.50 (m, 4H); 1.66-1.59 (m, 6H).

6-(piperidin-1-yl)picolinaldehyde: In a flame dried 250 mL two neck round bottom flask 30 ml anhydrous THF was added and cooled to −15° C. under inert atmosphere. To this was added n-butyl lithium (398 mg, 6.22 mmol) followed by dropwise addition of n-butylmagnesium chloride (315 mg, 2.70 mmol), which was stirred for 0.5 h at −15° C., followed by dropwise addition of a solution of 2-bromo-6-(piperidin-1-yl)pyridine (1000 mg, 4.15 mmol) in 20 ml anhydrous toluene. This mixture was stirred for 1.5 h. To a flame dried 250 ml flask was added 60 mL of anhydrous toluene and 25 ml of anhydrous DMF, then the mixture cooled to −15° C. under inert atmosphere. The THF solution was canulated dropwise into the toluene/DMF mixture with rapid stirring and maintaining internal temperature −10° C. The reaction was allowed to proceed for 3 h at this same temperature, then quenched in a cooled 10% aqueous solution of citric acid at 5° C., stirred for 30 min at 5° C., and diluted with water. The organic layer was separated, the water layer was extracted with toluene, and the combined organic layers were washed with brine and dried over anhydrous sodium sulphate. The organic solvents were removed under vacuum to give the crude product which was purified by flash chromatography using silica gel column (5:1 Hex/EtOAc; 80 g column) to give pure 6-(piperidin-1-yl)picolinaldehyde (702 mg, 3.69 mmol, 89% yield). $^1$H NMR (500 MHz, CDCl$_3$) δ ppm 9.85 (s, 1H); 7.54 (t, J=7.5 Hz, 1H); 7.17 (d, J=7 Hz, 1H); 6.8 (d, J=8.5 Hz, 1H); 3.60-3.56 (m, 4H); 1.66-1.59 (m, 6H).

(E)-2-(2-nitrovinyl)-6-(piperidin-1-yl)pyridine: In a 100 mL round bottom flask 6-(piperidin-1-yl)picolinaldehyde (600 mg, 3.15 mmol), anhydrous nitromethane (578 mg, 9.46 mmol) were dissolved in 30 ml anhydrous toluene followed by addition of 1,1,3,3-tetramethylguanidine (908 mg, 7.88 mmol). The reaction was stirred at 50° C. under inert atmosphere for 1 h to give the intermediate nitro alcohol. The reaction was then cooled to 0° C. followed by dropwise addition of methanesulfonyl chloride (759 mg, 6.62 mmol), then stirred at room temperature for 3 h, and quenched by adding to 100 ml saturated NaHCO$_3$ solution at 0° C. The organic layer was separated, the water layer was extracted 3 times with ethylacetate, and the combined organic layers were washed with brine and dried over sodium sulfate. The organic solution was then filtered and concentrated under vacuum to give the crude product which was purified by flash chromatography using silica gel column (4:1 Hex/EtOAc; 80 g column) to give pure (E)-2-(2-nitrovinyl)-6-(piperidin-1-yl)pyridine (402 mg, 1.723 mmol, 54.6% yield).

2-(2-nitroethyl)-6-(piperidin-1-yl)pyridine: In a 100 mL round bottom flask (E)-2-(2-nitrovinyl)-6-(piperidin-1-yl)pyridine (100 mg, 0.429 mmol) in MeOH (Volume: 30 ml) cooled to −5° C. under inert conditions followed by addition of sodium borohydride (130 mg, 3.43 mmol), the reaction was stirred at 0-5° C. for 3 h, quenched by addition of 40 mL of saturated NH$_4$Cl solution, solvents were removed under vacuum, residue was diluted with water, partitioned in DCM:Water, washed with brine, the organic layer was dried over sodium sulfate, filtered and concentrated under vacuum to give crude product which was purified by flash chromatography using silica gel column (4:1 Hex/EtOAc; 12 g column) to give pure 2-(2-nitroethyl)-6-(piperidin-1-yl)pyridine (82 mg, 0.349 mmol, 81% yield).

2-(6-(piperidin-1-yl)pyridin-2-yl)ethanamine: In a 100 mL round bottom flask 2-(2-nitroethyl)-6-(piperidin-1-yl)pyridine (400 mg, 1.700 mmol), nickel chloride hexahydrate (404 mg, 1.700 mmol) were stirred in 60 ml anhydrous THF:methanol (90:10) at room temperature for 45 min, cooled to −15° C., followed by small portionwise addition of sodium tetrahydroborate (515 mg, 13.60 mmol) upon which the mixture turned black. The reaction was further stirred at −15° C. for 2 h, warmed to room temperature and stirred for 1 h, quenched by addition of 60 ml of saturated NH$_4$Cl solution. The solvents were removed under vacuum, after which the residue was diluted with water, partitioned in DCM:Water, and filtered through a Celite pad. The organic layer was washed with brine, dried over sodium sulfate and concentrated under vacuum to give 2-(6-(piperidin-1-yl)pyridin-2-yl)ethanamine (236 mg, 1.150 mmol, 67.6% yield).

5-chloro-3-ethyl-N-(2-(6-(piperidin-1-yl)pyridin-2-yl)ethyl)-1H-indole-2-carboxamide: In a 50 mL round bottom flask was added 2-(6-(piperidin-1-yl)pyridin-2-yl)ethanamine (35 mg, 0.170 mmol), 5-chloro-3-ethyl-1H-indole-2-carboxylic acid (50 mg, 0.224 mmol), N1-((ethylimino)methylene)-N3,N3-dimethylpropane-1,3-diamine (31.6 mg, 0.203 mmol), 1H-benzo[d][1,2,3]triazol-1-ol (27.5 mg, 0.203 mmol), and N-ethyl-N-isopropylpropan-2-amine (26.3 mg, 0.203 mmol) in 5 mL anhydrous NMP, and the reaction was stirred at room temperature under inert atmosphere for 20 h. The reaction was then diluted with 200 mL cold water, stirred vigorously for 1 h, the solid precipitated out of solution, filtered, washed with ice cold water, and concentrated under vacuum to give the crude product. The crude product was purified by flash chromatography using silica gel column (3:1 Hex/EtOAc; 25 g column) to give pure 5-chloro-3-ethyl-N-(2-(6-(piperidin-1-yl)pyridin-2-yl)ethyl)-1H-indole-2-carboxamide (59 mg, 0.144 mmol, 70.6% yield).

3-ethyl-5-nitro-N-(2-(6-(piperidin-1-yl)pyridin-2-yl)ethyl)-1H-indole-2-carboxamide: To a 50 mL round bottom flask was added 2-(6-(piperidin-1-yl)pyridin-2-yl)ethanamine (50 mg, 0.244 mmol), 3-ethyl-5-nitro-1H-indole-2-carboxylic acid (71.3 mg, 0.304 mmol), N1-((ethylimino)methylene)-N3,N3-dimethylpropane-1,3-diamine (56.7 mg, 0.365 mmol), 1H-benzo[d][1,2,3]triazol-1-ol (32.9 mg, 0.244 mmol), and N-ethyl-N-isopropylpropan-2-amine (63.0 mg, 0.487 mmol) in 10 ml of anhydrous NMP. The reaction was stirred at 25° C. under inert atmosphere for 14 h. The reaction was then diluted with 200 ml cold water, stirred vigorously for 1 h, the solid precipitated out, filtered, washed with ice cold water, and concentrated under vacuum to give the crude product. The crude product was purified by flash chromatography using silica gel column (3:1 Hex/EtOAc; 25 g column) to give pure 3-ethyl-5-nitro-N-(2-(6-(piperidin-1-yl)pyridin-2-yl)ethyl)-1H-indole-2-carboxamide (75 mg, 0.178 mmol, 73.1% yield). $^1$H NMR (500 MHz, CDCl$_3$) δ ppm 1.10 (t, 3H) 1.62 (br. s., 6H) 2.87 (q, J=8 Hz, 2H) 3.02 (t, 2 J=7 Hz H) 3.53 (d, J=5 Hz, 4H) 3.98-4.06 (m, 2H) 6.49 (d, J=7 Hz, 1H) 6.53 (d, J=9 Hz, 1H) 6.92 (br. s., 1H) 7.42 (dd, J=8 Hz, 7 Hz, 1H) 7.45 (d, J=9 Hz, 1H) 8.15 (dd, J=9 Hz, 2 Hz, 1H) 8.60 (d, J=2 Hz, 1H) 10.13 (br. s., 1H).

In Vitro Evaluation:

Cell Handling: cAMP Hunter cell lines were expanded from freezer stocks in T25 flasks according to standard procedures and maintained in selective growth media prior to assay. Once it was established that the cells were healthy and growing normally, cells were passaged from flasks using cell dissociation reagent buffer and seeded into white walled clear bottom 384-well microplates for compound profiling. For profiling, cells were seeded at a density of 10000 cells per well in a total volume of 20 μL and were allowed to adhere and recover overnight prior to compound addition. Cells were treated the following day using the protocols shown below. cAMP modulation was determined using the DiscoveRx HitHunter cAMP XS+ assay.

Media was aspirated from cells and replaced with 10 μL 1:1 HBSS/Hepes: cAMP XS+ Ab reagent. Agonist (CP55, 940) dose curves were performed to determine the $EC_{20}$ value for the testing with the compounds of the present technology. 5 μL of 4× agonist was added to each well with an equal concentration of vehicle present. $EC_{20}$ agonist concentration was determined directly from agonist dose curve.

For allosteric determination, cells were preincubated with compound followed by agonist challenge at the $EC_{20}$ concentration of the agonist. 5 μL of 4× compound was added to cells and incubated at 37° C. for 30 minutes. 5 μL of 4× $EC_{20}$ agonist was added to cells and incubated at 37° C. for 30 minutes.

Signal Detection: After appropriate compound incubation, assay signal was generated through incubation with 20 μL cAMP XS+ED/CL lysis cocktail for one hour followed by incubation with 20 μL cAMP XS+EA reagent for three hours at room temperature. Microplates were read following signal generation with a PerkinElmer Envision™ instrument for chemiluminescent signal detection.

Data Analysis: Dose curves were plotted using GraphPad Prism or Activity Base. The percentage activity is calculated using the following formula:

% Activity=100%×(1−(mean RLU of test sample−mean RLU of MAX control)/(mean RLU of vehicle control [EC20 for PAM]−mean RLU of MAXcontrol).

Agonist (CP55,940) dose curves were performed for the CNR1 PathHunter and cAMP Hunter cell lines. Data shown was normalized to the maximal and minimal response observed in the presence of control ligand and vehicle respectively. The cAMP assay was performed in the presence of 20 μM forskolin ($EC_{80}$).

TABLE 1

| | | cAMP | | β-arrestin | |
|---|---|---|---|---|---|
| Compound No. | Structure | $EC_{50}$ nM | % inhibition | $EC_{50}$ nM | % inhibition |
| 10a | | 231 | 108% | 27 | 109% |
| 10q | | 501 | 135% | 110 | 135% |
| 10c | | 782 | 111% | 260 | 128% |
| 10d | | >10,000 | 39% | 2170 | 105% |

TABLE 1-continued

Biological Activity of Exemplary Compounds

| Compound No. | Structure | cAMP | | β-arrestin | |
|---|---|---|---|---|---|
| | | $EC_{50}$ nM | % inhibition | $EC_{50}$ nM | % inhibition |
| 10e | 4-CF₃-phenyl urea linked to 3-(6-pyrrolidin-1-yl-pyridin-2-yl)phenyl | 218 | 161% | 51 | 128% |
| 10f | 3-CF₃-phenyl urea linked to 3-(6-pyrrolidin-1-yl-pyridin-2-yl)phenyl | 242 | 116% | 220 | 129% |
| 10g | 2-CF₃-phenyl urea linked to 3-(6-pyrrolidin-1-yl-pyridin-2-yl)phenyl | 1156 | 119% | 2091 | 123% |
| 10b | 4-I-phenyl urea linked to 3-(6-pyrrolidin-1-yl-pyridin-2-yl)phenyl | 223 | 126% | 27 | 133% |
| 10t | 4-F-phenyl urea linked to 3-(6-pyrrolidin-1-yl-pyridin-2-yl)phenyl | 148 | 119% | 7 | 108% |
| 10u | 2-F-phenyl urea linked to 3-(6-pyrrolidin-1-yl-pyridin-2-yl)phenyl | 330 | 79% | 99 | 107% |
| 10n | 4-Me-phenyl urea linked to 3-(6-pyrrolidin-1-yl-pyridin-2-yl)phenyl | 764 | 122% | 119 | 127% |
| 10o | 3-Me-phenyl urea linked to 3-(6-pyrrolidin-1-yl-pyridin-2-yl)phenyl | 483 | 65% | 734 | 125% |

TABLE 1-continued

Biological Activity of Exemplary Compounds

| Compound No. | Structure | cAMP EC$_{50}$ nM | % inhibition | β-arrestin EC$_{50}$ nM | % inhibition |
|---|---|---|---|---|---|
| 10p | | 1700 | 97% | 361 | 104% |
| 10h | | 1233 | 97% | 99 | 98% |
| 10i | | 1792 | 92% | 497 | 109% |
| 10j | | >10,000 | 0 | 1227 | 93% |
| 10k | | 750 | 91% | 115 | 123% |
| 10l | | 2241 | 57% | 86 | 117% |

TABLE 1-continued

Biological Activity of Exemplary Compounds

| Compound No. | Structure | cAMP EC$_{50}$ nM | % inhibition | β-arrestin EC$_{50}$ nM | % inhibition |
|---|---|---|---|---|---|
| 10m | 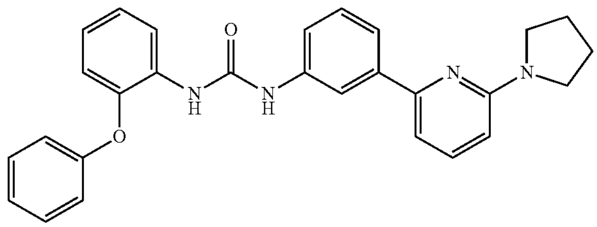 [SMILES: O=C(Nc1cccc(-c2cccc(N3CCCC3)n2)c1)Nc1ccccc1Oc1ccccc1] | >10,000 | 18% | 795 | 80% |
| 10z | 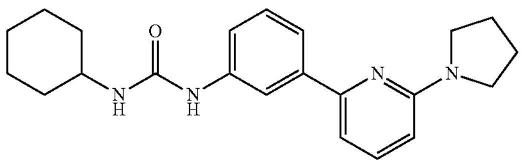 [SMILES: O=C(Nc1cccc(-c2cccc(N3CCCC3)n2)c1)NC1CCCCC1] | 659 | 78% | 333 ± 30 | 136% |
| 10w | 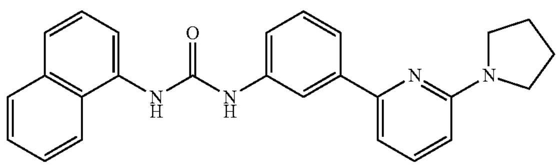 [SMILES: O=C(Nc1cccc(-c2cccc(N3CCCC3)n2)c1)Nc1cccc2ccccc12] | 1256 ± 125 | 69% | 1269 | 109% |
| 10x | 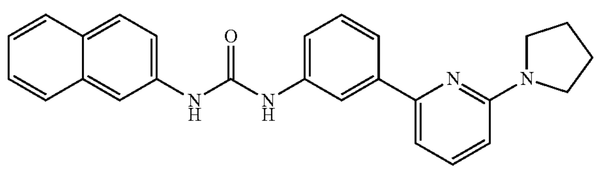 [SMILES: O=C(Nc1cccc(-c2cccc(N3CCCC3)n2)c1)Nc1ccc2ccccc2c1] | 1830 | 68% | 1914 | 119% |
| 10y | 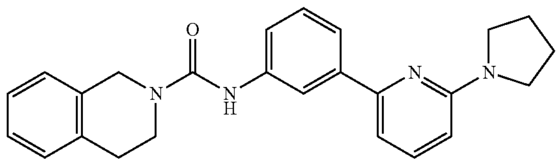 [SMILES: O=C(Nc1cccc(-c2cccc(N3CCCC3)n2)c1)N1CCc2ccccc2C1] | >10,000 | 2.55% | 5342 | 50% |
| 10r | 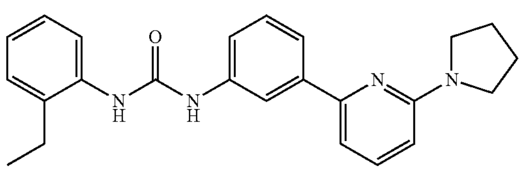 [SMILES: CCc1ccccc1NC(=O)Nc1cccc(-c2cccc(N3CCCC3)n2)c1] | 1190 ± 120 | 42% | 3316 | 76% |
| 10v | 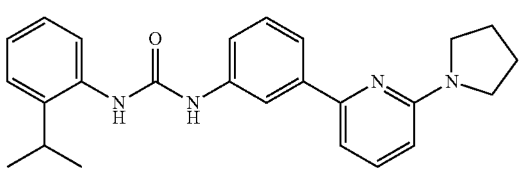 [SMILES: CC(C)c1ccccc1NC(=O)Nc1cccc(-c2cccc(N3CCCC3)n2)c1] | 4808 | 70% | 4203 | 66% |

TABLE 1-continued

Biological Activity of Exemplary Compounds

| Compound No. | Structure | cAMP EC$_{50}$ nM | cAMP % inhibition | β-arrestin EC$_{50}$ nM | β-arrestin % inhibition |
|---|---|---|---|---|---|
| 17 | | 1145 | 33% | 672 | 106% |
| 15 | | >10,000 | 0.6% | 8524 | 24% |
| 16 | | >10,000 | 35% | >10,000 | 1.5% |
| 19a | | 1268 | 53% | 1201 | 118% |
| 10s | | >10,000 | 18% | 209 | 109% |
| 19b | | >10,000 | 30% | 126 | 120% |

TABLE 1-continued

Biological Activity of Exemplary Compounds

| Compound No. | Structure | cAMP EC$_{50}$ nM | % inhibition | β-arrestin EC$_{50}$ nM | % inhibition |
|---|---|---|---|---|---|
| 21a | | >10,000 | 9% | 3402 | 73% |
| 22a | | 6491 | 49% | 4892 | 83% |
| 23a | | 820 | 41% | 1090 | 117% |
| 24a | | 1230 | 82% | 276 | 126% |

TABLE 1-continued

Biological Activity of Exemplary Compounds

| Compound No. | Structure | cAMP | | β-arrestin | |
|---|---|---|---|---|---|
| | | $EC_{50}$ nM | % inhibition | $EC_{50}$ nM | % inhibition |
| 23c | 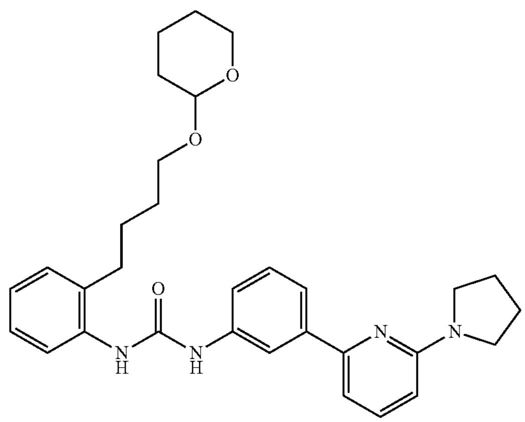 [SMILES: O=C(Nc1cccc(-c2cccc(N3CCCC3)n2)c1)Nc1ccccc1CCCCOC1CCCCO1] | >10,000 | 20% | 6191 | 69% |
| 21b | 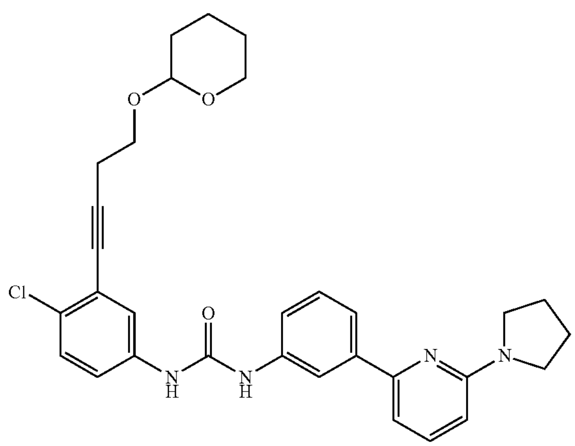 [SMILES: O=C(Nc1cccc(-c2cccc(N3CCCC3)n2)c1)Nc1ccc(Cl)c(C#CCCOC2CCCCO2)c1] | >10,000 | 22% | 208 | 111% |
| 22b | 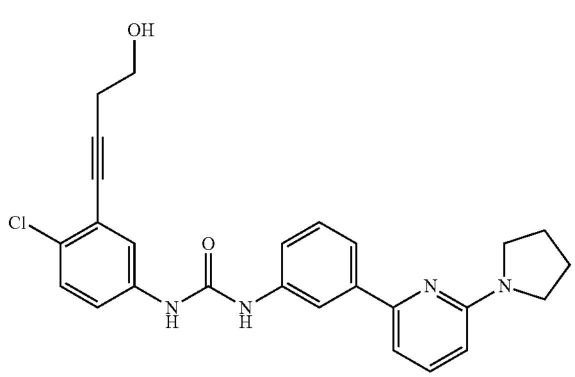 [SMILES: O=C(Nc1cccc(-c2cccc(N3CCCC3)n2)c1)Nc1ccc(Cl)c(C#CCCO)c1] | 551 | 152% | 149 | 123% |

TABLE 1-continued

Biological Activity of Exemplary Compounds

| Compound No. | Structure | cAMP EC$_{50}$ nM | cAMP % inhibition | β-arrestin EC$_{50}$ nM | β-arrestin % inhibition |
|---|---|---|---|---|---|
| 23b | | 354 | 55% | 771 | 121% |
| 24b | | 1420 | 111% | 1349 | 125% |
| 13a | | 1643 | 17% | 1022 | 99% |
| 27 | | 527 | 31% | 384 | 109% |
| 28 | | 1666 | 39% | 2334 | 62% |

TABLE 1-continued

Biological Activity of Exemplary Compounds

| Compound No. | Structure | cAMP EC$_{50}$ nM | cAMP % inhibition | β-arrestin EC$_{50}$ nM | β-arrestin % inhibition |
|---|---|---|---|---|---|
| 13b | 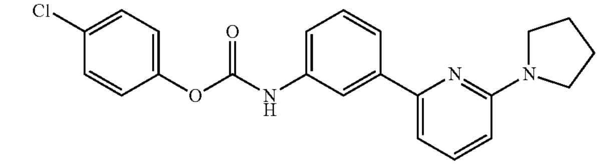 [SMILES: O=C(Nc1cccc(-c2cccc(N3CCCC3)n2)c1)Oc1ccc(Cl)cc1] | >10,000 | 3.5% | 5370 | 24% |
| 31 | 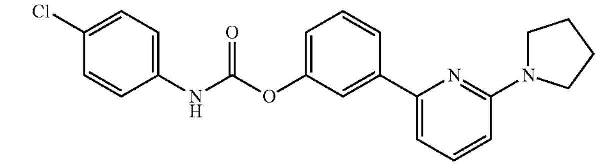 [SMILES: O=C(Nc1ccc(Cl)cc1)Oc1cccc(-c2cccc(N3CCCC3)n2)c1] | >10,000 | 8.8% | 8663 | 58% |
| 13c | 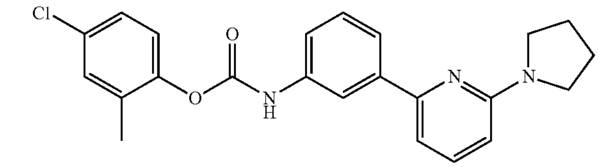 [SMILES: Cc1cc(Cl)ccc1OC(=O)Nc1cccc(-c2cccc(N3CCCC3)n2)c1] | 3046 | 24% | 3071 | 39% |
| 32 | 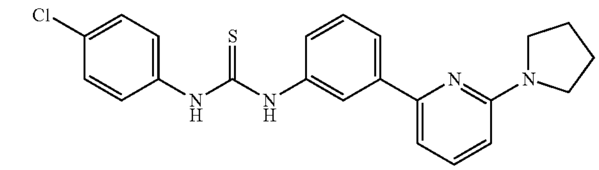 | 830 | 77% | 276 | 110% |
| 35 | 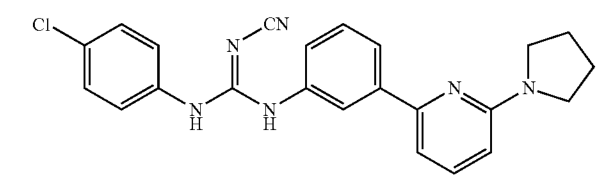 [SMILES: N#C/N=C(/Nc1ccc(Cl)cc1)Nc1cccc(-c2cccc(N3CCCC3)n2)c1] | 3343 | 29% | 3064 | 69% |
| 38 "GAT 358" | 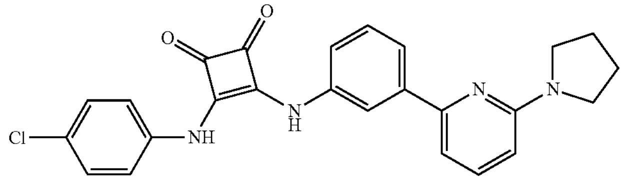 [SMILES: O=c1c(Nc2ccc(Cl)cc2)c(Nc2cccc(-c3cccc(N4CCCC4)n3)c2)c1=O] | >10,000 | 16% | 111 | 107% |
| 45 | 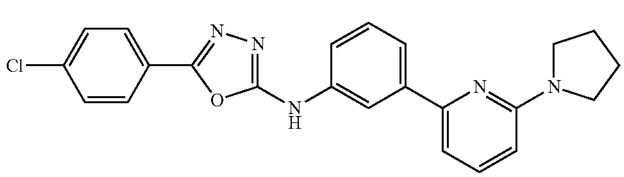 [SMILES: Clc1ccc(-c2nnc(Nc3cccc(-c4cccc(N5CCCC5)n4)c3)o2)cc1] | 4053 | 20% | 3213 | 70% |

TABLE 1-continued

Biological Activity of Exemplary Compounds

| Compound No. | Structure | cAMP EC$_{50}$ nM | % inhibition | β-arrestin EC$_{50}$ nM | % inhibition |
|---|---|---|---|---|---|
| 42 | 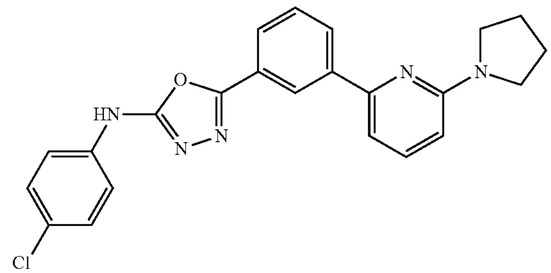 [SMILES: Clc1ccc(Nc2nnc(-c3cccc(-c4cccc(N5CCCC5)n4)c3)o2)cc1] | >10,000 | 43% | 5851 | 31% |
| 55 | 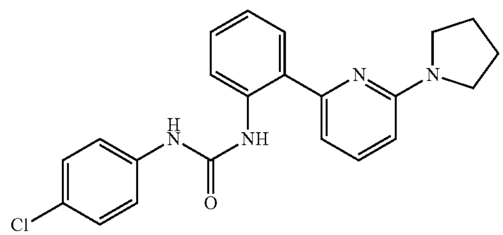 [SMILES: O=C(Nc1ccc(Cl)cc1)Nc1ccccc1-c1cccc(N2CCCC2)n1] | 3400 | 110% | 5863 | 61% |
| 51 | 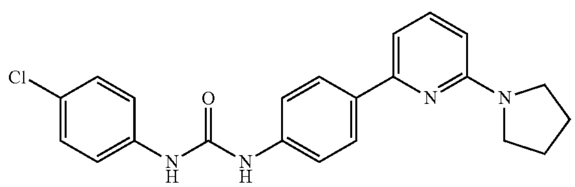 [SMILES: O=C(Nc1ccc(Cl)cc1)Nc1ccc(-c2cccc(N3CCCC3)n2)cc1] | >10,000 | 11% | 206 | 109% |
| 57 "GAT 369" | 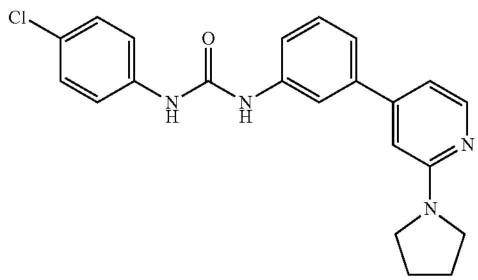 [SMILES: O=C(Nc1ccc(Cl)cc1)Nc1cccc(-c2ccnc(N3CCCC3)c2)c1] | 9789 | 50% | 77 | 111% |
| 64 | 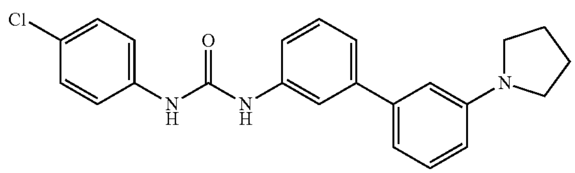 [SMILES: O=C(Nc1ccc(Cl)cc1)Nc1cccc(-c2cccc(N3CCCC3)c2)c1] | 679 | 84% | 27 | 110% |
| 61 | 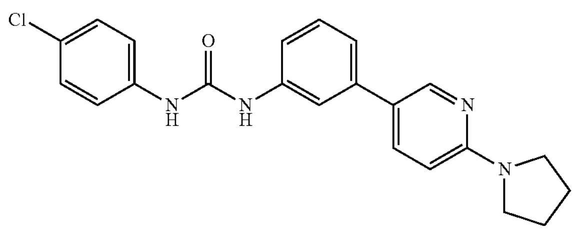 [SMILES: O=C(Nc1ccc(Cl)cc1)Nc1cccc(-c2ccc(N3CCCC3)nc2)c1] | >10,000 | 6% | 880 | 105% |

TABLE 1-continued

Biological Activity of Exemplary Compounds

| Compound No. | Structure | cAMP | | β-arrestin | |
|---|---|---|---|---|---|
| | | $EC_{50}$ nM | % inhibition | $EC_{50}$ nM | % inhibition |
| 67a | 4-chlorophenyl-urea-phenyl-pyridine-morpholine | 564 | 88% | 124 | 111% |
| 67b | 4-chlorophenyl-urea-phenyl-pyridine-piperazine | 274 | 113% | 25 | 110% |
| 68 | 4-cyanophenyl-aminosquarate-phenyl-pyridine-pyrrolidine | — | — | — | — |
| 69 | 4-chlorobenzylamino-squarate-phenyl-pyridine-pyrrolidine | — | — | — | — |
| 70 | 5-chloro-3-ethyl-indole-2-carboxamide-ethyl-pyridine-piperidine | — | — | — | — |
| 71 | 5-nitro-3-ethyl-indole-2-carboxamide-ethyl-pyridine-piperidine | — | — | — | — |

Synthesis and Evaluation of Exemplary Covalent Allosteric Modulators of the Present Technology Scheme 22: General synthetic scheme for 2-(4-(piperidin-1-yl)phenyl)ethan-1-amine

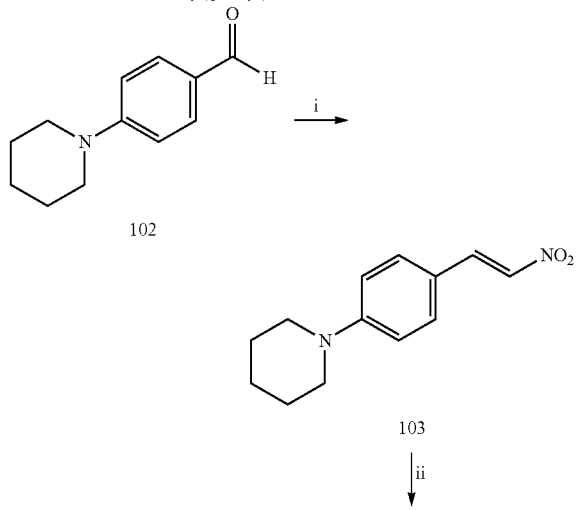

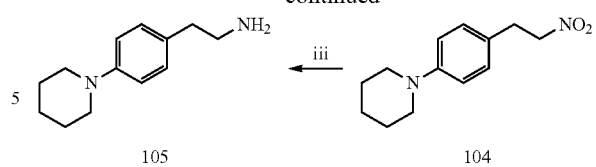

Reagent and reaction conditions: i) anhydrous nitromethane, ammonium acetate, 105° C., argon, 2 h (78%); ii) NaBH$_4$, methanol, RT, 2 h (86%); iii) NiCl$_2$•6H$_2$O, NaBH$_4$, THF: methanol (95:5), 0° C., 4 h (81%).

As illustrated in Scheme 22, compound 102 was synthesized using the base catalyzed N-alkylation of 4-bromobenzaldehyde described in de Lange, B.; Lambers-Verstappen, M. H.; van de Vondervoort, L. S.; Sereinig, N.; de Rijk, R.; de Vries, A. H. M.; de Vries, J. G. Synlett 2006, 3105 to produce compound 102 in 67% yield. The Henry reaction of 102 in presence of ammonium acetate in nitromethane gave nitrostyrene 103 in 78% yield. Nitrostyrene 3 was subsequently reduced with sodium borohydride to give compound 104 in 86% yield. Reduction of the nitro group of compound 104 was afforded by in situ generated nickel borohydride to give phenethylamine 105 in 81% yield.

Scheme 23: General synthetic protocol for indole esters

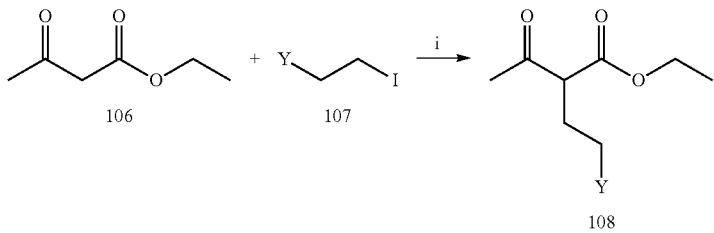

Where: X: Cl, NO$_2$; Y: CH$_3$;

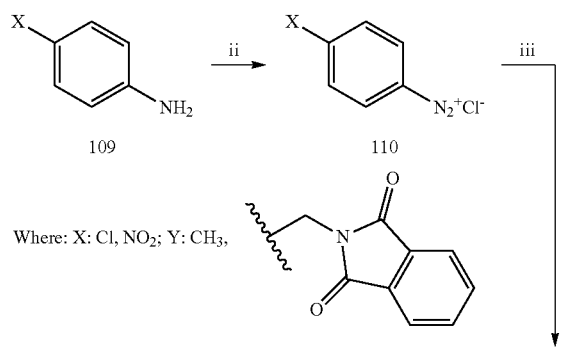

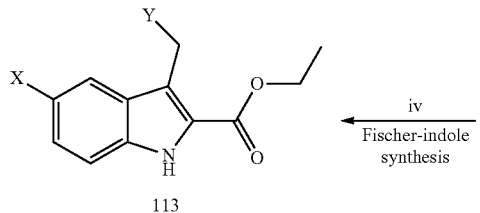
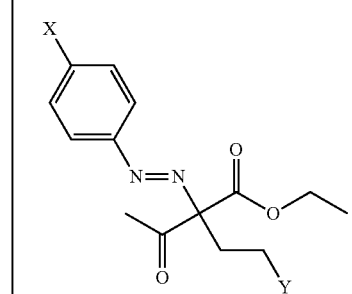
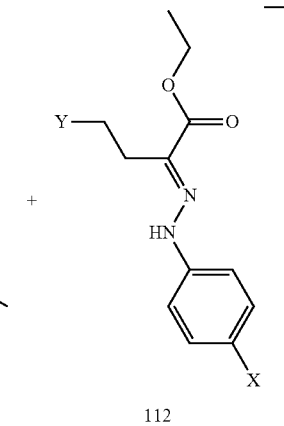

Reagent and reaction conditions: i) NaOEt, anhydrous ethanol, argon, 12 h, reflux (67%); ii) NaNO$_2$, HCl, 0° C., 1 h (99%); iii) 108 + CH$_3$COONa, pH 5-6, ethanol, 0° C.; iv) 15% H$_2$SO$_4$ in anhydrous ethanol reflux, argon, 12-24 h (74-85%).

3-alkyl-5-substituted indole esters were synthesized per Scheme 23, starting with condensation of β-keto-esters 108 with diazonium salts 110 per the Japp-Klingeman method to provide the azo and hydrazone compounds (111 and 112, respectively) which are dehydrated by alcoholic sulfuric acid using regular Fischer cylclization to give indole esters 113. Noteably, as both azo 111 and hydrazone 112 compounds undergo Fischer indole cylclization to give the indole ester 113, these were not isolated prior to the Fischer indole synthesis step.

Ethyl-2-acetyl pentanoate: To a flask containing anhydrous ethanol (200 mL) under an argon atmosphere at room temperature was added sodium metal (6 g, 260 mmol) portion wise and was stirred till it completely dissolves (30 min) To this was added ethyl acetoacetate (106) (30 g, 230 mmol) and the resulting solution was refluxed for 30 min. This was followed by addition of propyl iodide (44.44 g, 241.5 mmol), over a period of 30 min through dropping funnel and the reaction was refluxed for 20 h. The reaction mixture was cooled to room temperature and filtered. The filtrate was neutralized by adding 1N HCl and concentrated under reduced pressure and partitioned in EtOAc and water. The organic layer separated and aqueous layer extracted with EtOAc (2×200 mL). Combined organic layer was washed with brine and dried (Na$_2$SO$_4$). The product was purified by flash column chromatography (5% to 20% EtOAc:Hexane) to give ethyl-2-acetyl pentanoate as a clear liquid (30.87 g: 78% yield). Rf=0.45 (EtOAc/Hexane=20/80). $^1$H NMR (400 MHz, CDCl3): δ 4.20 (q, J=7.2 Hz, 2H), 3.42 (t, J=7.4 Hz, 1H), 2.22 (s, 3H), 1.92-1.76 (m, 2H), 1.40-1.20 (m, 5H, especially 1.28, t, J=7.2 Hz, 3H), 0.93 (t, J=7.2 Hz, 3H). Mass spectrum m/z—172.10 [M+H]+

4-Chlorobenzenediazonium Chloride: A solution of sodium nitrite (1.7 g, 23 mmol) in water (5 mL) cooled to 0° C. was added to a suspension of finely powdered 4-chloro aniline (2.54 g, 20 mmol) in 10 mL of 24% aq. hydrochloric acid at 0° C. and the resulting solution was stirred for 45 min keeping the temperature between 0°-5° C. The resulting pale yellow solution of diazonium salt was used directly in the next reaction.

(E)-Ethyl 2-[(4-chlorophenyl)diazenyl]pentanoate and (E)-ethyl 2-acetyl 2-((4-chlorophenyl)diazenyl)pentanoate: To a solution of ethyl-2-acetyl pentanoate (0.5 g, 2.9 mmol) in 30 mL ethanol under an argon atmosphere at room temperature was added sodium acetate trihydrate (0.83 g, 6.12 mmol) and the resulting mixture was stirred at same temperature for 45 min. It was then cooled to -5° C. and 4-chlorobenzenediazonium chloride was added to this together with additional sodium acetate to maintain the pH at 5 and the resulting solution was stirred for 3 h keeping the temperature between 0° C. to 5° C. The reaction was quenched by adding a saturated aqueous NaHCO$_3$ solution. The volatiles were removed under reduced pressure and the mixture was extracted with EtOAc (4×40 mL). The organic layer was washed with water, brine and dried over sodium sulfate. The solvent was removed over vacuum to give crude red oil (0.55 g, 70.6% yield) as a 4:1 mixture of azo and hydrazone. The crude was purified by flash column chromatography (5% to 30% EtOAc:Hexane) to give the azo compound (E)-ethyl 2-[(4-chlorophenyl)diazenyl]pentanoate (0.44 g) as a yellow solid which was first eluted followed by the hydrazone compound (E)-ethyl 2-acetyl-2-((4-chlorophenyl)diazenyl)pentanoate (0.11 g) which was obtained as a brown solid. Rf=0.78 (EtOAc/Hexane=20/80); $^1$H NMR (500 MHz, CDCl3): δ 7.71, (d, J=9.0 Hz, 2H), 7.47 (d, J=9.0 Hz, 2H), 4.31-4.20 (m, 2H), 2.30 (s, 3H), 2.21-2.06 (m, 2H), 1.48-1.28 (m, 2H), 1.26 (t, J=7.0 Hz, 3H), 0.91 (t, J=7.5 Hz, 3H). Mass spectrum m/z—311.11 [M+H]+. Rf=0.6 (EtOAc/Hexane=20/80) 1H NMR (500 MHz, CDCl3): δ 7.93 (s, 1H, NH), 7.29 (d, J=9.0 Hz, 2H), 7.18 (d, J=9.0 Hz, 2H), 4.36 (q, J=7.0 Hz, 2H), 2.6 (t, J=8.0 Hz, 2H), 1.68-1.58 (m, 2H), 1.42 (t, J=7.0 Hz, 3H), 1.06 (t, J=8.0 Hz, 3H). Mass spectrum m/z—269.11 [M+H]+

Ethyl 5-chloro-3-ethyl-1H-indole-2-carboxylate: A mixture of the above azo compound (0.4 g, 1.28 mmol) and hydrazine compound (0.1 g, 0.37 mmol) was taken in 60 ml of 15% H$_2$SO$_4$ in anhydrous ethanol and the reaction was refluxed under inert conditions for 16 h, cooled to room temperature and neutralized by adding saturated NaHCO$_3$ solution and extracted with EtOAc (4×50 mL). Combined organic layer was washed with water, brine and dried (MgSO$_4$). The volatiles were removed under vacuum to yield crude which was purified by flash column chromatography on silica gel (0% to 15% EtOAc:Hexane) to give pure 113 as a white crystalline solid (250 mg, 50% yield). Rf=0.35 (EtOAc/Hexane=20/80). $^1$H NMR (400 MHz, CDCl3): δ 8.74 (br s, 1H, NH), 7.65 (d, J=1.2 Hz, 1H), 7.30 (d, J=8.8 Hz, 2H), 7.25 (dd, J=8.8 Hz, J=1.2 Hz, 1H), 4.42 (q, J=7.2 Hz, 2H), 3.07 (q, J=7.2 Hz, 2H), 1.43 (t, J=7.2 Hz, 3H), 1.26 (t, J=7.2 Hz, 3H). Mass spectrum m/z—251.07 [M+H]+

4-Nitrobenzenediazonium Chloride: A solution of sodium nitrite (0.7 g, 9.5 mmol) in water (5 mL) cooled to 0° C. was added to a suspension of finely powdered 4-nitro aniline (1 g, 7.25 mmol) in 10 mL of 24% aq. hydrochloric acid at 0° C. and the resulting solution was stirred for 45 min keeping the temperature between 0°-5° C. The resulting pale yellow solution of diazonium salt was directly used for the next reaction.

(E)-ethyl 2-[2-(4-nitrophenyl)hydrazono]pentanoate and (E)-ethyl 2-acetyl-2-[(4-nitrophenyl)diazenyl] pentanoate: To a solution of ethyl-2-acetyl pentanoate (1.3 g, 5.4 mmol) in 30 mL ethanol under an argon atmosphere at room temperature was added sodium acetate trihydrate (6.5 g) and the resulting mixture was stirred at same temperature for 45 min. It was then cooled to −5° C. and 4-nitrobenzenediazonium chloride was added to this together with additional sodium acetate to maintain the pH at 5 and the resulting solution was stirred for 3 h keeping the temperature between 0° C. to 5° C. The volatiles were removed under reduced pressure and the mixture was extracted with EtOAc (4×40 mL). The organic layer was washed with water, brine and dried over sodium sulfate. The solvent was removed over vacuum to give crude product as red oil (1.39 g, 80.6% yield) as a 4:1 mixture of (E)-ethyl 2-acetyl-2-[(4-nitrophenyl)diazenyl] pentanoate and (E)-ethyl 2-[2-(4-nitrophenyl)hydrazono]pentanoate. The crude was purified by flash column chromatography (5% to 30% EtOAc:Hexane) to give azo compound (E)-ethyl 2-acetyl-2-[(4-nitrophenyl)diazenyl] pentanoate (1.12 g) as a yellow solid which was first eluted followed by (E)-ethyl 2-[2-(4-nitrophenyl)hydrazono]pentanoate (0.27 mg) which was obtained as a brown solid. (E)-ethyl 2-acetyl-2-[(4-nitrophenyl)diazenyl] pentanoate: Rf=0.46 (EtOAc/Hexane=20/80). $^1$H NMR (500 MHz, CDCl3): δ 8.37 (d, J=9.0 Hz, 2H), 7.87 (d, J=9.0 Hz, 2H), 4.35-4.24 (m, 2H), 2.33 (s, 3H), 2.26-2.12 (m, 2H), 1.52-1.35 (m, 2H), 1.28 (t, J=7.0 Hz, 3H), 0.93 (t, J=7.5 Hz, 3H). Mass spectrum m/z—308.12 [M+H]+. (E)-ethyl 2-[2-(4-nitrophenyl)hydrazono]pentanoate: Rf=0.23 (EtOAC/Hexane=20/80). $^1$H NMR (500 MHz, CDCl3): δ 8.22 (d, J=9.0 Hz, 2H), 8.08 (s, 1H, NH), 7.25 (d, J=9.0 Hz, 2H), 4.34 (q, J=7.0 Hz, 2H), 2.60 (t, J=8.0 Hz, 2H), 1.67-1.58 (m, 2H), 1.40 (t, J=7.0 Hz, 3H), 1.05 (t, J=7.5 Hz, 3H). Mass spectrum m/z—280.12 [M+H]+

Ethyl 3-ethyl-5-nitro-1H-indole-2-carboxylate: A mixture of (E)-ethyl 2-acetyl-2-[(4-nitrophenyl)diazenyl] pentanoate (0.8 g, 2.48 mmol) and (E)-ethyl 2-[2-(4-nitrophenyl)hydrazono]pentanoate (0.2 g, 0.716 mmol) was taken in 20% ethanolic (anhydrous) $H_2SO_4$ (30 mL) and the resulting solution was refluxed overnight under an argon atmosphere. The reaction mixture was cooled to room temperature and neutralized by adding saturated $NaHCO_3$ solution and extracted with EtOAc (4×50 mL). Combined organic layer was washed with water, brine and dried (Na2SO4). The volatiles were removed under vacuum to yield crude which was purified by flash column chromatography on silica gel (0% to 15% EtOAc:Hexane) to give pure ethyl 3-ethyl-5-nitro-1H-indole-2-carboxylate as a white crystalline solid (370.5 mg, 57% yield). Rf=0.29 (EtOAc/Hexane=20/80). $^1$H NMR (400 MHz, CDCl3): δ 9.02 (s, 1H, NH), 8.69 (d, J=2.0 Hz, 1H), 8.22 (dd, J=8.8 Hz, J=2.4 Hz, 1H), 7.43 (d, J=9.6 Hz, 1H), 4.46 (q, J=7.6 Hz, 2H), 3.16 (q, J=7.2 Hz, 2H), 1.45 (t, J=7.6 Hz, 3H), 1.31 (t, J=7.2 Hz, 3H). Mass spectrum m/z—263.11 [M+H]+

Scheme 24:

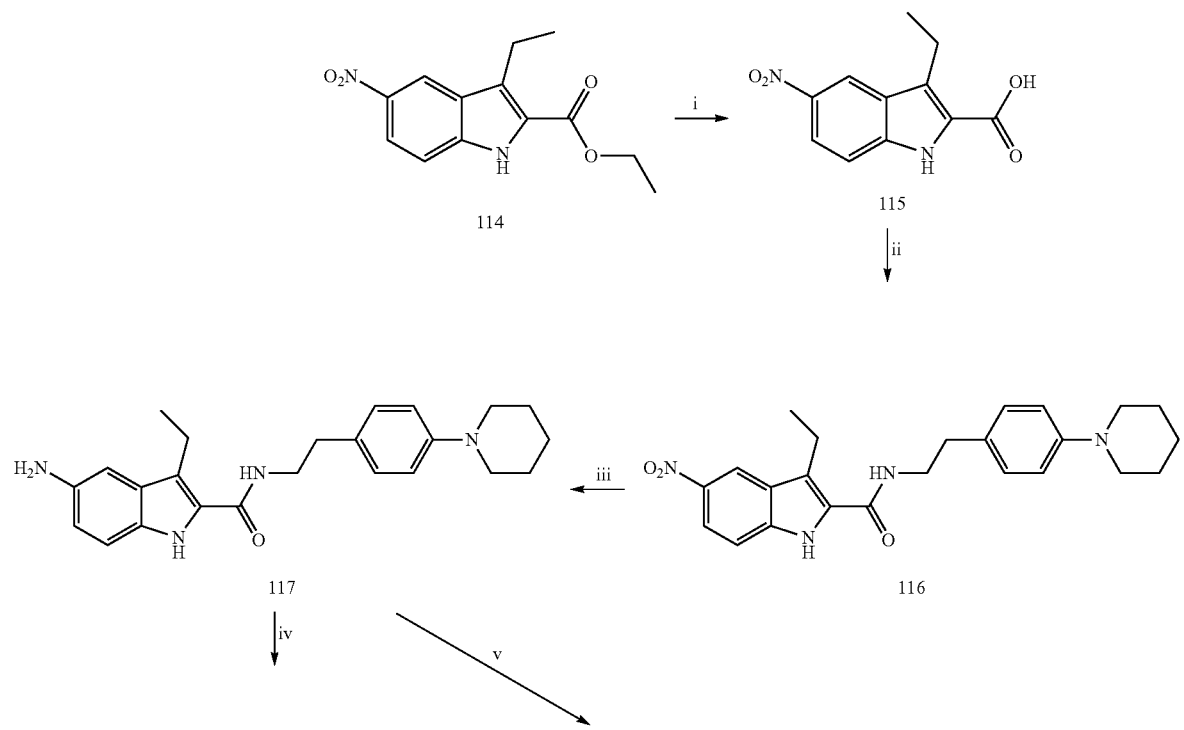

-continued

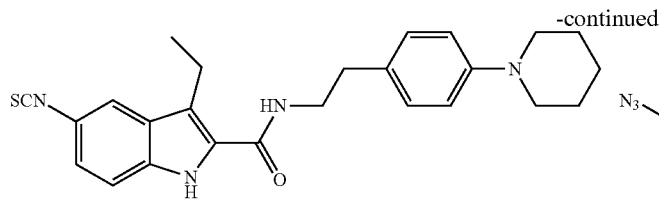

118 (GAT100)

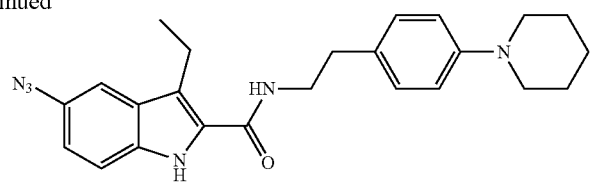

119 (GAT206)

Reagents and conditions: i) dioxane:water (10:1), KOH, reflux, 2-4 h (99%); ii) 105 + EDCI, HOBT, Hunig's base, anhydrous NMP, RT, argon, 12-16 h (64%); iii) NiCl$_2$•6H$_2$O, NaBH$_4$, THF:methanol (95:5), -10° C., 2 h (80%); iv) TPP, CS$_2$, argon, RT, 20 min (53%); v) t-BuONO, TMSN$_3$, anhydrous THF, argon, 0° C., 3 h (65%).

Nitro indole 114 was synthesized using the Japp-Klingmann protocol by treatment of diazonium salt of 4-nitroaniline with sodium acetate treated ethyl 2-acetylpentanoate gave a mixture of azo and hydrazone in 80% yields. These were heated in the presence of ethanolic sulfuric acid to produce an indole 114 (57%) via the Fischer indole synthesis (similar to Scheme 23).

Base catalyzed hydrolysis of ester 114 gave indole acid 115 in 99% yield. Coupling of acid 114 with amine 105 gave 5-nitro analog 116 in 64% yield. Reduction of 116 using in situ generated nickel borohydride generated amine 117 in high yield (80%). With this procedure, compound 117 was prepared in gram quantities. Exposure of aromatic amine 117 to a mixture of tert-butyl nitrite and azidotrimethylsilane yielded aromatic azide 119 in 65% yield. The aryl isothiocyanate analog 118 was provided in 53% yield by treatment of 117 with triphenylphosphine followed by exposure to CS$_2$.

Ethyl 3-ethyl-5-nitro-1H-indole-2-carboxylic acid (115): To a solution of 114 (170 mg, 0.648 mmol) in dioxane (10 mL) was added a solution of KOH (200 mg, 3.54 mmol) in water (3 mL) and the resulting solution was refluxed for 2 h. It was then cooled to room temperature, concentrated under reduced pressure and neutralized by addition of 1N HCl. The precipitated acid was filtered, washed with cold water and air dried to give pure acid 121 (104 mg, 72% yield) as white solid. 1H NMR (400 MHz, DMSO): δ 12.14 (s, 1H), 8.67 (d, J=2.0 Hz, 1H), 8.11 (dd, J=8.8 Hz, J=2.5 Hz, 1H), 7.54 (d, J=8.8 Hz, 1H), 3.12 (q, J=8.0 Hz, 2H), 1.22 (t, J=7.6 Hz, 3H). Mass spectrum m/z—235.06 [M+H]+

3-Ethyl-5-nitro-N-[4-(piperidin-1-yl) phenethyl]-1H-indole-2-carboxamide (116): To a solution of acid 115 (40 mg, 0.172 mmol), amine 105 (60 mg, 0.29 mmol), HOBT (50 mg, 0.37 mmol), DIPEA (100 mg, 0.775 mmol) in anhydrous NMP (5 mL) was added EDCI (100 mg, 0.645 mmol) under an argon atmosphere and at room temperature and the resulting mixture was stirred overnight. Reaction mixture was diluted with ethyl acetate (25 mL) and water (10 mL). The organic layer was separated and aqueous layer extracted with EtOAc (3×20 mL). Combined organic layer was washed with water, brine and dried (Na$_2$SO$_4$). Evaporation of volatiles under reduced pressure gave crude which was purified by flash column chromatography on silica gel (10%:40% EtOAc:Hexane) to give 116 as a white crystalline solid (66.4 mg, 92% yield.) M.p.=208-211° C. Rf=0.8 (MeOH/DCM=20/80. $^1$H NMR (500 MHz, CDCl3): δ 9.97 (s, 1H, indole NH), 8.59 (d, J=2.0 Hz, 1H), 8.16 (dd, J=9.5 Hz, J=2.0 Hz, 1H), 7.44 (d, J=9.5 Hz, 1H), 7.15 (d, J=8.5 Hz, 2H), 6.93 (d, J=8.5 Hz, 2H), 6.12 (br t, J=6.0 Hz, 1H, NH of amide), 3.82 (q, J=6.0 Hz, 2H), 3.14 (t, J=5.5 Hz, 4H), 2.91 (t, J=7.0 Hz, 2H), 2.79 (q, J=7.5 Hz, 2H), 1.76-1.68 (m, 4H), 1.62-1.54 (m, 2H), 1.13 (t, J=7.5 Hz, 3H). Mass spectrum m/z—421.22 [M+H]+

5-Amino-3-ethyl-N-[4-(piperidin-1-yl) phenethyl]-1H-indole-2-carboxamide (117): To a solution of 116 (75 mg, 0.178 mmol) in anhydrous THF (25 mL) and methanol (2 mL) under an argon atmosphere at room temperature was added NiCl$_2$.6H2O (200 mg, 0.841 mmol) and reaction mixture was stirred for 45 min at room temperature. It was then cooled to −5° C. and NaBH$_4$ (100 mg, 2.64 mmol) was added in small portions to result in a black solution, the reaction was then gradually warmed to room temperature and stirred for 1 h. Reaction was quenched by addition of saturated aqueous solution of ammonium chloride and concentrated under reduced pressure. The residue was diluted with EtOAc and water and filtered. The organic layer was separated and aqueous layer was extracted with EtOAc (6×40 mL). Combined organic layer was washed with brine and dried (MgSO$_4$) and evaporated under vacuum to yield crude (60 mg, 86% yield) which was taken for the next reaction without further purification. M.p.=208-209° C.; Rf=0.8 (MeOH/DCM=20/80). $^1$H NMR (500 MHz, DMSO-d6): δ 10.60 (s, 1H, NH of indole), 7.74 (t, J=5.5 Hz, 1H), 7.08 (d, J=9.0 Hz, 3H, two overlapping doublets), 6.85 (d, J=9.0 Hz, 2H), 6.69 (d, J=2.0 Hz, 1H), 6.62 (dd, J=9.0 Hz, J=2.0 Hz, 1H), 4.56 (br s, 2H, NH2), 3.44 (q, J=6.5 Hz, 2H), 3.06 (t, J=5.5 Hz, 4H), 2.90 (q, J=7.5 Hz, 2H), 2.74 (t, J=7.5 Hz, 2H), 1.64-1.56 (m, 4H), 1.54-1.46 (m, 2H), 1.11 (t, J=7.5 Hz, 3H). Mass spectrum m/z—390.24 [M+H]+

3-Ethyl-5-isothiocyanato-N-[4-(piperidin-1-yl) phenethyl]-1H-indole-2-carboxamide (118): To a solution of 117 (27 mg, 0.065 mmol) in benzene (5 mL) was added triphenyl phosphine (17.04 mg, 0.065 mmol) under an argon atmosphere and the reaction mixture was refluxed for 4 h with constant stirring. CS$_2$ (1 mL) was added to this and the reaction mixture was refluxed for 12 h. CS$_2$ and benzene were evaporated under reduced pressure to obtain crude 118 which was purified using flash column chromatography to obtain pure 118 as a white solid (15 mg, 53.5%). Rf=0.78 (MeOH/DCM=20/80). $^1$H NMR (400 MHz, CDCl3): δ 9.79 (s, 1H), 7.46 (s, 1H), 7.35 (d, J=8.8 Hz, 1H), 7.17-7.09 (m, 3H, especially 7.14, d, J=8.0 Hz, 2H), 6.92 (d, J=8.0 Hz, 2H), 6.03 (br t, J=6.4 Hz, 1H, NH of amide), 3.80 (q, J=6.0 Hz, 2H), 3.13 (br t, J=5.6 Hz, 4H), 2.90 (t, J=6.4 Hz, 2H), 2.70 (q, J=7.6 Hz, 2H), 1.76-1.67 (m, 4H), 1.62-1.54 (m, 2H), 1.08 (t, J=7.6 Hz, 3H). Mass spectrum m/z—433.21 [M+H]+

5-Azido-3-ethyl-N-[4-(piperidin-1-yl) phenethyl]-1H-indole-2-carboxamide (119): To a solution of 118 (100 mg, 0.256 mmol) in THF (20 mL) was added t-butyl nitrite (1.6 g, 15.5 mmol) and tetramethylsilyl azide (1.2 g, 10.42 mmol), and the reaction was stirred overnight at 0° C. under argon atmosphere. The solvent was evaporated under reduced pressure at room temperature to give crude which was purified using flash column chromatography on silica gel to yield pure 119 as a white solid (44 mg, 41.26% yield).

Mp=170-173° C. Rf=0.81 (MeOH/DCM=20/80) $^1$H NMR (500 MHz, CDCl3): δ 9.14 (s, 1H, NH of indole), 7.35 (d, J=9.0 Hz, 1H), 7.20 (d, J=2.0 Hz, 1H), 7.14 (d, J=9.0 Hz, 2H), 6.95 (dd, J=9.0 Hz, J=2.0 Hz, 1H), 6.92 (d, J=9.0 Hz, 2H), 5.98 (br t, J=6.0 Hz, 1H, NH of amide), 3.78 (q, J=6.5 Hz, 2H), 3.13 (t, J=5.5 Hz, 4H), 2.89 (t, J=6.5 Hz, 2H), 2.70 (q, J=8.0 Hz, 2H), 1.75-1.68 (m, 4H), 1.64-1.54 (m, 2H), 1.08 (t, J=8.0 Hz, 3H). Mass spectrum m/z—417.23 [M+H]+

Scheme 25

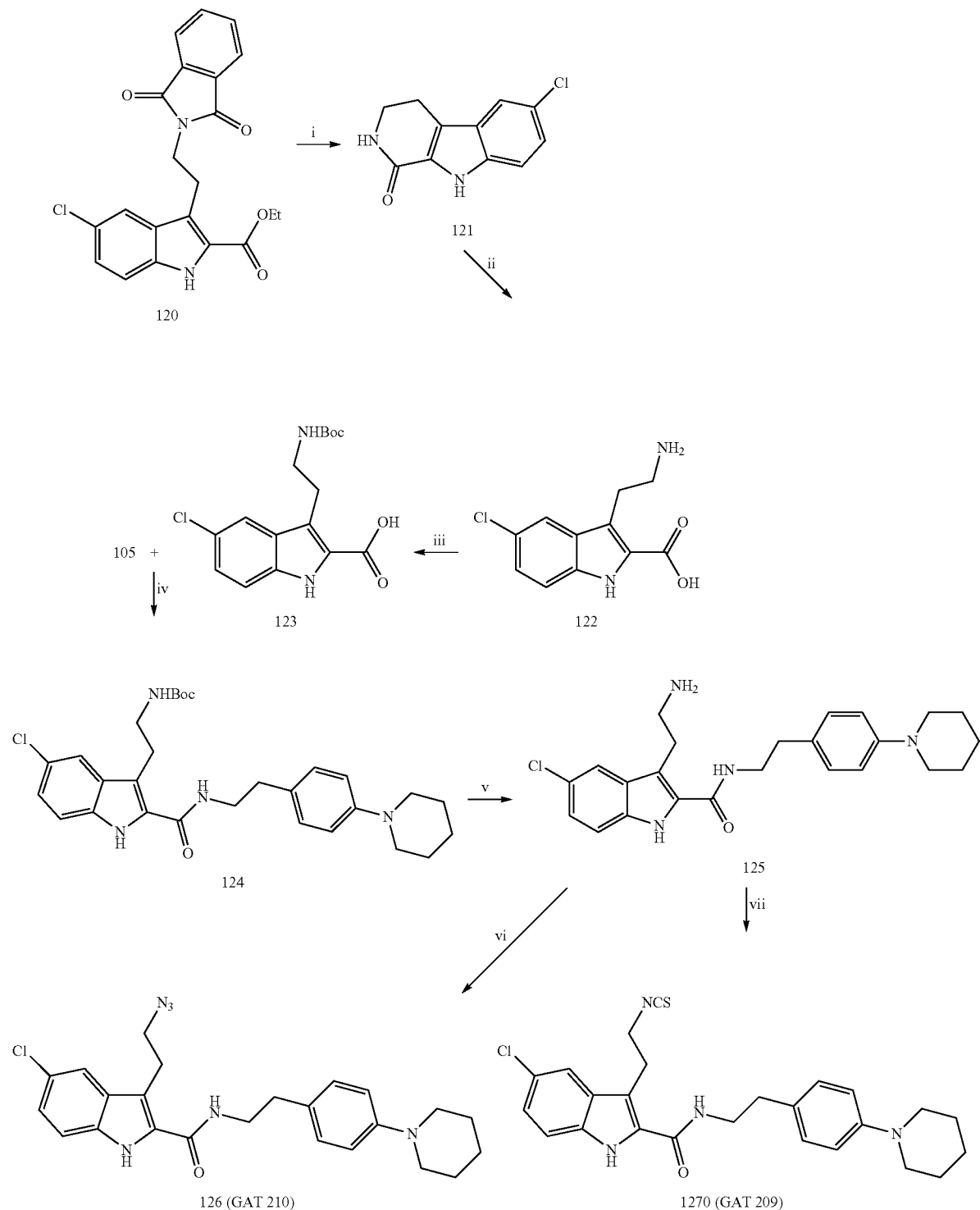

Reagents and conditions: i) 50% Ethanolamine in anhydrous ethanol, reflux, 14 h (99%); ii) KOH, dioxane:water (8:2), reflux, argon, 20 h (98%); iii) BOC anhydride, THF, NaHCO$_3$, argon, RT, 16 h (88%); iv) 105 + EDCI, HOBT, Hunig's base, anhydrous NMP, RT, argon, 18 h (68%); v) 50% TFA in DCM, RT, 3 h (91%); vi) TfN$_3$ in DCM, K$_2$CO$_3$, CuSO$_4$, methanol:water (20:1) (64%); vii) di (2-pyridyl) thionocarbonate, DCM, argon, RT, 20 min (87%).

Compounds 125 (also referenced as GAT 210) and 126 (also referenced as GAT 209) were synthesized as illustrated in Scheme 25. Indole ester 120 (synthesized per reported procedures as illustrated in Scheme 23) was treated with ethanolamine to give lactam 121 (99%) which was hydrolysed using KOH under reflux conditions to give amino-acid 122(98%). Amino group in 122 was protected using Boc anhydride to give carboxylic acid 123(88%). EDCI mediated amidation of 123 with amine 105 gave Boc protected amide 124(68%). TFA catalyzed deprotection of aliphatic amino group gave excellent yields of compound 125 (91%). Freshly prepared trifluoromethanesulfonyl azide was prepared in situ by reacting trifluoromethanesulfonic anhydride with sodium azide in dichloromethane, whereupon it was treated with 125 in prescence of $Cu^{+2}$ under basic conditions gave aliphatic azide 126 (64%). Direct conversion of amine 125 into the corresponding isothiocyanate 127 occurred at room temperature using di-2-pyridyl thionocarbonate (DPT).

6-chloro-2,3,4,9-tetrahydro-1H-pyrido[3,4-b]indol-1-one (121): To a solution of ethyl 5-chloro-3-(2-(1,3-dioxoisoindolin-2-yl)ethyl)-1H-indole-2-carboxylate (0.6 g, 1.662 mmol) in ethanol (7 ml) was added ethanolamine (1 g, 16.37 mmol) and the resultant mixture was refluxed for 14 h. It was cooled to RT, volatiles were removed under vacuum and the mixture was partitioned in EtOAc and water. The organic layer was washed with brine and dried over sodium sulfate. The solvent was removed under vacuum to give a pure white solid (360 mg, 99% yield). Rf=0.2 (EtOAc/Hexane=50/50).

3-(2-aminoethyl)-5-chloro-1H-indole-2-carboxylic acid (122): To a solution of 3-(2-aminoethyl)-5-chloro-1H-indole-2-carboxylic acid (0.34 g, 1.54 mmol) in ethanol:water (1:1) was added potassium hydroxide (6 eq.) in excess and the mixture was refluxed overnight. It was then cooled to RT and volatiles were removed under vacuum. The residue was diluted with ice cold water and acidified to pH 5 with conc. HCl to give precipitate which was filtered and air dried to give white solid product. (354 mg, 98% yield). Rf=0.15 (MeOH/DCM=20/80). $^1$H NMR (DMSO) d 11.2 (brS, 1H), 7.62 (d, 1H, J=1.5 Hz), 7.35 (d, 1H, J=8.5 Hz), 7.07 (dd, 1H, J=8.5 Hz, J=2 Hz), 3.62 (brS, 2H), 3.20 (t, 2H, J=6.5 Hz), 2.99 (t, 2H, J=6.5 Hz).

3-(2-((tert-butoxycarbonyl)amino)ethyl)-5-chloro-1H-indole-2-carboxylic acid (123): A mixture of 3-(2-((tert-butoxycarbonyl)amino)ethyl)-5-chloro-1H-indole-2-carboxylic acid (0.35 g, 1.46 mmol) and Boc anhydride (0.35 g, 1.603 mmol) was taken in THF and cooled to 0° C. To this 10 ml of saturated $NaHCO_3$ solution and 5 ml of water was added and the resultant was stirred at 0° C. for 3 h and then allowed to warm up to RT and stirred for 24 h. Volatiles were then removed under vacuum, ice cold water was added to the residue and it was acidified to pH 5 with conc. HCl. The resultant precipitate was filtered, the filtrate was washed with cold water and air dried to give cream colored solid which was recrystallized in methanol to give pure desired product (300 mg, 88%). Rf=0.25 (MeOH/DCM=10/90). $^1$H NMR (DMSO) δ 11.59 (s, 1H), 7.68 (s, 1H), 7.39 (d, 1H, J=8.5 Hz), 7.20 (dd, 1H, J=8.5 Hz, J=1.5 Hz), 6.87 (t as brS, 1H), 3.16 (t, 2H, J=8.5 Hz), 3.15 (t, 2H, J=8.5 Hz), 1.31 (s, 9H).

tert-butyl-(2-(5-chloro-2-((4-(piperidin-1-yl)phenethyl) carbamoyl)-1H-indol-3-yl)ethyl)carbamate (124): To a solution of acid 123 (260 mg, 0.7674 mmol), amine 5 (280 mg, 1.37 mmol), HOBT (280 mg, 2.07 mmol), DIPEA (400 mg, 3.094 mmol) in anhydrous NMP (7 mL) was added EDCI (400 mg, 2.57 mmol) under an argon atmosphere and at room temperature and the resulting mixture was stirred overnight. Reaction mixture was diluted with ethyl acetate (50 mL) and water (20 mL). The organic layer was separated and aqueous layer extracted with EtOAc (3×25 mL). Combined organic layer was washed with water, brine and dried ($Na_2SO_4$). Evaporation of volatiles under reduced pressure gave the crude product which was subsequently purified by flash column chromatography on silica gel (10%-40%:: EtOAc:Hexane) to give the desired product 124 as a white solid (352 mg, 68% yield). Rf=0.8 (EtOAc/Hexane=50/50). $^1$H NMR (CDCL3) d 9.39 (s, 1H), 7.64 (s, 1H), 7.54 (d, 1H, J=2 Hz), 7.32 (d, 1H, J=8.5 Hz), 7.21 (dd, 1H, J=8.5 Hz, J=2 Hz), 7.15 (d, 2H, J=8 Hz), 6.88 (d, 2H, J=8.5 Hz), 4.92 (brS, 1H), 3.75 (dd, 2H, J=15.5 Hz, J=6.5 Hz), 3.21 (dd, 2H, J=16 Hz, J=6 Hz), 3.11 (t, 4H, J=6 Hz) 3.09-3.03 (m, 2H), 2.95 (t, 2H, J=8 Hz), 1.70 (q, 4H, J=11.5 Hz, J=5.5 Hz, J=5.5 Hz), 1.58-1.54 (m, 2H), 1.49 (s, 9H)

3-(2-aminoethyl)-5-chloro-N-(4-(piperidin-1-yl)phenethyl)-1H-indole-2-carboxamide (125): To a solution of 50% trifluoroacetic acid in DCM (10 ml) was added compound 124 (300 mg, 0.57 mmol) and the reaction was stirred at RT for 3 h. Volatiles were then removed under vacuum, the crude was washed with saturated $NaHCO_3$ solution, and extracted in DCM. The combined organic layer was washed with brine and dried over sodium sulfate and evaporated under vacuum to give white solid as the desired product (200 mg, 91% yield). Rf=0.2 (MeOH/DCM=20/80). $^1$H NMR d 10.32 (t as brS, 1H), 9.85 (s, 1H), 7.47 (d, 1H, J=2 Hz), 7.34 (d, 1H, J=8.5 Hz), 7.18 (dd, 1H, J=9 Hz, J=2 Hz), 7.13 (d, 2H, J=9 Hz), 6.89 (d, 2H, J=8.5), 3.72 (qt, 2H, J=6.5), 3.12 (t, 4H, J=5.5), 2.94-2.84 (m, 6H), 1.71 (q, 4H, J=6H), 1.57 (q, 2H, J=6 Hz), 1.35 (s, 2H).

3-(2-azidoethyl)-5-chloro-N-(4-(piperidin-1-yl)phenethyl)-1H-indole-2-carboxamide (126): Trifluoromethanesulfonyl azide was prepared in situ according to a published procedure: to a magnetically stirred solution of 2 g of $NaN_3$ in 5 ml of $H_2O$ over 5 ml of $CH_2Cl_2$ at 0° C. was added 1.8 g of trifluoromethanesulfonyl anhydride, whereupon the low temperature and stirring were maintained for 2 h. Trifluoromethanesulfonyl azide (triflyl azide) was identified in the organic layer and in the first two extractions of the water layer with 10-ml portions of the solvent. In a separate round bottom flask, amino amide 125 (50 mg, 0.117 mmol) was taken in 2 ml of water and treated with 50 mg each of potassium carbonate and copper (II) sulfate. To this was added 15 ml of methanol and the above $TfN_3$ solution was added, more methanol was added to homogenize the mixture and it was then stirred at RT for 18 h. Volatiles were then removed under vacuum and the residue was dissolved in DCM, washed with water and then brine, and subsequently dried over sodium sulfate. The organic layer was concentrated under vacuum and purified on silica gel (0%:20%: EtOAc:Hexane) to obtain pure compound 126 (34 mg, 64%) Rf=0.7 (EtOAc/Hexane=50/50).

5-chloro-3-(2-isothiocyanatoethyl)-N-(4-(piperidin-1-yl) phenethyl)-1H-indole-2-carboxamide (127): A mixture of the 3-(2-aminoethyl)-5-chloro-N-(4-(piperidin-1-yl)phenethyl)-1H-indole-2-carboxamide (30 mg, 0.071 mmol) and di(2-pyridyl) thionocarbonate (18 mg, 0.077 mmol) was taken in DCM (5 ml) and it was stirred at RT for 15 mins, quenched by addition of cold water, partitioned in DCM: water and the organic layers were combined, washed with brine and dried on sodium sulfate. The solvents were evaporated on vacuum and the residue was purified on silica gel (5%:25%::EtOAc:Hexane) to give pure compound 127 (24 mg, 87% yield) Rf=0.35 (EtOAc/Hexane=20/80).

In Vitro Evaluation: The in vitro evaluation of the covalent allosteric modulators was performed using as described previously.

TABLE 2

Biological data for representative covalent allosteric modulators

| Compound | Structure | cAMP activity | | β-arrestin activity | |
|---|---|---|---|---|---|
| | | $EC_{50}$ (nm) | $EC_{Max}$ (%) | $EC_{50}$ (nm) | $E_{Max}$ (%) |
| GAT100 | 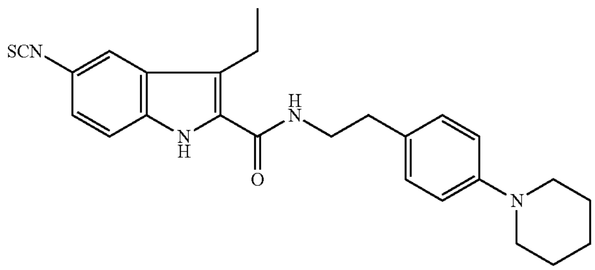 | 186.23 | 89.4 | 9.06 | 106.4 |
| GAT206 | 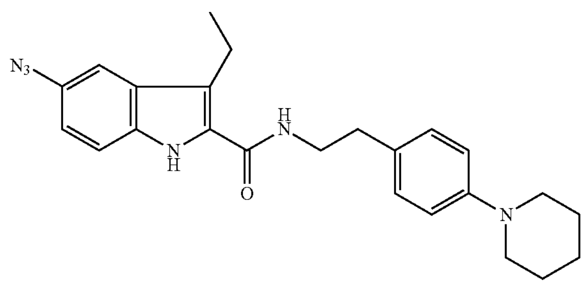 [SMILES: CCc1c(C(=O)NCCc2ccc(N3CCCCC3)cc2)[nH]c2ccc(N=[N+]=[N-])cc12] | 390.7 | 89 | 28 | 106 |
| GAT209 | 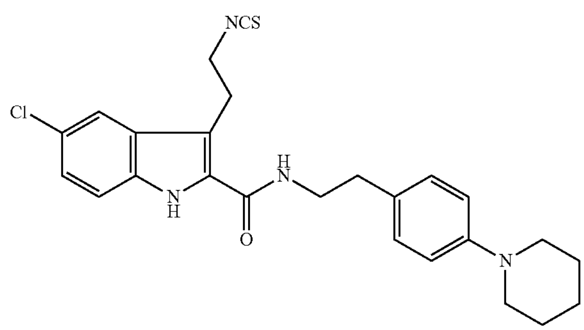 | >10,000 | 0 | 225.1 | 104.5 |
| GAT210 | 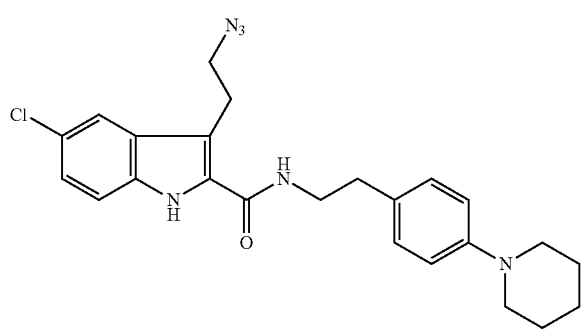 [SMILES: [N-]=[N+]=NCCc1c(C(=O)NCCc2ccc(N3CCCCC3)cc2)[nH]c2ccc(Cl)cc12] | 1097 | 93.81 | 63.93 | 105.83 |
| GAT300 | 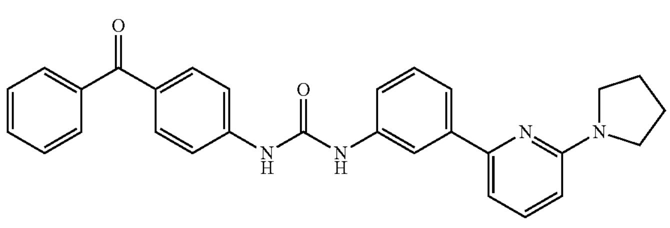 [SMILES: O=C(Nc1ccc(C(=O)c2ccccc2)cc1)Nc1cccc(-c2cccc(N3CCCC3)n2)c1] | 168.51 | 99.6 | 28.36 | 106 |

TABLE 2-continued

Biological data for representative covalent allosteric modulators

| Compound | Structure | cAMP activity | | β-arrestin activity | |
|---|---|---|---|---|---|
| | | $EC_{50}$ (nm) | $EC_{Max}$ (%) | $EC_{50}$ (nm) | $E_{Max}$ (%) |
| GAT331 | *structure* | 297.4 | 128 | 105.9 | 137.84 |
| GAT332 | *structure* | 119.02 | 78.87 | 23.97 | 106.23 |
| GAT205 | *structure* | 253.44 | 101.6 | 11.5 | 105.46 |

Effect of GAT 358 on alcohol preference in mice: FIG. 1 shows the effects of GAT 358 at various dosages on the alcohol preference in mice.

Biological Data Showing Minimal CB1 Inverse Agonist-Related Side Effects of GAT 358, a Functionally Selective CB1 Negative Allosteric Modulator:

GAT358 was assessed in two different behavioral tests, the Taste Reactivity (TR) Test and the Light Dark Emergence (LDE) Test. The TR Test is used to assess the possibility of a drug inducing nausea in rats as measured by conditioned gaping to infusion of a 0.01% saccharin solution previously paired with drug administration. The LDE Test is used as a test of anxiety where less time spent in the open field of the chamber compared to controls is interpreted as an animal demonstrating enhanced anxiety.

GAT358 was dissolved in a mixture of 4% DMSO, 1% Tween80, 1% Cremophor and 94% Saline (for doses of 5, 10 and 20 mg/kg) and injected at a volume of 3 ml/kg. Assessed was the vehicle ("Veh"), 10 and 20 mg/kg doses of GAT358 in the conditioned gaping model of nausea where rats are infused for 2 min with novel 0.01% saccharin followed immediately by an injection of the appropriate drug dose [Vehicle (n=6), GAT358-10 (n=8) and GAT358-20 (n=8)]. Seventy two hours following conditioning the rats were infused for 2 min with 0.01% saccharin during the drug free TR Test while their orofacial responses were videotaped for subsequent scoring. Further assessed was the Veh, 5 and 10 mg/kg of GAT358 in the LDE test [Veh (n=6), GAT358-5 (n=8) and GAT358-10 (n=8)]. Group assignment was counterbalanced based upon previous drug experience. The rats were administered the appropriate drug dose 45 min prior to being placed in the enclosed dark chamber that allowed access to an open field area where the lighting was 100 lux. The activity of the rat while in the LDE test for 5 min was tracked by Ethovision (Noldus Information Technology) and subsequently the duration of time spent in the open field and activity (distance travelled (cm)/amount of time(sec)) was analyzed.

Figure 2:
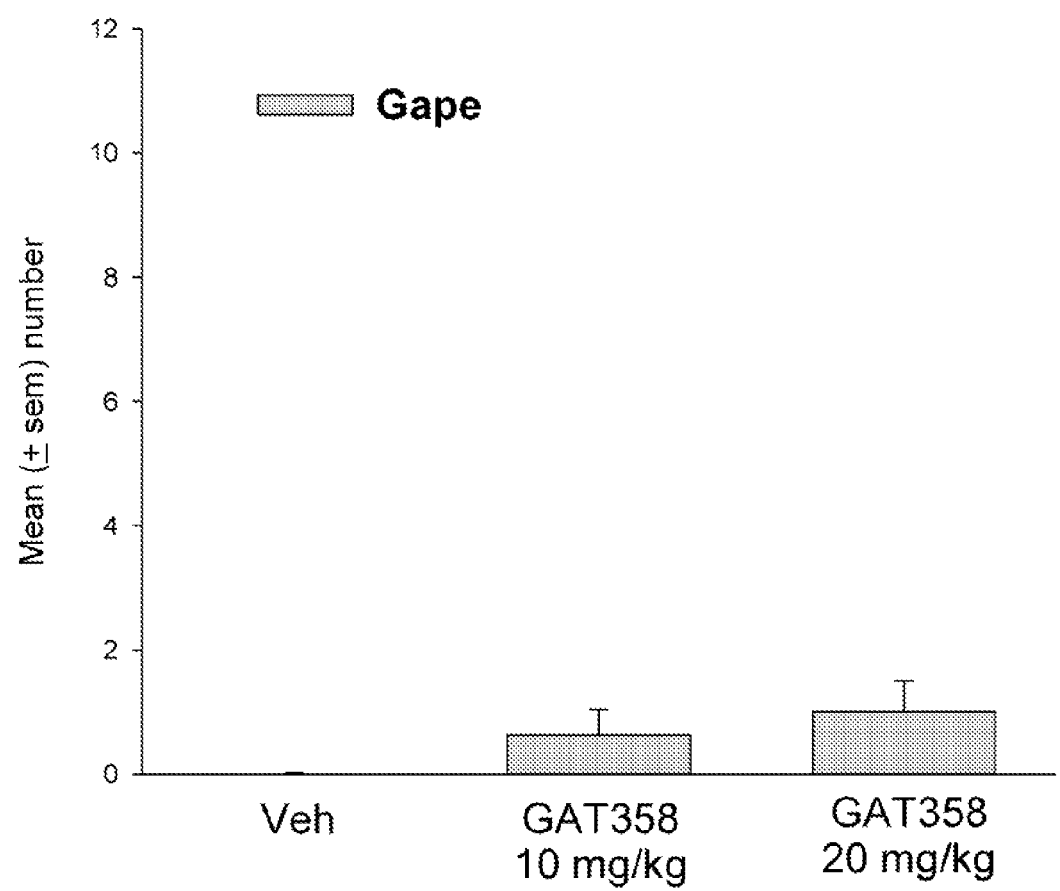
FIG. 2 shows the mean gaping responses expressed by rats during the taste reactivity test in relation to vehicle and an embodiment of the present technology.
Figure 3:
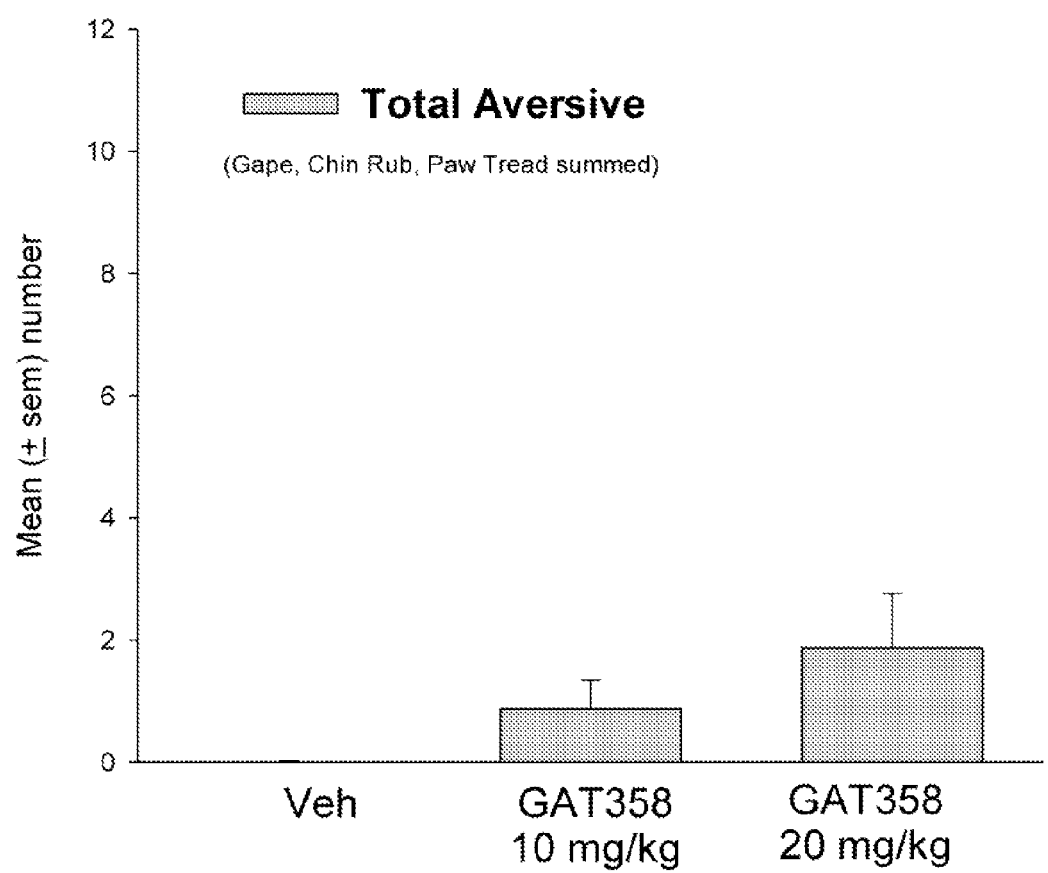
FIG. 3 shows the mean total aversive responses expressed by rats during the drug-free taste reactivity test in relation to vehicle and an embodiment of the present technology.
Figure 4:
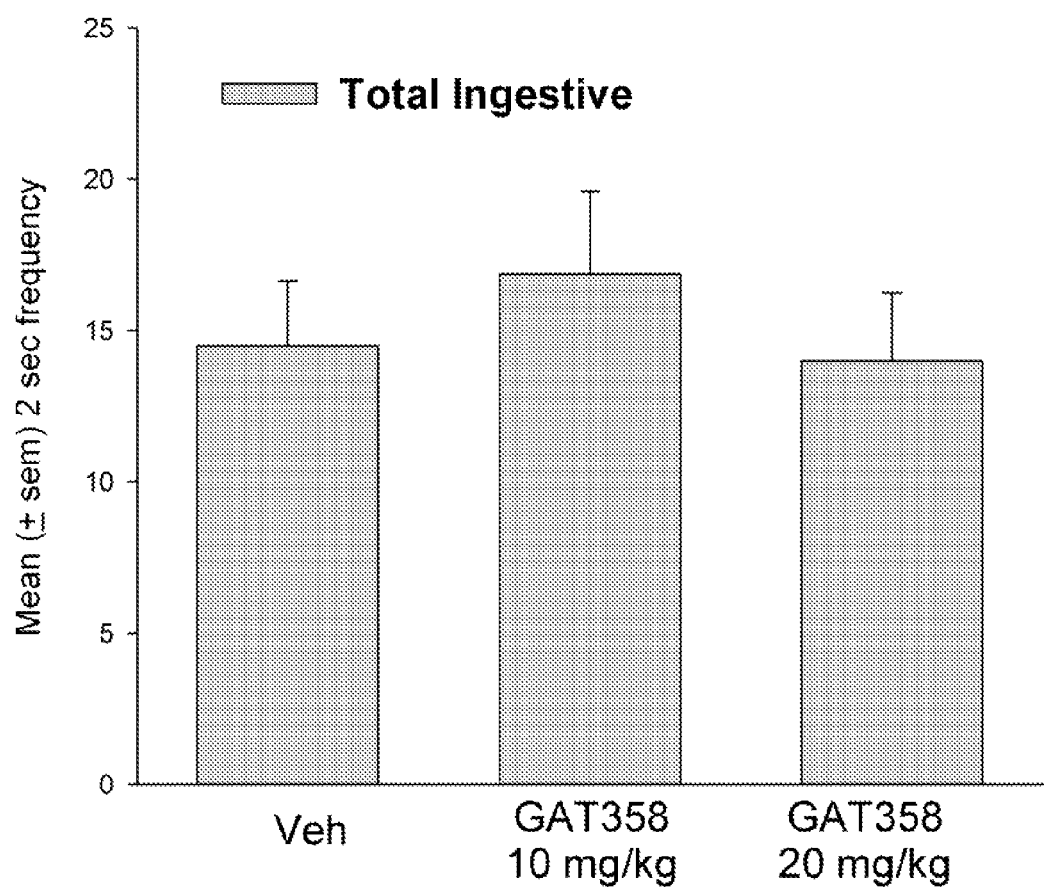
FIG. 4 shows ingestion by rats treated with a vehicle in comparison to an embodiment of the present technology.
Figure 5:
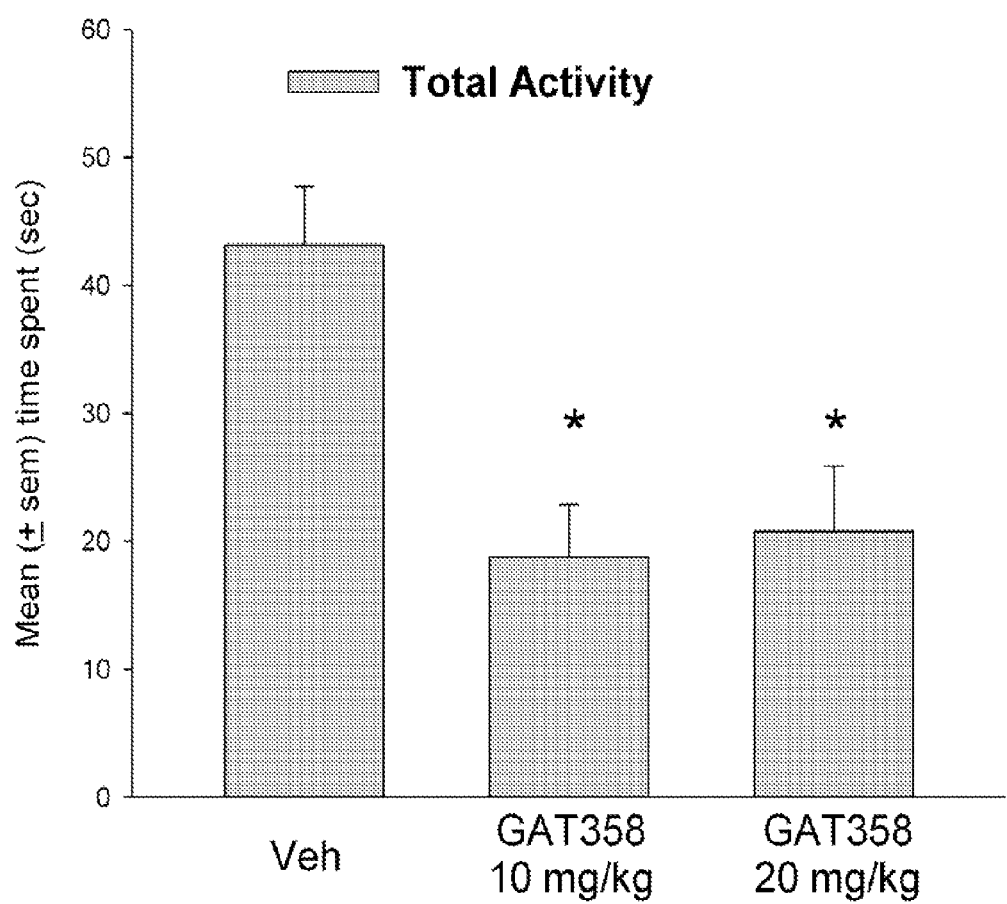
FIG. 5 shows the total activity of rats during the drug-free test with saccharin following conditioning, according to an embodiment.

Results (all analyses were conducted using a one way ANOVA):

Taste Reactivity Test: FIG. 2 presents the mean gaping responses and FIG. 3 presents the mean total aversive responses (gaping, chin rubs and paw treads) expressed by rats during two min saccharin infusion during the drug-free taste reactivity test. GAT358 at either dose did not result in the expression of conditioned gaping or total aversive responses that differed significantly from the vehicle group ($p$'s>0.05). FIG. 4 illustrates that GAT358 at either dose also did not alter conditional ingestive responding to saccharin infusion ($p$>0.05). FIG. 5 illustrates the total activity of rats during the drug-free test with saccharin following conditioning. Analysis revealed a significant effect of drug group, $F(2, 19)=7.5$; $p=0.004$. Subsequent Bonferroni post hoc analysis revealed that the activity of rats in groups GAT358-10 and GAT358-20 was significantly lower than the rats in the vehicle group ($p=0.006$ and $p=0.012$ respectively).

Figure 6:
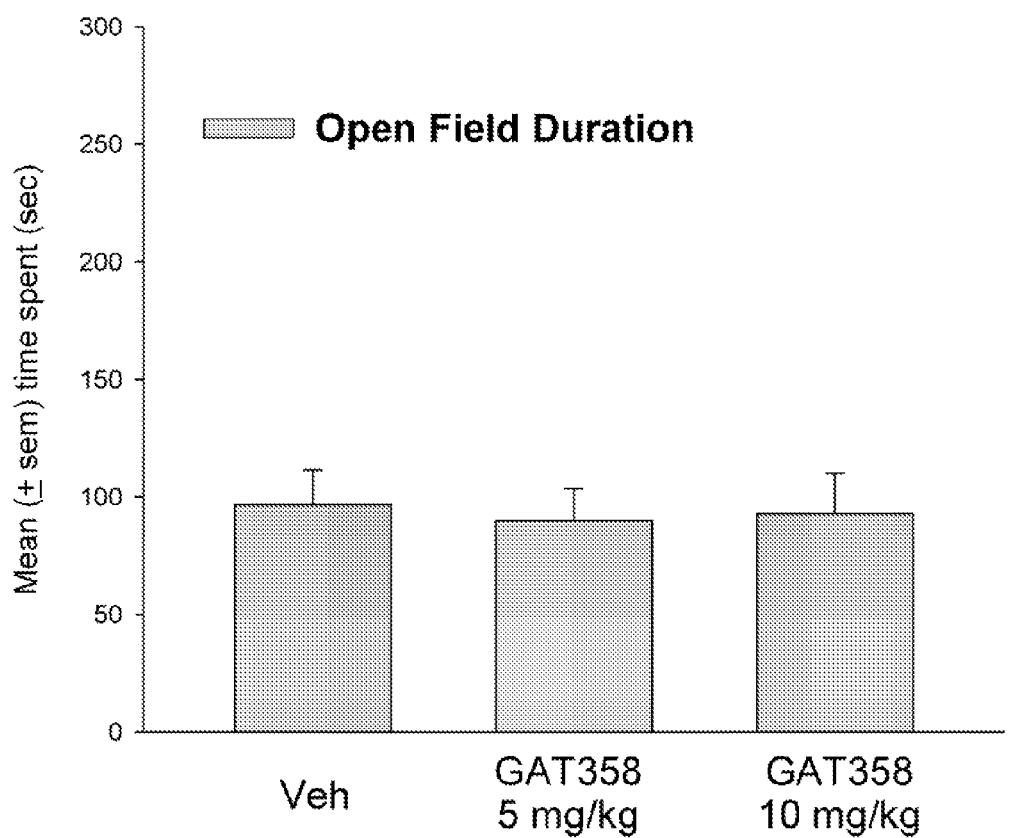
FIG. 6 illustrates the time spent in an open field after administration of vehicle and 5 mg/kg or 10 mg/kg administrations of an embodiment of the present technology in a light dark emergence test.
Figure 7:
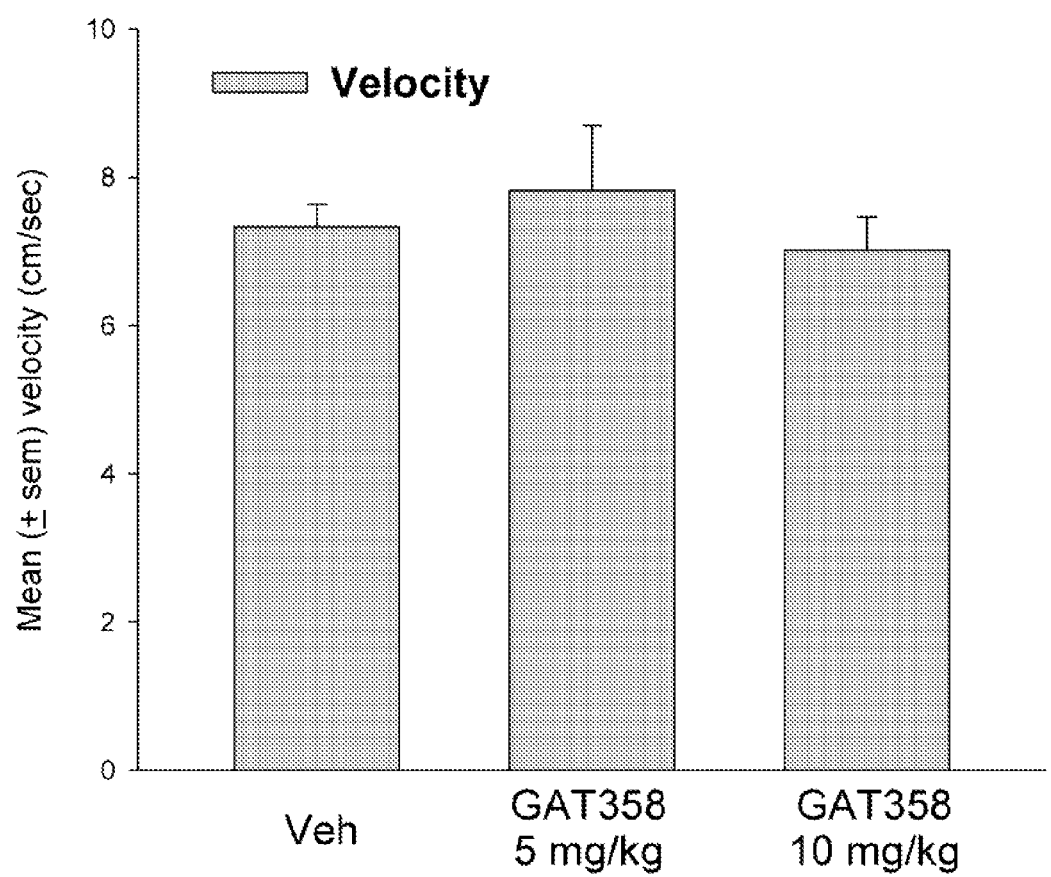
FIG. 7 illustrates the activity of rates administered with a vehicle as well as 5 mg/kg or 10 mg/kg of an embodiment of the present technology in a light dark emergence test.

Light Dark Emergence Test: The administration of GAT358 at either 5 or 10 mg/kg did not significantly alter the time spent in the open field (FIG. 6; $p$>0.05) or the activity of rats during the 5 min in the LDE test (FIG. 7; $p$>0.05).

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein.

Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A compound according to formula VIII

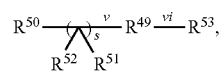

stereoisomers thereof, tautomers thereof, solvates thereof, or pharmaceutically acceptable salts thereof;

wherein v and vi designate the particular bonds indicated in formula VIII;

$R^{49}$ is selected from formulas J or M:

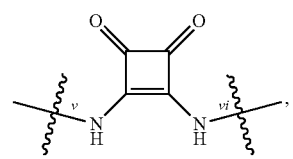

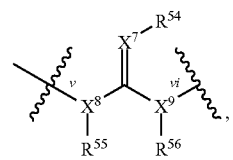

where $X^7$, $X^8$, and $X^9$ are each independently O, N, or S;

$R^{54}$, $R^{55}$, and $R^{56}$ are each independently H, cyano, amino, or a substituted or unsubstituted alkyl, alkanoyl, alkanoyloxy, or aryl group when $X^7$, $X^8$, or $X^9$ are respectively N and are absent when $X^7$, $X^8$, or $X^9$ are respectively O or S;

$R^{50}$ is a substituted or unsubstituted aryl or heteroaryl group;

$R^{51}$ and $R^{52}$ are each independently H or a substituted or unsubstituted alkyl group, or $R^{51}$ and $R^{52}$ together form a 3- or 4-membered cycloalkyl ring;

R⁵³ is a substituted aryl group where one and only one of the substituents is;

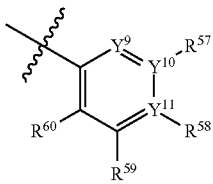

where one of R⁵⁷ or R⁵⁸ is

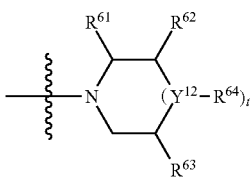

and the other is H, azido, trifluoromethyldiazirido, isocyano, isothiocyano, pentafluorosulfanyl, or a substituted or unsubstituted alkyl, alkanoyl, alkanoyloxy, aryloyl, or aryloyloxy group;

R⁵⁹ and R⁶⁰ are each independently H, halo, azido, trifluoromethyldiazirido, isocyano, isothiocyano, pentafluorosulfuryl, or a substituted or unsubstituted alkyl, alkanoyl, alkanoyloxy, aryloyl, or aryloyloxy group;

Y⁹ is CH;

Y¹⁰ and Y¹¹ are each independently C or N, provided that when Y¹⁰ or Y¹¹ is N then R⁴¹ or R⁴² respectively is absent;

Y¹² is CH, N, O, S, S(O), or S(O)₂;

R⁶¹, R⁶², and R⁶³ are each independently H, azido, trifluoromethyldiazirido, isocyano, isothiocyano, or a substituted or unsubstituted alkyl group;

R⁶⁴ is H or a substituted or unsubstituted alkyl group when Y¹² is CH or N and is absent when Y¹² is O, S, S(O), or S(O)₂;

t is 0 or 1; and s is 0 or 1 wherein the compound is a modulator of a cannabinoid 1 (CB1) receptor.

2. A composition comprising the compound of claim 1 and a pharmaceutically acceptable carrier.

3. A pharmaceutical composition for treating a condition, the pharmaceutical composition comprising a therapeutically effective amount of the compound of claim 1, wherein the condition is addiction, metabolic syndrome, or obesity.

4. A method comprising administering a therapeutically effective amount of a compound of claim 1, or administering a pharmaceutical composition comprising a therapeutically effective amount of a compound of claim 1, to a subject suffering from addiction, metabolic syndrome, or obesity.

5. A method comprising inhibiting β-arrestin in a subject by administering a therapeutically effective amount of a compound of claim 1.

6. The method of claim 5, wherein the subject is suffering from addiction, a metabolic disorder, obesity, or cancer.

7. The method of claim 5, comprising inhibiting β-arrestin recruitment at least 10 times more than inhibiting cyclic AMP formation by administering the therapeutically effective amount of the compound.

8. The method of claim 7, wherein the subject is suffering from addiction, a metabolic disorder, obesity, or cancer.

9. A method for treating an addiction in a subject comprising administering a therapeutically effective amount of a compound of claim 1.

10. The method of claim 9, wherein the addiction is to at least one of nicotine, ethanol, cocaine, opioids, amphetamines, marijuana, and synthetic cannabinoid agonists.

11. The compound of claim 1 which is

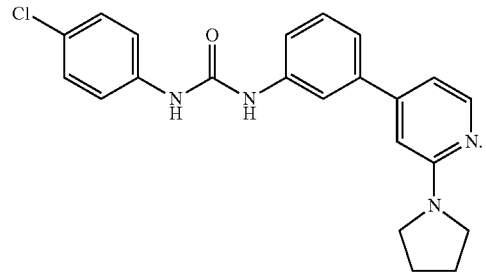 [SMILES: O=C(Nc1ccc(Cl)cc1)Nc1cccc(-c2ccnc(N3CCCC3)c2)c1]

12. The compound of claim 1 which is

* * * * *